US012734228B2

(12) United States Patent
Gonzalez et al.

(10) Patent No.: US 12,734,228 B2
(45) Date of Patent: Sep. 15, 2026

(54) PROTECTIVE VACCINE ANTIGEN AGAINST STREPTOCOCCAL INFECTION

(71) Applicant: The Regents of the University of California, Oakland, CA (US)

(72) Inventors: David J. Gonzalez, La Jolla, CA (US); Anaamika Campeau, La Jolla, CA (US); Dominic M. McGrosso, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 131 days.

(21) Appl. No.: 18/564,537

(22) PCT Filed: May 31, 2022

(86) PCT No.: PCT/US2022/031571
§ 371 (c)(1),
(2) Date: Nov. 27, 2023

(87) PCT Pub. No.: WO2022/256310
PCT Pub. Date: Dec. 8, 2022

(65) Prior Publication Data

US 2024/0285746 A1 Aug. 29, 2024

Related U.S. Application Data

(60) Provisional application No. 63/195,622, filed on Jun. 1, 2021.

(51) Int. Cl.

| | |
|---|---|
| ***A61K 39/02*** | (2006.01) |
| ***A61K 39/09*** | (2006.01) |
| ***A61K 39/39*** | (2006.01) |
| ***A61K 45/06*** | (2006.01) |
| ***A61P 37/04*** | (2006.01) |
| *A61K 39/00* | (2006.01) |

(52) U.S. Cl.
CPC ............ *A61K 39/092* (2013.01); *A61K 39/39* (2013.01); *A61K 45/06* (2013.01); *A61P 37/04* (2018.01); *A61K 2039/55505* (2013.01)

(58) Field of Classification Search
CPC combination set(s) only.
See application file for complete search history.

(56) References Cited

U.S. PATENT DOCUMENTS

2005/0288866 A1 12/2005 Sachdeva et al.
2006/0210580 A1 9/2006 Telford et al.

FOREIGN PATENT DOCUMENTS

WO WO-2015/169773 A2 11/2015

OTHER PUBLICATIONS

Greenspan et al (Nature Biotechnology 7: 936-937, 1999).*
Mikayama et al. (Nov. 1993. Proc. Natl.Acad.Sci. USA, vol. 90 : 10056-10060).*
Moens et al (Infection and Immunity. May 2012 vol. 80(5): 1944-1945).*
Campeau et al., "The S Protein of Group B *Streptococcus* Is a Critical Virulence Determinant That Impacts the Cell Surface Virulome", Frontiers in Microbiology, Oct. 14, 2021, 16 pages.
International Search Report and Written Opinion dated Nov. 3, 2022, for application No. PCT/US2022/031571.
Wierzbicki et al., "Group A Streptococcal S Protein Utilizes Red Blood Cells as Immune Camouflage and Is a Critical Determinant for Immune Evasion", Cell Reports, Dec. 3, 2019, pp. 2979-2980.

* cited by examiner

*Primary Examiner* — Jennifer E Graser
(74) *Attorney, Agent, or Firm* — Foley & Lardner LLP

(57) ABSTRACT

Group A *Streptococcus* (GAS) is associated with an estimated half-million deaths per year and 21 severe autoimmune sequalae. Despite the ubiquity of GAS infection, no vaccine currently exists. Provided herein is a *Streptococcus* S protein or an equivalent thereof used as a vaccine, along with the related compositions and methods.

11 Claims, 24 Drawing Sheets

Specification includes a Sequence Listing.

FIGs. 6A-6B
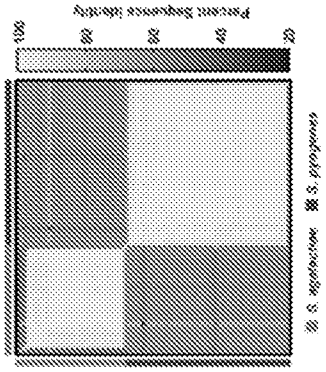
FIG. 6B
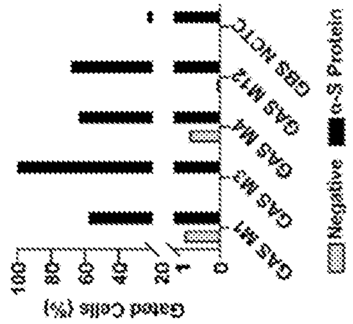
FIG. 6A

PROTECTIVE VACCINE ANTIGEN AGAINST STREPTOCOCCAL INFECTION

CROSS-REFERENCE TO RELATED APPLICATIONS

This application is a U.S. National Phase Application under 35 U.S.C. § 371 of International Patent Application No. PCT/US2022/031571, filed May 31, 2022, which claims priority under 35 U.S.C. § 119 (e) of U.S. Provisional Application 63/195,622, filed Jun. 1, 2021, the contents of each of which are incorporated herein by reference in its entirety.

SEQUENCE LISTING

The instant application contains a Sequence Listing which has been submitted electronically in ASCII format and is hereby incorporated by reference in its entirety. Said ASCII copy, created on Nov. 22, 2023, is named 114198-9111_SL.txt and is 55,572 bytes in size.

BACKGROUND

Group A *Streptococcus* (GAS) is associated with an estimated half-million deaths per year and 21 severe autoimmune sequelae. Despite the ubiquity of GAS infection, no vaccine currently exists. GAS also increases the risk of severe invasive infections, such as sepsis, necrotizing fasciitis and toxic shock syndrome, and is responsible for post-infectious, immune-mediated rheumatic heart disease (RHD), a leading cause of mortality in emerging countries. In the United States, an estimated 17.1% of outpatient antibiotic prescriptions dispensed to children aged 3 to 9 years are for treatment of suspected GAS infections. Studies indicate that antibiotic resistance to GAS has significantly increased in this past decade.

The existing art against *Streptococcus pyogenes* centers around antimicrobial treatment of infection, and no vaccine currently exists. Past studies have evaluated a major *Streptococcus pyogenes* virulence factor, M protein, as a virulence factor. Though highly immunogenic, M protein is a poor candidate for vaccine development for two primary reasons. First, immunity to M protein has been linked to post-streptococcal autoimmune illnesses such as acute rheumatic fever, rheumatic heart disease, and certain neuropsychiatric conditions. Therefore, M protein is undesirable as vaccine as it may not be safe. Second, M protein possesses a hypervariable region, leading to new serotypes being discovered each year. Because of this, M protein would be difficult to develop into a universal vaccine against *Streptococcus pyogenes.*

Therefore, a vaccine remains needed. This disclosure satisfies this need and provides related advantages as well.

SUMMARY OF THE DISCLOSURE

Group A *Streptococcus* (GAS) is associated with an estimated half-million deaths per year and severe autoimmune sequelae. Despite the ubiquity of GAS infection, no vaccine currently exists. Risk of autoimmunity precludes the native forms of major virulence factors M protein and the GAS carbohydrate from being developed as vaccines due to their structural similarity to human antigens. Consequently, it is critical to evaluate other GAS virulence factors for their utility as effective vaccines. Applicant recently developed Biomimetic Virulomics, a mass spectrometry-based virulence factor capture tool to discover and characterize S protein, a central GAS virulence determinant. Here, applicant tested whether a recombinant version of S protein could be an effective vaccine candidate. Applicant found that S protein sequences were nearly identical among multiple GAS strains, and that anti-S protein antibodies bound the surface of multiple GAS serotypes in vitro. S protein is located on the surface of GAS strains. In vivo, S protein-immunized animals showed over a three log reduction in bacteria in a skin infection model when compared to naïve animals. Differential infection clearance was S protein-specific, as immunized and naïve animals infected with an isogenic S protein knock-out mutant strain showed no difference in lesion phenotype. Deep quantitative proteomics of skin lesions demonstrated that whereas naïve animals mounted a robust innate immune defense, S protein-immunized animals showed high levels of immunoglobulins, suggesting that rapid engagement of adaptive immunity underlies GAS clearance. These results provide preclinical data suggesting that S protein is a viable GAS vaccine candidate. Accordingly, disclosed herein is a recombinant S protein as an antigen to be used for immunization instead of a mutant live bacteria as described before (Wierzbicki et al. Cell Rep. 2019 Dec. 3; 29(10):2979-2989.e15; and techtransfer.universityofcalifornia.edu/NCD/31831.html).

In one aspect, provided is a method of treating or preventing a *Streptococcus* infection without inducing an autoimmune sequelae in a subject in need thereof. The method comprises, or consists essentially of, or yet further consists of administering to the subject an effective amount of one or more of: (i) an isolated *Streptococcus* S protein or an equivalent thereof, (ii) an isolated polynucleotide encoding the protein or equivalent of (i), or a complementary polynucleotide thereto, or (iii) a vector comprising the polynucleotide of (ii), thereby treating or preventing the *Streptococcus* infection in the subject without inducing an autoimmune sequelae.

In another aspect, provided is a method for conferring a passive immunity without inducing an autoimmune sequelae to a subject in need thereof. The method comprises, or consists essentially of, or yet further consists of administering an antibody or an antigen binding fragment thereof specifically recognizing and binding a *Streptococcus* S protein or an equivalent thereof, thereby conferring the passive immunity to *Streptococcus* in the subject without inducing an autoimmune sequelae.

In some embodiments, the subject has been infected by or has a high risk of being infected by *Streptococcus*, optionally GAS, and further optionally *S. pyogenes.*

In a further aspect, provided is a kit for use in a method as described herein. The kit comprises, or consists essentially of, or yet further consists of a composition and optionally instructions for use. In some embodiments, the composition comprises, or consists essentially of, or yet further consists of one or more of: the S protein or equivalent of (i), the isolated polynucleotide of (ii), the vector of (iii) or the antibody or antigen binding fragment thereof.

In some embodiments, the S protein is a Group A *Streptococcus* (GAS) S protein, optionally a *Streptococcus pyogenes* (*S. pyogenes*) protein. In further embodiments, the vaccine is useful for preventing or treating a GAS infection. In some embodiments, the *Streptococcus* S protein comprises, or consists essentially of, or yet further consists of MAKEPWEEXXXXDTIGTRTRKSRNAFISTPWX-TALLSVFFVIIVAILFIFFYTSNSGSN RQXETNGFY-GASTHKKXXXKASNAXKXSSSXTTXDXXPSXE-EXLXSSEXTXXXXTVL XGEGXASIAARXGISV- XQLQALNPEHMXQGYWYANPGDXVXIK, wherein X is any amino acid residue or the corresponding amino acid residue in any one of SEQ ID Nos: 1-37 (SEQ ID NO: 38) or an equivalent thereof.

In some embodiments, the composition further comprises a carrier. In further embodiments, the carrier comprises, or consists essentially of, or yet further consists of an adjuvant, optionally an aluminum hydroxide adjuvant.

BRIEF DESCRIPTION OF THE DRAWINGS

(FIG. 1A). Circular dendrogram showing phylogeny of S protein homologs in *Streptococcus* genus detected by PSI-BLAST analysis of GAS S protein template. Matches were filtered to greater than 60% sequence identity and greater than 70% query coverage. Inner circle shows *S. pyogenes* as a portion of all Streptococci, while the outer circle shows species level clustering for non-*S. pyogenes* S protein homologs. (FIG. 1B). In silico prediction of GAS S protein structure generated in Phyre2. (FIG. 1C). Mass spectrometry-based proteomics results of GAS S protein showing predicted modified residues. (FIG. 1D). Detected residue modification unevenness mapping for common modifications.

(FIG. 2A-FIG. 2D). Amino acid frequency plot for S protein surfome peptides detected in GAS M1, M3, M4, and M12 strains. (FIG. 2E). Flow cytometry analysis of GAS emm types following incubation with anti-S protein serum.

(FIG. 3A) Recombinant S protein immunization scheme with downstream outputs. (FIG. 3B) Anti-S protein titer measurements in mice after two-dose immunization scheme with recombinant S protein or alum alone. (FIG. 3C) Pictures demonstrating lesion phenotypes after infection day 3 in S protein immunized or naive animals. (FIG. 3D) Lesion size measurements in S protein naive or immunized animals after day 3 of infection with WT GAS or Δess GAS. Statistical significance was determined using Tukey's multiple comparison test. (FIG. 3E) Recovered CFU enumeration from lesions collected from S protein naive or immunized animals infected with WT GAS or Δess GAS after day 3 of infection. Statistical significance was determined using Tukey's multiple comparison test. *p value<0.05; p value<0.01; *p value<0.001; ****p value<0.0001.

(FIG. 4A) Hierarchical clustering of proteome data from lesions collected from naive and S protein-immunized animals. (FIG. 4B) Identification of differentially abundant proteins via binary comparison. (FIG. 4C-FIG. 4D) Biological Process Gene Ontology term enrichment for proteins associated with GAS infection subsequent to alum (FIG. 4C) or S protein immunization (FIG. 4D). (FIG. 4E) Heatmap demonstrating relative protein abundance for gene ids categorized under "innate immunity" via Biological Process Gene Ontology. (FIG. 4F-FIG. 41). Plotted relative abundance of NCF family proteins in naive and immunized animals during GAS infection. (FIG. 4J) Knowledge-based prediction of the neutrophil activation receptor Cxcr2 with proteins upregulated during infection in naive animals compared to S protein immunized animals. (FIG. 4K) Heatmap demonstrating relative protein abundance for significantly altered immunoglobulins. (FIG. 4L) Average fold change for all immunoglobulins detected. (FIG. 4M) Pie chart demonstrating proportion of immunoglobulins associated with S protein immunization during GAS infection. *p value<0.05; p value<0.01; *p value<0.001.

(FIG. 5A) Heatmap demonstrating sequence identity between *S. pyogenes* S protein sequences. (FIG. 5B) Delta m/z histogram demonstrating putative modifications identified from GNPS-based spectral networking.

FIGS. 6A-6D: GBS NCTC S protein homolog is surface exposed. (FIG. 6A) Percent of cells within gate from flow cytometry analysis. (FIG. 6B) Sequence alignment of *S. pyogenes* (GAS) and *S. agalactiae* (GBS) strains. (FIG. 6C) GBS S protein homolog surfome peptide mapping. (FIG. 6D) Flow cytometry showing binding of antibodies generated against recombinant GAS S protein to the CNCTC 10/84 strain of GBS.

(FIG. 7A). Mice immunized with varying amounts of S protein developed robust anti-S protein antibody responses. (FIG. 7B) CFUs recovered from mice infected with GAS following immunization with 75 μg aliquots of S protein differed significantly between naïve and immunized animals and were used for mass spectrometry based analysis. Significance was determined using Mann-Whitney U Test. *p value<0.05. (FIG. 7C) CFUs recovered from mice infected with GAS following immunization with 25, 50, or 75 μg aliquots of S protein did not differ significantly. Significance was determined using one-way ANOVA.

FIG. 8: Predicted neutrophil receptor regulation of naïve infection-associated skin lesion proteome changes. Predicted neutrophil receptor regulation of proteome feature increased in naïve animals infected with GAS compared to immunized animals.

DETAILED DESCRIPTION

Definitions

Figure 1A:
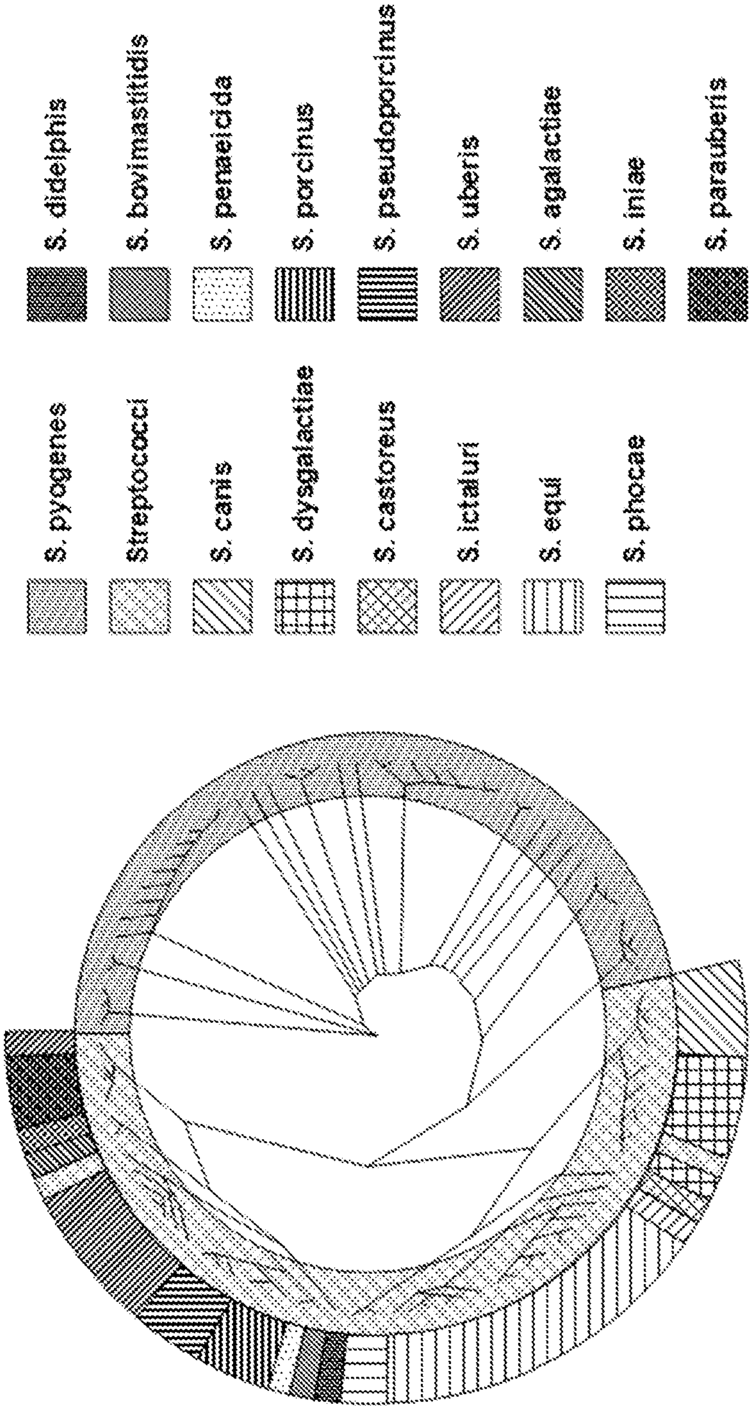
FIGS. 1A-1D: Sequence characterization of recombinant S protein vaccine candidate.

As it would be understood, the section or subsection headings as used herein is for organizational purposes only and are not to be construed as limiting and/or separating the subject matter described.

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present disclosure, the preferred methods, devices, and materials are now described. All technical and patent publications cited herein are incorporated herein by reference in their entirety. Nothing herein is to be construed as an admission that the disclosure is not entitled to antedate such disclosure by virtue of prior disclosure.

The practice of the present disclosure will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press);

MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, 3rd edition (Cold Spring Harbor Laboratory Press (2002)); Sohail (ed.) (2004) Gene Silencing by RNA Interference: Technology and Application (CRC Press).

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compounds, compositions and methods include the recited elements, but not exclude others. "Consisting essentially of" when used to define compounds, compositions and methods, shall mean excluding other elements of any essential significance to the combination. Thus, a composition consisting essentially of the elements as defined herein would not exclude trace contaminants, e.g., from the isolation and purification method and pharmaceutically acceptable carriers, preservatives, and the like. "Consisting of" shall mean excluding more than trace elements of other ingredients. Embodiments defined by each of these transition terms are within the scope of this technology.

All numerical designations, e.g., pH, temperature, time, concentration, and molecular weight, including ranges, are approximations which are varied (+) or (−) by increments of 1, 5, or 10%. It is to be understood, although not always explicitly stated that all numerical designations are preceded by the term "about." It also is to be understood, although not always explicitly stated, that the reagents described herein are merely exemplary and that equivalents of such are known in the art.

As used herein, comparative terms as used herein, such as high, low, increase, decrease, reduce, or any grammatical variation thereof, can refer to certain variation from the reference. In some embodiments, such variation can refer to about 10%, or about 20%, or about 30%, or about 40%, or about 50%, or about 60%, or about 70%, or about 80%, or about 90%, or about 1 fold, or about 2 folds, or about 3 folds, or about 4 folds, or about 5 folds, or about 6 folds, or about 7 folds, or about 8 folds, or about 9 folds, or about 10 folds, or about 20 folds, or about 30 folds, or about 40 folds, or about 50 folds, or about 60 folds, or about 70 folds, or about 80 folds, or about 90 folds, or about 100 folds or more higher than the reference. In some embodiments, such variation can refer to about 1%, or about 2%, or about 3%, or about 4%, or about 5%, or about 6%, or about 7%, or about 8%, or about 0%, or about 10%, or about 20%, or about 30%, or about 40%, or about 50%, or about 60%, or about 70%, or about 75%, or about 80%, or about 85%, or about 90%, or about 95%, or about 96%, or about 97%, or about 98%, or about 99% of the reference.

"Optional" or "optionally" means that the subsequently described circumstance may or may not occur, so that the description includes instances where the circumstance occurs and instances where it does not.

As used herein, "and/or" refers to and encompasses any and all possible combinations of one or more of the associated listed items, as well as the lack of combinations when interpreted in the alternative ("or").

"Substantially" or "essentially" means nearly totally or completely, for instance, 95% or greater of some given quantity. In some embodiments, "substantially" or "essentially" means 95%, 96%, 97%, 98%, 99%, 99.5%, or 99.9%.

The terms or "acceptable," "effective," or "sufficient" when used to describe the selection of any components, ranges, dose forms, etc. disclosed herein intend that said component, range, dose form, etc. is suitable for the disclosed purpose.

As will be understood by one skilled in the art, for any and all purposes, all ranges disclosed herein also encompass any and all possible subranges and combinations of subranges thereof. Furthermore, as will be understood by one skilled in the art, a range includes each individual member.

The terms "oligonucleotide" or "polynucleotide" or "portion," or "segment" thereof refer to a stretch of polynucleotide residues which is long enough to use in PCR or various hybridization procedures to identify or amplify identical or related parts of mRNA or DNA molecules. The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complementary of such a nucleic acid, and the encoding sequence can be deduced therefrom.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

In some embodiments, the term "engineered" refers to comprising at least one modification not normally found in a naturally occurring counterpart, wild-type or a parent. Such as an engineered NK cell can comprise a chimeric antigen receptor (CAR) that is not naturally occurring. In some embodiments, the term "engineered" is used interchangeably with "recombinant" refers to being synthetized by human.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, fragment, polypeptide or nucleic acid, intends those having minimal homology while still maintaining desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide or Fab (fragment antigen binding) intends one that binds with at least 70%, or alternatively at least 75%, or alternatively at least 80%, or alternatively at least 85%, or alternatively at least 90%, or alternatively at least 95% affinity or higher affinity to a reference antibody or antigen binding fragment. In another aspect, the equivalent thereof competes with the binding of the antibody or antigen binding fragment to its antigen under a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. In certain embodiments, default parameters are used for alignment. A non-limiting exemplary alignment program is BLAST, using default parameters. In particular, exemplary programs include BLASTN and BLASTP, using the following default parameters: Genetic code=standard; filter-none; strand=both; cutoff-60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. Sequence identity and percent identity can determined by incorporating them into clustalW (available at the web address:genome.jp/tools/clustalw/, last accessed on Jan. 13, 2017).

In some embodiments, the vector as used herein is a non-viral vector, such as a liposome, micelle or a plasmid. In other embodiments, the vector as used herein is a viral vector.

"Liposomes" are microscopic vesicles consisting of concentric lipid bilayers. A liposome is an example of a carrier, e.g., a pharmaceutically acceptable carrier. Structurally, liposomes range in size and shape from long tubes to spheres, with dimensions from a few hundred Angstroms to fractions of a millimeter. Vesicle-forming lipids are selected to achieve a specified degree of fluidity or rigidity of the final complex providing the lipid composition of the outer layer. These are neutral (cholesterol) or bipolar and include phospholipids, such as phosphatidylcholine (PC), phosphatidylethanolamine (PE), phosphatidylinositol (PI), and sphingomyelin (SM) and other types of bipolar lipids including but not limited to dioleoylphosphatidylethanolamine (DOPE), with a hydrocarbon chain length in the range of 14-22, and saturated or with one or more double C═C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanol-amine, phosphatidylserine, phosphatidylinositol, sphingomyelin, cephalin, cardiolipin, phosphatidic acid, cerebrosides, distearoylphosphatidylethan-olamine (DSPE), dioleoylphosphatidylcholine (DOPC), dipalmitoylphosphatidylcholine (DPPC), palmitoyloteoylphosphatidylcholine (POPC), palmitoyloleoylphosphatidylethanolamine (POPE) and dioleoylphosphatidylethanolamine 4-(N-maleimido-triethyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stearate, amphoteric acrylic polymers, polyethyoxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylglycerol (DPPG), dioleoylphosphatidylglycerol and (DOPG), dicetylphosphate that are able to form vesicles. Typically, liposomes can be divided into three categories based on their overall size and the nature of the lamellar structure. The three classifications, as developed by the New York Academy Sciences Meeting, "Liposomes and Their Use in Biology and Medicine," December 1977, are multi-lamellar vesicles (MLVs), small uni-lamellar vesicles (SUVs) and large uni-lamellar vesicles (LUVs). The biological active agents can be encapsulated in such for administration in accordance with the methods described herein.

A "micelle" is an aggregate of surfactant molecules dispersed in a liquid colloid. A typical micelle in aqueous solution forms an aggregate with the hydrophilic "head" regions in contact with surrounding solvent, sequestering the hydrophobic tail regions in the micelle center. This type of micelle is known as a normal phase micelle (oil-in-water micelle). Inverse micelles have the head groups at the center with the tails extending out (water-in-oil micelle). Micelles can be used to attach a polynucleotide, polypeptide, antibody, antigen binding fragment, vaccine, or composition described herein to facilitate efficient delivery to the target cell or tissue.

The phrase "pharmaceutically acceptable polymer" refers to the group of compounds which can be conjugated to one or more polypeptides or antibodies described here. It is contemplated that the conjugation of a polymer to the polypeptide or antibody is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof. The biological active agents can be conjugated to a pharmaceutically acceptable polymer for administration in accordance with the methods described herein.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extra-chromosomal replicon (e.g., a plasmid) or a nuclear or mitochondrial chromosome. A number of vectors are known to be capable of mediating transfer of genes to mammalian cells, as is known in the art and described herein.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

A "viral vector" is defined as a recombinantly produced virus or viral particle that comprises a polynucleotide to be delivered into a host cell, either in vivo, ex vivo or in vitro.

Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene. Further details as to modern methods of vectors for use in gene transfer may be found in, for example, Kotterman et al. (2015) Viral Vectors for Gene Therapy: Translational and Clinical Outlook Annual Review of Biomedical Engineering 17.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. Ads do not require integration into the host cell genome. Recombinant Ad derived vectors, particularly those that reduce the potential for recombination and generation of wild-type virus, have also been constructed. Such vectors are commercially available from sources such as Takara Bio USA (Mountain View, CA), Vector Biolabs (Philadelphia, PA), and Creative Biogene (Shirley, NY). Wild-type AAV has high infectivity and specificity integrating into the host cell's genome. See, Wold and Toth (2013) Curr. Gene. Ther. 13(6):421-433, Hermonat & Muzyczka (1984) Proc. Natl. Acad. Sci. USA 81:6466-6470, and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Agilent Technologies (Santa Clara, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

As used herein, the terms "antibody," "antibodies" and "immunoglobulin" includes whole antibodies and any antigen binding fragment or a single chain thereof. Thus the term "antibody" includes any protein or peptide containing molecule that comprises at least a portion of an immunoglobulin molecule. The terms "antibody," "antibodies" and "immunoglobulin" also include immunoglobulins of any isotype, fragments of antibodies which retain specific binding to antigen, including, but not limited to, Fab, Fab', $F(ab)_2$, Fv, scFv, dsFv, Fd fragments, dAb, VH, VL, VhH, and V-NAR domains; minibodies, diabodies, triabodies, tetrabodies and kappa bodies; multispecific antibody fragments formed from antibody fragments and one or more isolated. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, at least one portion of a binding protein, chimeric antibodies, humanized antibodies, species-ized antibodies, single-chain antibodies, and fusion proteins comprising an antigen-binding portion of an antibody and a non-antibody protein. The variable regions of the heavy and light chains of the immunoglobulin molecule contain a binding domain that interacts with an antigen. The constant regions of the antibodies (Abs) may mediate the binding of the immunoglobulin to host tissues.

The antibodies can be polyclonal, monoclonal, multispecific (e.g., bispecific antibodies), a diabody, and antibody fragments, so long as they exhibit the desired biological activity. Antibodies can be isolated from any suitable biological source, e.g., a human, a murine, rat, sheep and canine.

As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like and can be used, therapeutically, diagnostically or to isolate a polypeptide.

Monoclonal antibodies may be generated using hybridoma techniques or recombinant DNA methods known in the art. A hybridoma is a cell that is produced in the laboratory from the fusion of an antibody-producing lymphocyte and a non-antibody producing cancer cell, usually a myeloma or lymphoma. A hybridoma proliferates and produces a continuous sample of a specific monoclonal antibody. Alternative techniques for generating or selecting antibodies include in vitro exposure of lymphocytes to antigens of interest, and screening of antibody display libraries in cells, phage, or similar systems.

The term "human antibody" as used herein, is intended to include antibodies having variable and constant regions derived from human germline immunoglobulin sequences. The human antibodies disclosed herein may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, CL, CH domains (e.g., CH1, CH2, CH3), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin. Additional non-limiting examples of linker polypeptides are provided herein.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

"human monoclonal antibody" refers to antibodies displaying a single binding specificity which have variable and constant regions derived from human germline immunoglobulin sequences. The term also intends recombinant human antibodies.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, chimeric antibodies are antibodies whose light and heavy chain genes have been constructed, typically by genetic engineering, from antibody variable and constant region genes belonging to different species.

As used herein, the term "humanized antibody" or "humanized immunoglobulin" refers to a human/non-human chimeric antibody that contains a minimal sequence derived from non-human immunoglobulin. For the most part, humanized antibodies are human immunoglobulins (recipient antibody) in which residues from a variable region of the recipient are replaced by residues from a variable region of a non-human species (donor antibody) such as mouse, rat, rabbit, or non-human primate having the desired specificity, affinity and capacity. Humanized antibodies may comprise residues that are not found in the recipient antibody or in the donor antibody. The humanized antibody can optionally also comprise at least a portion of an immunoglobulin constant region (Fc), typically that of a human immunoglobulin, a non-human antibody containing one or more amino acids in a framework region, a constant region or a CDR, that have been substituted with a correspondingly positioned amino acid from a human antibody. In general, humanized antibodies are expected to produce a reduced immune response in a human host, as compared to a non-humanized version of the same antibody. The humanized antibodies may have conservative amino acid substitutions which have substantially no effect on antigen binding or other antibody functions. Conservative substitutions groupings include: glycine-alanine, valine-leucine-isoleucine, phenylalanine-tyrosine, lysine-arginine, alanine-valine, serine-threonine and asparagine-glutamine. The term "species-ized" refers to antibodies that have been modified in the same or a similar manner for a non-human species.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope. In some embodiments, the antibody or antigen binding fragment is not a polyclonal antibody.

As used herein, the term “antibody derivative”, comprises a full-length antibody or a fragment of an antibody, wherein one or more of the amino acids are chemically modified by alkylation, pegylation, acylation, ester formation or amide formation or the like, e.g., for linking the antibody to a second molecule. This includes, but is not limited to, pegylated antibodies, cysteine-pegylated antibodies, and variants thereof. This disclosure also provided antibody derivatives of the antibody fragments, e.g., the polypeptides conjugated to another molecule, e.g., PEG or further modified by acylation.

As used herein, the term “immunoconjugate” comprises an antibody, an antibody fragment or an antibody derivative associated with or linked to a second agent, such as a cytotoxic agent, a detectable agent, a radioactive agent, a targeting agent, a human antibody, a humanized antibody, a chimeric antibody, a synthetic antibody, a semisynthetic antibody, or a multispecific antibody. This disclosure provides immunoconjugates comprising as one component, an antibody or Fab fragment and the second agent.

As used herein, the term “label” intends a directly or indirectly detectable compound or composition that is conjugated directly or indirectly to the composition to be detected, e.g., N-terminal histidine tags (N-His), magnetically active isotopes, e.g., $^{115}Sn$, $^{117}Sn$ and $^{119}Sn$, a non-radioactive isotopes such as $^{13}C$ and $^{15}N$, polynucleotide or protein such as an antibody so as to generate a “labeled” composition. The term also includes sequences conjugated to a polynucleotide that will provide a signal upon expression of the inserted sequences, such as green fluorescent protein (GFP) and the like. The term also includes purification tags or labels that aid in the isolation of biological materials from mixed populations. While the term “label” generally intends compositions covalently attached to the composition to be detected, in one aspect it specifically excludes naturally occurring nucleosides and amino acids that are known to fluoresce under certain conditions (e.g., temperature, pH, etc.) when positioned within the polynucleotide or protein in its native environment and generally any natural fluorescence that may be present in the composition to be detected. The label may be detectable by itself (e.g., radioisotope labels or fluorescent labels) or, in the case of an enzymatic label, may catalyze chemical alteration of a substrate compound or composition that is detectable. The labels can be suitable for small-scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals (6th ed). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, CASCADE BLUE™, and Texas Red.

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

The terms “antigen” and “antigenic” refer to molecules with the capacity to be recognized by an antibody or otherwise act as a member of an antibody-ligand pair. “Specific binding” refers to the interaction of an antigen with the variable regions of immunoglobulin heavy and light chains. Antibody-antigen binding may occur in vivo or in vitro. The skilled artisan will understand that macromolecules, including proteins, nucleic acids, fatty acids, lipids, lipopolysaccharides and polysaccharides have the potential to act as an antigen. The skilled artisan will further understand that nucleic acids encoding a protein with the potential to act as an antibody ligand necessarily encode an antigen. The artisan will further understand that antigens are not limited to full-length molecules, but can also include partial molecules. The term “antigenic” is an adjectival reference to molecules having the properties of an antigen. The term encompasses substances that are immunogenic, i.e., immunogens, as well as substances which induce immunological unresponsiveness, or anergy, i.e., anergens.

“Immune response” broadly refers to the antigen-specific responses of lymphocytes to foreign substances. The terms “immunogen” and “immunogenic” refer to molecules with the capacity to elicit an immune response. All immunogens are antigens; however, not all antigens are immunogenic. An immune response disclosed herein can be humoral (via antibody activity) or cell-mediated (via T cell activation). The response may occur in vivo or in vitro. The skilled artisan will understand that a variety of macromolecules, including proteins, nucleic acids, fatty acids, lipids, lipopolysaccharides and polysaccharides have the potential to be immunogenic. The skilled artisan will further understand that nucleic acids encoding a molecule capable of eliciting an immune response necessarily encode an immunogen. The artisan will further understand that immunogens are not limited to full-length molecules, but may include partial molecules.

The term “passive immunity” refers to the transfer of immunity from one subject to another through the transfer of antibodies. Passive immunity may occur naturally, as when maternal antibodies are transferred to a fetus. Passive immunity may also occur artificially as when antibody compositions are administered to non-immune subjects. Antibody donors and recipients may be human or non-human subjects. Antibodies may be polyclonal or monoclonal, may be generated in vitro or in vivo, and may be purified, partially purified, or unpurified depending on the embodiment. In some embodiments described herein, passive immunity is conferred on a subject in need thereof through the administration of antibodies or antigen binding fragments that specifically recognize or bind to a particular antigen. In some embodiments, passive immunity is conferred through the administration of an isolated or recombinant polynucleotide encoding an antibody or antigen binding fragment that specifically recognizes or binds to a particular antigen.

As used herein, the term "inducing an immune response in a subject" is a term well understood in the art and intends that an increase of at least about 2-fold, at least about 5-fold, at least about 10-fold, at least about 100-fold, at least about 500-fold, or at least about 1000-fold or more in an immune response to an antigen (or epitope) can be detected or measured, after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody, and production of an immune cell expressing on its surface a molecule which specifically binds to an antigen (or epitope). Methods of determining whether an immune response to a given antigen (or epitope) has been induced are well known in the art. For example, antigen-specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody).

In one embodiment, the term "autoimmune sequelae" refers to a pathological condition comprising, or consisting essentially of, or yet further consisting of an immune response directed against an auto- or self-antigen of the subject. As described herein, a *Streptococcus pyogenes* infection, administration of *Streptococcus pyogenes* M protein, or administration of *Streptococcus pyogenes* carbohydrate can induce an autoimmune sequelae, thus is harmful. Accordingly, unlike the S protein as disclosed herein, the inactivated *Streptococcus pyogenes, Streptococcus pyogenes* M protein, and *Streptococcus pyogenes* carbohydrate are not suitable for uses as a vaccine.

As used herein, the term "vaccine" refers to a composition or an agent (such as a polypeptide, a polynucleotide or a vector) that elicits a cellular and/or humoral immune response when administered to a subject, such as a vertebrate, preferably an animal, preferably a mammal, and more preferably a human. Upon introduction into the subject, the vaccine is able to provoke an immune response, preferably a detectable immune response, including, but not limited to, the production of antibodies, cytokines and/or the activation of cytotoxic T cells, antigen presenting cells, helper T cells, dendritic cells and/or other cellular responses. Vaccines of the present invention can include or be administered in or with an adjuvant.

A "composition" as used herein, refers to an active agent, such as a compound as disclosed herein and a carrier, inert or active. The carrier can be, without limitation, solid such as a bead or resin, or liquid, such as phosphate buffered saline.

A "preservative" is a natural or synthetic chemical that is added to products such as foods, pharmaceuticals, paints, biological samples, wood, etc. to prevent decomposition by microbial growth or by undesirable chemical changes. Preservative additives can be used alone or in conjunction with other methods of preservation. Preservatives may be antimicrobial preservatives, which inhibit the growth of bacteria and fungi, or antioxidants such as oxygen absorbers, which inhibit the oxidation of constituents. Common antimicrobial preservatives include, benzalkonium chloride, benzoic acid, chlorohexidine, glycerin, phenol, potassium sorbate, thimerosal, sulfites (sulfur dioxide, sodium bisulfite, potassium hydrogen sulfite, etc.) and disodium EDTA. Other preservatives include those commonly used in patenteral proteins such as benzyl alcohol, phenol, m-cresol, chlorobutanol or methylparaben.

As used herein, the term "animal" refers to living multicellular vertebrate organisms, a category that includes, for example, mammals and birds. The term "mammal" includes both human and non-human mammals.

The term "subject," "host," "individual," and "patient" are as used interchangeably herein to refer to animals, typically mammalian animals. Any suitable mammal can be treated by a method described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments, a mammal is a human. A mammal can be any age or at any stage of development (e.g., an adult, teen, child, infant, or a mammal in utero). A mammal can be male or female. In some embodiments, a subject is a human. In some embodiments, a subject has or is diagnosed of having or is suspected of having a disease.

As used herein, in some embodiments, S protein refers to SPy_0802 protein that bound RBC membranes with high affinity and subsequently examined. See, Wierzbicki. et al. *Cell Rep.* 29, 2979-2989.e15 (2019). In some embodiments, S protein refers to a LysM peptidoglycan-binding domain-containing protein.

In some embodiments, the term "disease" or "disorder" as used herein refers to a *Streptococcus* infection, a status of being diagnosed with a *Streptococcus* infection, a status of being suspect of having a *Streptococcus* infection, or a status of at high risk of having a *Streptococcus* infection. In further embodiments, the infection is a GAS infection, e.g. *S. pyogenes*. In some embodiments, the term "disease" or "disorder" as used herein also refer to a condition associated with a *Streptococcus* infection, such as a condition caused by the *Streptococcus* infection or a symptom of being infected by *Streptococcus*. Non-limiting examples of the condition include, e.g., scarlet fever, necrotizing fasciitis, bacteremia, pneumonia, streptococcal toxic shock syndrome (STSS), rheumatic heart disease, superficial infections, such as impetigo, cellulitis, necrotizing fasciitis, pharyngitis, glomerulonephritis, acute rheumatic fever (ARF), rheumatic heart disease (RHD), or neuropsychiatric diseases. Accordingly, the *Streptococcus* infection as used herein may be substituted with a condition associated with the *Streptococcus* infection.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. In one aspect, treatment excludes prophylaxis.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. In general, one will desire to administer an amount of the compound that is effective to achieve a serum level commensurate with the concentrations found to be effective in vivo. These considerations, as well as effective formulations and administration procedures are well known in the art and are described in standard textbooks.

"Administration" or "delivery" of a therapeutic or other agent can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, inhalation, intramuscular administration, subcutaneous administration, intradermal administration, injections and topical application. Administration can be for use in industrial as well as therapeutic applications.

An agent (an antibody or fragment thereof, a polypeptide, a polynucleotide, a cell, a composition or a vaccine) of the present disclosure can be administered for its intended use whether in vitro or in vivo (e.g., therapeutically) by any suitable route of administration. It will also be appreciated that the optimal route will vary with the condition and age of the recipient, and the disease being treated. The agent may be used in industrial settings and for the treatment of animals.

MODES FOR CARRYING OUT THE DISCLOSURE

Group A *Streptococcus* (GAS) is among the most common infectious agents worldwide, with an estimated 700 million infections per year. Commonly recognized as the cause of "strep throat," GAS is also a common cause of skin and soft tissue infections (SSTIs), causing self-resolving illnesses such as impetigo, a superficial skin infection. Impetigo can progress to the deeper layers of the skin and musculature, where it causes life-threatening disease, or elicit autoimmune glomerulonephritis, a cause of kidney failure. GAS skin infections are highly contagious and can spread to the upper respiratory tract, where the pathogen may instigate autoimmune conditions including acute rheumatic fever, rheumatic heart disease, and even neuropsychiatric conditions. While morbidity and mortality from GAS cases is relatively low in the developed world, poor outcomes of GAS infection are common in areas with high rates of poverty and limited access to medical care. Thus, there is a critical need for a universal, safe vaccine against this pathogen.

No vaccine against *Streptococcus pyogenes* currently exists. Approaches to combatting infection are centered around antimicrobials, especially penicillin, though treatment is rare in areas where poverty is endemic and there is poor access to healthcare. The disclosure herein fills a gap in prophylactic agents against *Streptococcus pyogenes*, a top-ten infectious disease and major cause of morbidity and mortality worldwide. Past studies have proposed various streptococcal antigens or combinations of antigens as vaccine candidates against *Streptococcus pyogenes*, though none have been commercialized yet. However, data as disclosed herein on the immunization potential of S protein indicates that it is one of the most potent vaccines described to date, resulting in over a three log-fold reduction in bacterial CFU recovery compared to lesions collected from unimmunized animals. Additionally, unlike the most prominent *Streptococcus pyogenes* antigens, M protein and the *Streptococcus pyogenes* carbohydrate, there is no evidence that immunity against S protein is linked to harmful autoimmune sequelae. Given its ability to rapidly clear *Streptococcus pyogenes* from skin lesions, S protein is a superior vaccine against this pathogen.

Immunization with recombinant S protein elicits a potent antibody-based response in vivo. Antibodies specific to S protein bind the surface of the bacteria in an S protein-dependent manner, killing the bacteria through enhanced complement binding or by sensitizing them to phagocytosis.

The vaccine and composition as disclosed herein potently stimulates the immune system to produce antibodies that clear *Streptococcus pyogenes* infection. Recombinant S protein is injected into a subject and the subject is then exposed to *Streptococcus pyogenes*. On infection, circulating antibodies against S protein bind the bacteria in an S protein-specific manner. The antibodies can lead to bacterial killing in two primary ways. First, antibody binding can sensitize the bacteria to killing via the complement system. Second, antibodies can coat the bacteria, allowing phagocytes to better recognize bacteria leading to engulfment and intracellular killing. Although the mechanism of antibody-mediated killing of bacteria is unclear, anti-S protein antibodies potently lead to reduction in lesion size and clearance of infection compared to infected naïve animals.

Applicant results establish S protein as a viable candidate for further development in GAS vaccination strategies. Recombinant S protein elicited a strong antibody response in vivo and demonstrated robust immunity against localized GAS infection in an S protein-dependent manner. Unbiased quantitative proteome analysis revealed the molecular underpinnings of the differential bacterial clearance in immunized versus naïve animals. In naïve animals, protein abundance changes during GAS infection reflected innate immune processes like oxidative burst and were predicted to be regulated by innate immune relay receptors TLR4 and Cxcr2. This contrasted starkly with host pathways elicited by infection in immunized animals, where immunoglobulins were the most prominent increased features. Together, these results align with the expected response to infection in host systems previously exposed to a foreign antigen.

In one aspect, provided is a method of treating or preventing a *Streptococcus* infection without inducing an autoimmune sequelae in a subject in need thereof. The method comprises, or consists essentially of, or yet further consists of administering to the subject an effective amount of one or more of: (i) an isolated *Streptococcus* S protein or an equivalent thereof, (ii) an isolated polynucleotide encoding the protein or equivalent of (i), or a complementary polynucleotide thereto, or (iii) a vector comprising the polynucleotide of (ii). In some embodiments, the method treats or prevents the *Streptococcus* infection in the subject without inducing an autoimmune sequelae.

In a further aspect, provided is a method of treating or preventing a *Streptococcus* infection in a subject in need thereof. The method comprises, or consists thereof, or yet further consists of administering to the subject, such as an effective amount or an immunogenic dose of a vaccine composition as disclosed herein. In some embodiments, the method treats or prevents the *Streptococcus* infection in the subject. In further embodiments, the methods does not induce an autoimmune sequelae.

In some embodiments, the S protein comprises, or consists essentially of, or yet further consists of a Group A *Streptococcus* (GAS) S protein. In further embodiments, the GAS comprises, or consists essentially of, or yet further consists of *Streptococcus pyogenes* (*S. pyogenes*).

In some embodiments, the S protein comprises, or consists essentially of, or yet further consists of a Group B *Streptococcus* (GBS) S protein. In further embodiments, the GBS comprises, or consists essentially of, or yet further consists of *Streptococcus agalactiae* (*S. agalactiae*).

In some embodiments, the *Streptococcus* is selected from the group consisting of *Streptococcus equi* (*S. equi*), *Streptococcus dysgalactiae* (*S. dysgalactiae*), *Streptococcus canis* (*S. canis*), *Streptococcus phocae* (*S. phocae*), *Streptococcus castoreus* (*S. castoreus*), *Streptococcus ictaluri* (*S. ictaluri*), *Streptococcus didelphis* (*S. didelphis*), *Streptococcus bovimastitidis* (*S. bovimastitidis*), *Streptococcus penaeicida* (*S. penaeicida*), *Streptococcus porcinus* (*S. porcinus*), *Streptococcus pseudoporcinus* (*S. pseudoporcinus*), *Streptococcus uberis* (*S. uberis*), *Streptococcus iniae* (*S. iniae*), or *Streptococcus parauberis* (*S. parauberis*).

Additionally or alternatively, the *Streptococcus* S protein comprises, or consists essentially of, or yet further consists of one or more of: a *Streptococcus equi* (*S. equi*) S protein, a *Streptococcus dysgalactiae* (*S. dysgalactiae*) S protein, a *Streptococcus canis* (*S. canis*) S protein, a *Streptococcus phocae* (*S. phocae*) S protein, a *Streptococcus castoreus* (*S. castoreus*) S protein, a *Streptococcus ictaluri* (*S. ictaluri*) S protein, a *Streptococcus didelphis* (*S. didelphis*) S protein, a *Streptococcus bovimastitidis* (*S. bovimastitidis*) S protein, a *Streptococcus penaeicida* (*S. penaeicida*) S protein, a *Streptococcus porcinus* (*S. porcinus*) S protein, a *Streptococcus pseudoporcinus* (*S. pseudoporcinus*) S protein, a *Streptococcus uberis* (*S. uberis*) S protein, a *Streptococcus iniae* (*S. iniae*) S protein, or a *Streptococcus parauberis* (*S. parauberis*) S protein.

In some embodiments, the *Streptococcus* S protein comprises, or consists essentially of, or yet further consists of one or more of:

```
                                          (SEQ ID NO: 1)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEGTG
ETLTVLAGEGAASIAARAGISVEQLQALNPEHMTQGYWYANPGDQVTIK;

                         (NCBI WP_136243812.1, SEQ ID NO: 2)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSTEETLASSEGTG
ETLTVLAGEGAASIAARAGISVEQLQALNPEHMTQGYWYANPGDQVTIK;

                         (NCBI WP_047235876.1, SEQ ID NO: 3)
MAKEPWEEKIVDDTIGTRTRKSRNAFISTPWLTALLSVFFVIIVAILFIFF
YTSNSGSNRQAETNGFYGASTHKKTKKASNAKKTSSSSTTTDTTPSSEETLASSEGTG
ETLTVLAGEGAASIAARAGISVEQLQALNPEHMTQGYWYANPGDQVTIK;

                         (NCBI WP_136301118.1, SEQ ID NO: 4)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEGTG
ETLTVLAGEGAASIAARSGISVEQLQALNPEHMTQGYWYANPGDQVTIK;

                         (NCBI WP_136112874.1, SEQ ID NO: 5)
MAKEPWEEKIVDDTIGTRTRKSRNAFISTPWLTALLSVFFVIIVAILFIFF
YTSNSGSNRQAETNGFYGASTHKKTRKASNAQKTSSSSTTTDTTPSSEETLASSEGTG
ETLTVLAGEGAASIAARAGISVEQLQALNPEHMTQGYWYANPGDQVTIK;

                         (NCBI WP_011284672.1, SEQ ID NO: 6)
MAKEPWEEKIVDDTIGTRTRKSRNAFISTPWLTALLSVFFVIIVAILFIFF
YTSNSGSNRQAETNGFYGASTHKKTRKASNAKKASSSSTTTDTTPSSEETLASSEGTG
ETLTVLAGEGAASIAARAGISVEQLQALNPEHMTQGYWYANPGDQVTIK;

                         (NCBI WP_136265537.1, SEQ ID NO: 7)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEEALASSEGTG
ETLTVLAGEGAASIAARAGISVEQLQALNPEHMTQGYWYANPGDQVTIK;

                         (NCBI WP_136112769.1, SEQ ID NO: 8)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEGTG
ETLTVLVGEGAASIAARAGISVEQLQALNPEHMTQGYWYANPGDQVTIK;
```

-continued (NCBI WP_136119095.1, SEQ ID NO: 9)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEGTG
KTLTVLAGEGAASIAARAGISVEQLQALNPEHMTQGYWYANPGDQVTIK;

(NCBI WP_136118039.1, SEQ ID NO: 10)
MAKEPWEEKIVDDTIGTRTRKSRNAFISTPWLTALLSVFFVIIVAILFIFF
YTSNSGSNRQTETNGFYGASTHKKTRKASNAKKTSSSSTTTDTTPSSEETLASSEGTG
ETLTVLAGEGAASIAARAGISVEQLQALNPEHMTQGYWYANPGDQVTIK;

(NCBI WP_136106171.1, SEQ ID NO: 11)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEGTG
ETLTVLAGEGGASIAARAGISVEQLQALNPEHMTQGYWYANPGDQVTIK;

(NCBI WP_136097276.1, SEQ ID NO: 12)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEGTG
ENLTVLAGEGAASIAARAGISVEQLQALNPEHMTQGYWYANPGDQVTIK;

(NCBI WP_030126737.1, SEQ ID NO: 13)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTKPSSEETLASSEGTG
ETLTVLAGEGAASIAARAGISVEQLQALNPEHMTQGYWYANPGDQVTIK;

(NCBI WP_136262681.1, SEQ ID NO: 14)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDITPSSEETLASSEGTG
ETLTVLAGEGAASIAARAGISVEQLQALNPEHMTQGYWYANPGDQVTIK;

(NCBI WP_023610847.1, SEQ ID NO: 15)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEGTG
ETLTVLAGEGAASIAARAGISVEQLQALNPEHMTQGYWYANPGDQVIIK;

(NCBI WP_002985156.1, SEQ ID NO: 16)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEEILASSEGTG
ETLTVLAGEGAASIAARAGISVEQLQALNPEHMTQGYWYANPGDQVTIK;

(NCBI WP_136302375.1, SEQ ID NO: 17)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEGTG
ETLTVLAGEGAASIAARAGISVEQLQALNPEHMTQGYWYANPGDHVTIK;

(NCBI WP_136108835.1, SEQ ID NO: 18)
MAKEPWEEKIVDDTIGTRTRKSRNAFISTPWLTALLSVFFVIIVAILFIFF
YTSNSGSNRQAETNGFYGASTHKKTRKASNAKKTSSSLTTTDTTPSSEETLASSEGTG
ETLTVLAGEGAASIAARAGISVEQLQALNPEHMTQGYWYANPGDQVTIK;

(NCBI WP_023612849.1, SEQ ID NO: 19);
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEETG
ETLTVLAGEGAASIAARAGISVEQLQALNPEHMTQGYWYANPGDQVTIK (NCBI WP_129821052.1, SEQ ID NO: 20)
MAKEPWEERIVDDTIGTRTRKSRNAFISTPWLTALLSVFFVIIVAILFIFF
YTSNSGSNRQAETNGFYGASTHKKTRKASNAKKASSSSTTTDTTPSSEETLASSEGTG
ETLTVLAGEGAASIAARAGISVEQLQALNPEHMTQGYWYANPGDQVTIK;

(NCBI WP_014635394.1, SEQ ID NO: 21)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEGTG
ETITVLAGEGAASIAARAGISVEQLQALNPEHMTQGYWYANPGDQVIIK;

(NCBI WP_129322007.1, SEQ ID NO: 22);
MAKEPWEEKNVDDTIGTRTRKSRNAFISTPWLTALLSVFFVIIVAILFIF
FYTSNSGSNRQAETNGFYGASTHKKTRKASNAKKTSSSSTTTDTTPSSEETLASSEGT
GETLTVLAGEGAASIAARAGISVEQLQALNPEHMTQGYWYANPGDQVTIK (NCBI WP_136076970.1, SEQ ID NO: 23)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEGTG
ETLTVLAGEGAASIAARAGISVGQLQALNPEHMTQGYWYANPGDQVTIK;

(NCBI WP_047235353.1, SEQ ID NO: 24)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEVTG
ETLTVLAGEGAASIAARAGISVEQLQALNPEHMTQGYWYANPGDQVTIK;

-continued (NCBI WP_136271947.1, SEQ ID NO: 25)
MAKEPWEEKIVDDTIGTRTRKSRNAFISTPWLTALLSVFFVIIVAILFIFF
YTSNSGSNRQAETNGFYGASTHKKARKASNAKKASSSSTTTDTTPSSEETLASSEGT
GETLTVLAGEGAASIAARAGISVEQLQALNPEHMTQGYWYANPGDQVTIK;

(NCBI WP_111704255.1, SEQ ID NO: 26)
MAKEPWEEKIVGDTIGTRTRKSRNAFISTPWLTALLSVFFVIIVAILFIFF
YTSNSGSNRQAETNGFYGASTHKKTRKASNAKKTSSSSTTTDTTPSSEETLASSEGTG
ETLTVLAGEGAASIAARAGISVEQLQALNPEHMTQGYWYANPGDQVTIK;

(NCBI WP_136085459.1, SEQ ID NO: 27)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEGTA
ETLTVLAGEGAASIAARAGISVEQLQALNPEHMTQGYWYANPGDQVIIK;

(NCBI WP_136277889.1, SEQ ID NO: 28)
MAKEPWEEKIVDDTIGTRTRKSRNAFISTPWLTALLSVFFVIIVAILFIFF
YTSNSGSNRQAETNGFYGASTHKKTRKASNAKKTSSSSTTIDTKPSSEETLASSEGTG
ETLTVLAGEGAASIAARAGISVEQLQALNPEHMTQGYWYANPGDQVTIK;

(NCBI WP_136094673.1, SEQ ID NO: 29)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEVTG
ETITVLAGEGAASIAARAGISVEQLQALNPEHMTQGYWYANPGDQVTIK;

(NCBI WP_136282593.1, SEQ ID NO: 30)
MAKEPWEEKIVDDTIGTRTRKSRNAFISTPWLTALLSVFFVIIVAILFIFF
YTSNSGSNRQAETNGFYGASTHKKTRKASNAKKISSSSTTTDTTPSSEETLASSEGTG
ETITVLAGEGAASIAARAGISVEQLQALNPEHMTQGYWYANPGDQVIIK;

(NCBI WP_136262155.1, SEQ ID NO: 31)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLTSSEGTG
ETITVLAGEGAASIAARAGISVEQLQALNPEHMTQGYWYANPGDQVIIK;

(NCBI WP_136288547.1, SEQ ID NO: 32)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEVTG
ETLTVLAGEGAASIAARAGISVEQLQALNPEHMTQGYWYANPGDQVIIK;

(NCBI WP_136114700.1, SEQ ID NO: 33)
MAKEPWEEKNVDDTIGTRTRKSRNAFISTPWLTALLSVFFVIIVAILFIF
FYTSNSGSNRQAETNGFYGASTHKKTRKASNAKKTSSSSTTTDTTPSSEETLASSEGT
GETLTVLAGEGAASIAARAGISVEQLQALNPEHMIQGYWYANPGDQVTIK;

(NCBI WP_002992564.1, SEQ ID NO: 34)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEVTG
ETITVLAGEGAASIAARAGISVEQLQALNPEHMTQGYWYANPGDQVIIK;

(NCBI WP_136037830.1, SEQ ID NO: 35)
MAKEPWEEKIIDDTIGTRTRKSRNAFISTPWLTALLSVFFVIIVAILFIFF
YTSNSGSNRQAETNGFYGASTHKKTRKASNAKKTSSSSTTTDTTPSSEETLASSEVTG
ETITVLAGEGAASIAARAGISVEQLQALNPEHMTQGYWYANPGDQVIIK;

(NCBI WP_136276760.1, SEQ ID NO: 36)
MAKEPWEEKIVDDTIGTRTRKSRNAFISTPWMTALLSVFFVIIVAILFIF
FYTSNSGSNRQAETNGFYGASTHKKTRKASNAKKTSSSSTTTDTTPSSEETLASSEVT
GETITVLAGEGAASIAARAGISVEQLQALNPEHMTQGYWYANPGDQVIIK;

(NCBI WP_085600270.1, SEQ ID NO: 37)
MAKEPWEEKIVDDTIGTRTRKSRNAFISTPWLTALLSVFFVIIVAILFIFF
YTSNSGSNRQAETNGFYGASTHKKTRKASNAKKTSSSSTTTDTTPSSEETLASSEVTG
ETITVLAGEGAASIAARAGISVEQLQALNPEHMIQGYWYANPGDQVIIK;

or an equivalent of each thereof.

In some embodiments, the *Streptococcus* S protein comprises, or consists essentially of, or yet further consists of MAKEPWEEXXXXDTIGTRTRKSRNAFISTPWX-TALLSVFFVIIVAILFIFFYTSNSGSN RQXETNGFY-GASTHKKXXKASNAXKXSSSXTTXDXXPSXE-EXLXSSEXTXXXXTVL XGEGXASIAARXGISVX-QLQALNPEHMXQGYWYANPGDXVXIK, wherein X is any amino acid residue or the corresponding amino acid residue in any one of SEQ ID Nos: 1-37 (SEQ ID NO: 38) or an equivalent thereof.

In some embodiments, the equivalent comprises at least about 60% (including but not limited to at least about 70%, or at least about 75%, or at least about 80%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% or higher) identity to the *Streptococcus* S protein. In further embodiments, the identity was calculated via comparing to the full length of the S protein. Alternatively, the identity was calculated via comparing to at least 70% (including but not limited to at least about 75%, or at least about 80%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% or higher) of the full length of the protein.

In some embodiments, the equivalent further comprises at least one post-transcriptional modification selected from deamidation, oxidation, dioxidation, formylation, carboxylation, carbamylation, or glycosylation.

In some embodiments, the equivalent further comprises an immunogenic fragment of the *Streptococcus* S protein. In some embodiments, the immunogenic fragment is located in the conserved region of the consensus sequence of SEQ ID NO: 38.

In some embodiments, the equivalent of a reference S protein can induce an immune response to an S protein or a *Streptococcus*, such as a GAS. In further embodiments, the equivalent of a reference S protein can induce an immune response to an S protein or a *Streptococcus*, such as a GAS at a level significantly similar to the reference S protein. Non-limiting assays for evaluating the induced immune response are provided in the Examples.

In some embodiments, the *Streptococcus* S protein or an equivalent thereof further comprises a detectable or a purification marker.

In some embodiments, the method further comprises administering an adjuvant to the subject. In further embodiments, the adjuvant comprises, or consist essentially of, or yet further consists of an aluminum hydroxide adjuvant. In yet further embodiments, the ratio of the *Streptococcus* S protein to the adjuvant is about 10:1 to about 1:30, or any ranges or ration therebetween, optionally about 1:3.

In some embodiments, the one or more of the S protein of (i), the polynucleotide of (ii), or the vector of (iii) are administered in a composition further comprising a carrier. In further embodiments, the carrier comprises, or consists essentially of, or yet further consist of one or more of: a preservative, a stabilizer, or an adjuvant.

In some embodiments, the method further comprises administering a therapy for treating a *Streptococcus* infection to the subject. In further embodiments, the therapy comprises, or consists essentially of, or yet further consists of a combination therapy as disclosed herein, such as an antibiotic.

In some embodiments, the method further comprises administering an immunogenic antigen of a pathogen other than *Streptococcus* or GAS to the subject, such as an Adenovirus vaccine, an Anthrax vaccine (e.g., AVA (BioThrax)), a Cholera vaccine (e.g., Vaxchora), a Diphtheria vaccine (e.g., DTaP (Daptacel, Infanrix), Td (Tenivac, generic), DT (-generic-), Tdap (Adacel, Boostrix), DTaP-IPV (Kinrix, Quadracel), DTaP-HepB-IPV (Pediarix), or DTaP-IPV/Hib (Pentacel)), a Hepatitis A vaccine (e.g., HepA (Havrix, Vaqta) or HepA-HepB (Twinrix)), a Hepatitis B vaccine (e.g., HepB (Engerix-B, Recombivax HB, Heplisav-B), DTaP-HepB-IPV (Pediarix), or HepA-HepB (Twinrix)), a *Haemophilus influenzae* type b (Hib) vaccine (e.g., Hib (ActHIB, PedvaxHIB, Hiberix) or DTaP-IPV/Hib (Pentacel)), a Human Papillomavirus (HPV) vaccine (e.g., HPV9 (Gardasil 9)), a seasonal Influenza (Flu) vaccine (such as IIV* (Afluria, Fluad, Flublok, Flucelvax, FluLaval, Fluarix, Fluvirin, Fluzone, Fluzone High-Dose, Fluzone Intradermal) or LAIV (FluMist)), a Japanese Encephalitis vaccine (e.g., JE (Ixiaro)), a Measles vaccine (e.g., MMR (M-M-R II) or MMRV (ProQuad)), a Meningococcal vaccine (e.g., MenACWY (Menactra, Menveo) or MenB (Bexsero, Trumenba)), a Mumps vaccine (e.g., MMR (M-M-R II) or MMRV (ProQuad)), a Pertussis vaccine (e.g., DTaP (Daptacel, Infanrix), Tdap (Adacel, Boostrix), DTaP-IPV (Kinrix, Quadracel), DTaP-HepB-IPV (Pediarix), or DTaP-IPV/Hib (Pentacel)), a Pneumococcal vaccine (e.g., PCV13 (Prevnar13) or PPSV23 (Pneumovax 23)), a Polio vaccine (e.g., Polio (Ipol), DTaP-IPV (Kinrix, Quadracel), DTaP-HepB-IPV (Pediarix), or DTaP-IPV/Hib (Pentacel)), a Rabies vaccine (e.g., Rabies (Imovax Rabies, RabAvert)), a Rotavirus vaccine (e.g., RV1 (Rotarix) or RV5 (RotaTeq)), a Rubella vaccine (e.g., MMR (M-M-R II), or MMRV (ProQuad)), a Shingles vaccine (e.g., RZV (Shingrix)), a Smallpox vaccine (e.g., Vaccinia (ACAM2000)), a Tetanus vaccine (e.g., DTaP (Daptacel, Infanrix), Td (Tenivac, generic), DT (-generic-), Tdap (Adacel, Boostrix), DTaP-IPV (Kinrix, Quadracel), DTaP-HepB-IPV (Pediarix), or DTaP-IPV/Hib (Pentacel)), a Tuberculosis vaccine, a Typhoid Fever vaccine (Typhoid Oral (Vivotif) or Typhoid Polysaccharide (Typhim Vi)), a Varicella vaccine (e.g., VAR (Varivax) or MMRV (ProQuad)), or a Yellow Fever vaccine (e.g., YF (YF-Vax)).

In some embodiments, the S protein or polynucleotide or the vector or the composition is lyophilized.

In some embodiments, the administration is repeated for at least once, or at least twice, or at least three times, or at least four times, or at least five times, or at least six times, or at least seven times, or at least eight times, or at least nine times, or at least ten times, or more.

In further embodiments, any two administrations are about 1 day apart, or about 3 days apart, or about 5 days apart, or about 7 days apart, or about 8 days apart, or about 9 days apart, or about 10 days apart, or about 11 days apart, or about 12 days apart, or about 13 days apart, or about 14 days apart, or about 15 days apart, or about 16 days apart, or about 17 days apart, or about 18 days apart, or about 19 days apart, or about 20 days apart, or about 21 days apart, or about 22 days apart, or about 23 days apart, or about 24 days apart, or about 25 days apart, or about 26 days apart, or about 27 days apart, or about 28 days apart, or about 29 days apart, or about 30 days apart, or about 31 days apart, or about 32 days apart, or about 33 days apart, or about 34 days apart, or about 35 days apart, or about 36 days apart, or about 37 days apart, or about 38 days apart, or about 39 days apart, or about 40 days apart, or about 41 days apart, or about 42 days apart, or about 2 months apart, or about 3 months apart, or about 4 months apart, or about 5 months apart, or about 6 months apart, or about 7 months apart, or about 8 months apart, or about 9 months apart, or about 10 months apart, or about 11 months apart, or about 12 months apart, or longer.

In some embodiments, the subject has been infected by or has a high risk of being infected by *Streptococcus*. In further embodiments, the *Streptococcus* infection is a GAS infection or a GBS infection.

In one aspect, provided is a method for conferring a passive immunity to a subject in need thereof without inducing an autoimmune sequelae. The method comprises, or consists essentially of, or yet further consists of administering an antibody or an antigen binding fragment thereof specifically recognizing and binding a *Streptococcus* S protein or an equivalent thereof, thereby conferring the passive immunity to *Streptococcus* in the subject without inducing an autoimmune sequelae.

In another aspect, provided is a method for conferring a passive immunity to a subject in need thereof. The method comprises, or consists thereof, or yet further consists of administering an antibody or an antigen binding fragment thereof specifically recognizing and binding a *Streptococcus* S protein or an equivalent thereof. In some embodiments, the method confers the passive immunity to *Streptococcus* in the subject. In further embodiments, the method does not induce an autoimmune sequelae.

In some embodiments, the administration is repeated for at least once, or at least twice, or at least three times, or at least four times, or at least five times, or at least six times, or at least seven times, or at least eight times, or at least nine times, or at least ten times, or more.

In further embodiments, any two administrations are about 1 day apart, or about 3 days apart, or about 5 days apart, or about 7 days apart, or about 8 days apart, or about 9 days apart, or about 10 days apart, or about 11 days apart, or about 12 days apart, or about 13 days apart, or about 14 days apart, or about 15 days apart, or about 16 days apart, or about 17 days apart, or about 18 days apart, or about 19 days apart, or about 20 days apart, or about 21 days apart, or about 22 days apart, or about 23 days apart, or about 24 days apart, or about 25 days apart, or about 26 days apart, or about 27 days apart, or about 28 days apart, or about 29 days apart, or about 30 days apart, or about 31 days apart, or about 32 days apart, or about 33 days apart, or about 34 days apart, or about 35 days apart, or about 36 days apart, or about 37 days apart, or about 38 days apart, or about 39 days apart, or about 40 days apart, or about 41 days apart, or about 42 days apart, or about 2 months apart, or about 3 months apart, or about 4 months apart, or about 5 months apart, or about 6 months apart, or about 7 months apart, or about 8 months apart, or about 9 months apart, or about 10 months apart, or about 11 months apart, or about 12 months apart, or longer.

In some embodiments, the subject has been infected by or has a high risk of being infected by *Streptococcus*. In further embodiments, the *Streptococcus* infection is a GAS infection or a GBS infection.

In one aspect, provided is a vaccine composition comprising, or consisting essentially of, or yet further consisting of a carrier and one or more of: (i) a *Streptococcus* S protein or an equivalent thereof, (ii) a polynucleotide encoding the protein or equivalent of (i), or a complementary polynucleotide thereto, or (iii) a vector comprising the polynucleotide of (ii). In some embodiments, the S protein, or the polynucleotide, or the vector is isolated, for example from a cell producing the S protein, the polynucleotide or the vector. Additionally or alternatively, the S protein or the polynucleotide or the vector is engineered.

In some embodiments, the S protein comprises, or consists essentially of, or yet further consists of a Group A *Streptococcus* (GAS) S protein. In further embodiments, the GAS comprises, or consists essentially of, or yet further consists of *Streptococcus pyogenes* (*S. pyogenes*).

In some embodiments, the S protein comprises, or consists essentially of, or yet further consists of a Group B *Streptococcus* (GBS) S protein. In further embodiments, the GBS comprises, or consists essentially of, or yet further consists of *Streptococcus agalactiae* (*S. agalactiae*).

In some embodiments, the *Streptococcus* is selected from the group consisting of *Streptococcus equi* (*S. equi*), *Streptococcus dysgalactiae* (*S. dysgalactiae*), *Streptococcus canis* (*S. canis*), *Streptococcus phocae* (*S. phocae*), *Streptococcus castoreus* (*S. castoreus*), *Streptococcus ictaluri* (*S. ictaluri*), *Streptococcus didelphis* (*S. didelphis*), *Streptococcus bovimastitidis* (*S. bovimastitidis*), *Streptococcus penaeicida* (*S. penaeicida*), *Streptococcus porcinus* (*S. porcinus*), *Streptococcus pseudoporcinus* (*S. pseudoporcinus*), *Streptococcus uberis* (*S. uberis*), *Streptococcus iniae* (*S. iniae*), or *Streptococcus parauberis* (*S. parauberis*).

Additionally or alternatively, the *Streptococcus* S protein comprises, or consists essentially of, or yet further consists of one or more of: a *Streptococcus equi* (*S. equi*) S protein, a *Streptococcus dysgalactiae* (*S. dysgalactiae*) S protein, a *Streptococcus canis* (*S. canis*) S protein, a *Streptococcus phocae* (*S. phocae*) S protein, a *Streptococcus castoreus* (*S. castoreus*) S protein, a *Streptococcus ictaluri* (*S. ictaluri*) S protein, a *Streptococcus didelphis* (*S. didelphis*) S protein, a *Streptococcus bovimastitidis* (*S. bovimastitidis*) S protein, a *Streptococcus penaeicida* (*S. penaeicida*) S protein, a *Streptococcus porcinus* (*S. porcinus*) S protein, a *Streptococcus pseudoporcinus* (*S. pseudoporcinus*) S protein, a *Streptococcus uberis* (*S. uberis*) S protein, a *Streptococcus iniae* (*S. iniae*) S protein, or a *Streptococcus parauberis* (*S. parauberis*) S protein.

In some embodiments, the *Streptococcus* S protein comprises, or consists essentially of, or yet further consists of one or more of: SEQ ID Nos: 1-37 or an equivalent of each thereof.

In some embodiments, the *Streptococcus* S protein comprises, or consists essentially of, or yet further consists of MAKEPWEEXXXXDTIGTRTRKSRNAFISTPWX-TALLSVFFVIIVAILFIFFYTSNSGSN RQXETNGFY-GASTHKKXXXKASNAXKXSSSXTTXDXXPSXE-EXLXSSEXTXXXXTVL XGEGXASIAARXGISVXQ-LQALNPEHMXQGYWYANPGDXVXIK, wherein X is any amino acid residue or the corresponding amino acid residue in any one of SEQ ID Nos: 1-37 (SEQ ID NO: 38) or an equivalent thereof.

In some embodiments, the equivalent comprises at least about 60% (including but not limited to at least about 70%, or at least about 75%, or at least about 80%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% or higher) identity to the *Streptococcus* S protein. In further embodiments, the identity was calculated via comparing to the full length of the S protein. Alternatively, the identity was calculated via comparing to at least 70% (including but not limited to at least about 75%, or at least about 80%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% or higher) of the full length of the protein.

In some embodiments, the equivalent further comprises at least one post-transcriptional modification selected from deamidation, oxidation, dioxidation, formylation, carboxylation, carbamylation, or glycosylation.

In some embodiments, the equivalent further comprises an immunogenic fragment of the *Streptococcus* S protein. In some embodiments, the immunogenic fragment is located in the conserved region of the consensus sequence of SEQ ID NO: 38.

In some embodiments, the equivalent of a reference S protein can induce an immune response to an S protein or a *Streptococcus*, such as a GAS. In further embodiments, the equivalent of a reference S protein can induce an immune response to an S protein or a *Streptococcus*, such as a GAS at a level significantly similar to the reference S protein.

Non-limiting assays for evaluating the induced immune response are provided in the Examples.

In some embodiments, the *Streptococcus* S protein or an equivalent thereof further comprises a detectable or a purification marker.

In some embodiments, the carrier comprises, or consists essentially of, or yet further consists of an adjuvant. In further embodiments, the adjuvant comprises, or consists essentially of, or yet further consists of an aluminum hydroxide adjuvant. In some embodiments, the ratio of the *Streptococcus* S protein to the adjuvant is about 10:1 to about 1:30, or any ranges or ratio therebetween, optionally about 1:3. In further embodiments, the ratio is a molar ratio. In other embodiments, the ratio is a weight ratio.

In some embodiments, the carrier further comprises a preservative, or a stabilizer, or both.

In some embodiments, the vaccine composition further comprises a therapy for treating a *Streptococcus* infection. In further embodiments, the therapy comprises an antibiotic.

In some embodiments, the vaccine composition further comprises an immunogenic antigen of a pathogen other than *Streptococcus* or GAS, such as an Adenovirus vaccine, an Anthrax vaccine (e.g., AVA (BioThrax)), a Cholera vaccine (e.g., Vaxchora), a Diphtheria vaccine (e.g., DTaP (Daptacel, Infanrix), Td (Tenivac, generic), DT (-generic-), Tdap (Adacel, Boostrix), DTaP-IPV (Kinrix, Quadracel), DTaP-HepB-IPV (Pediarix), or DTaP-IPV/Hib (Pentacel)), a Hepatitis A vaccine (e.g., HepA (Havrix, Vaqta) or HepA-HepB (Twinrix)), a Hepatitis B vaccine (e.g., HepB (Engerix-B, Recombivax HB, Heplisav-B), DTaP-HepB-IPV (Pediarix), or HepA-HepB (Twinrix)), a *Haemophilus influenzae* type b (Hib) vaccine (e.g., Hib (ActHIB, PedvaxHIB, Hiberix) or DTaP-IPV/Hib (Pentacel)), a Human Papillomavirus (HPV) vaccine (e.g., HPV9 (Gardasil 9)), a seasonal Influenza (Flu) vaccine (such as IIV* (Afluria, Fluad, Flublok, Flucelvax, FluLaval, Fluarix, Fluvirin, Fluzone, Fluzone High-Dose, Fluzone Intradermal) or LAIV (FluMist)), a Japanese Encephalitis vaccine (e.g., JE (Ixiaro)), a Measles vaccine (e.g., MMR (M-M-R II) or MMRV (ProQuad)), a Meningococcal vaccine (e.g., MenACWY (Menactra, Menveo) or MenB (Bexsero, Trumenba)), a Mumps vaccine (e.g., MMR (M-M-R II) or MMRV (ProQuad)), a Pertussis vaccine (e.g., DTaP (Daptacel, Infanrix), Tdap (Adacel, Boostrix), DTaP-IPV (Kinrix, Quadracel), DTaP-HepB-IPV (Pediarix), or DTaP-IPV/Hib (Pentacel)), a Pneumococcal vaccine (e.g., PCV13 (Prevnar13) or PPSV23 (Pneumovax 23)), a Polio vaccine (e.g., Polio (Ipol), DTaP-IPV (Kinrix, Quadracel), DTaP-HepB-IPV (Pediarix), or DTaP-IPV/Hib (Pentacel)), a Rabies vaccine (e.g., Rabies (Imovax Rabies, RabAvert)), a Rotavirus vaccine (e.g., RV1 (Rotarix) or RV5 (RotaTeq)), a Rubella vaccine (e.g., MMR (M-M-R II), or MMRV (ProQuad)), a Shingles vaccine (e.g., RZV (Shingrix)), a Smallpox vaccine (e.g., Vaccinia (ACAM2000)), a Tetanus vaccine (e.g., DTaP (Daptacel, Infanrix), Td (Tenivac, generic), DT (-generic-), Tdap (Adacel, Boostrix), DTaP-IPV (Kinrix, Quadracel), DTaP-HepB-IPV (Pediarix), or DTaP-IPV/Hib (Pentacel)), a Tuberculosis vaccine, a Typhoid Fever vaccine (Typhoid Oral (Vivotif) or Typhoid Polysaccharide (Typhim Vi)), a Varicella vaccine (e.g., VAR (Varivax) or MMRV (ProQuad)), or a Yellow Fever vaccine (e.g., YF (YF-Vax)).

In some embodiments, the composition is lyophilized.

In some embodiments, the composition is for use in a method as disclosed herein.

This disclosure provides compositions and methods of eliciting in an individual an immune response and/or prevent or treat an infection associated with a GAS infection, e.g., *S. pyogenes*. In certain aspects, the methods elicit an immune response to the proteins of the invention. These methods elicit one or more immune responses, including but not limited to, immune responses which provide the therapeutic responses disclosed herein. In one embodiment, the methods comprise a step of administering an immunogenic dose of a composition as described herein. The methods may be used prior or subsequent to infection of an individual harboring an infection. The methods and compositions of the disclosure can also be used to treat or prevent any pathological condition associated with a GAS infection, e.g. *S. pyogenes*, e.g., scarlet fever, necrotizing fasciitis, bacteremia, pneumonia, Streptococcal Toxic Shock Syndrome (STSS), and rheumatic heart disease.

In one aspect, one or more compositions of the disclosure is administered as a priming dose followed by one or more booster doses. Co-administration of proteins or polypeptides that beneficially enhance the immune response such as cytokines (e.g., IL-2, IL-12, GM-CSF), cytokine-inducing molecules (e.g. Leaf) or co-stimulatory molecules is also contemplated.

An “immunogenic dose” of a composition of the invention is one that generates, after administration, a detectable humoral (antibody) and/or cellular (T cell) immune response in comparison to the immune response detectable before administration or in comparison to a standard immune response before administration. The invention contemplates that the immune response resulting from the methods may be protective and/or therapeutic. The precise dose depends on the patient’s state of health and weight, the mode of administration, the nature of the formulation, etc., but generally ranges from about 1.0 microgram to about 5000 microgram per 70 kilogram patient, more commonly from about 10 to about 500 microgram per 70 kg of body weight.

Humoral immune response may be measured by many well-known methods, such as Single Radial Immunodiffusion Assay (SRID), Enzyme Immunoassay (ETA) and Hemagglutination Inhibition Assay (HAI). In particular, SRID utilizes a layer of a gel, such as agarose, containing the immunogen being tested. A well is cut in the gel and the serum being tested is placed in the well. Diffusion of the antibody out into the gel leads to the formation of a precipitation ring whose area is proportional to the concentration of the antibody in the serum being tested. EIA, also known as ELISA (Enzyme Linked Immunoassay), is used to determine total antibodies in the sample. The immunogen is adsorbed to the surface of a microtiter plate. The test serum is exposed to the plate followed by an enzyme linked immunoglobulin, such as IgG. The enzyme activity adherent to the plate is quantified by any convenient means such as spectrophotometry and is proportional to the concentration of antibody directed against the immunogen present in the test sample. HAI utilizes the capability of an immunogen such as viral proteins to agglutinate chicken red blood cells (or the like). The assay detects neutralizing antibodies, i.e., those antibodies able to inhibit hemagglutination. Dilutions of the test serum are incubated with a standard concentration of immunogen, followed by the addition of the red blood cells. The presence of neutralizing antibodies will inhibit the agglutination of the red blood cells by the immunogen. Tests to measure cellular immune response include determination of delayed-type hypersensitivity or measuring the proliferative response of lymphocytes to target immunogen.

Thus, in one aspect, the disclosure provides compositions suitable for eliciting an immune response to the S protein. The compositions may also comprise other ingredients such as carriers and adjuvants.

In compositions of the disclosure, an S protein of this disclosure can be fused to another protein when produced by recombinant methods. In one embodiment, the other protein may not, by itself, elicit antibodies, but it stabilizes the first protein and fauns a fusion protein retaining immunogenic activity. In another embodiment, the fusion protein comprises another protein that is immunogenic, such as Glutathione-S-transferase (GST) or beta-galactosidase, relatively large co-proteins which solubilize the fusion protein and facilitate production and purification thereof. The other protein may act as an adjuvant in the sense of providing a generalized stimulation of the immune system. The other protein may be fused to either the amino or carboxy terminus of the chimeric proteins as disclosed herein.

In sum aspects, the S protein can be linked to carrier substances. Any method of creating such linkages known in the art may be used. Linkages can be formed with hetero-bifunctional agents that generate a disulfide link at one functional group end and a peptide link at the other, such as a disulfide amide forming agent, e.g., N-succinimidyl-3-(2-pyridyldithio) proprionate (SPDP) (See, e.g., Jansen et al., Immun. Rev. 62:185, 1982) and bifunctional coupling agents that form a thioether rather than a disulfide linkage such as reactive esters of 6-maleimidocaproic acid, 2-bromoacetic acid, 2-iodoacetic acid, 4-(N-maleimido-methyl) cyclohexane-1-carboxylic acid and the like, and coupling agent which activate carboxyl groups by combining them with succinimide or 1-hydroxy-2-nitro-4-sulfonic acid, for sodium salt such as succinimidyl 4-(N-maleimido-methyl) cyclohexane-1-carboxylate (SMCC).

The S protein can be formulated as neutral or salt forms. Pharmaceutically acceptable salts, include the acid addition salts (formed with the free amino groups of the peptide) and which are formed with inorganic acids such as, e.g., hydrochloric or phosphoric acids, or such organic acids as acetic, oxalic, tartaric, mandelic. Salts formed with the free carboxyl groups may also be derived from inorganic bases such as, e.g., sodium, potassium, ammonium, calcium, or ferric hydroxides, and such organic bases as isopropylamine, trimethylamine, 2-ethylamino ethanol, histidine, and procaine.

The compositions of this disclosure can further comprise adjuvants. Known adjuvants include, for example, emulsions such as Freund's Adjuvants and other oil emulsions, *Bordetella pertussis*, MF59, purified saponin from *Quillaja saponaria* (QS21), aluminum salts such as hydroxide, phosphate and alum, calcium phosphate, (and other metal salts), gels such as aluminum hydroxide salts, mycobacterial products including muramyl dipeptides, solid materials, particles such as liposomes and virosomes. Examples of natural and bacterial products known to be used as adjuvants include monophosphoryl lipid A (MPL), RC-529 (synthetic MPL-like acylated monosaccharide), OM-174 which is a lipid A derivative from *E. coli*, holotoxins such as cholera toxin (CT) or one of its derivatives, pertussis toxin (PT) and heat-labile toxin (LT) of *E. coli* or one of its derivatives, and CpG oligonucleotides. Adjuvant activity can be affected by a number of factors, such as carrier effect, depot formation, altered lymphocyte recirculation, stimulation of T-lymphocytes, direct stimulation of B-lymphocytes and stimulation of macrophages.

The compositions of the disclosure are typically formulated as injectables, either as liquid solutions or suspensions; solid forms suitable for solution in, or suspension in, liquid prior to injection may also be prepared. The preparation may also be emulsified. The active immunogenic ingredient is often mixed with excipients, which are pharmaceutically acceptable and compatible with the active ingredient. Suitable excipients are, e.g., water, saline, dextrose, glycerol, ethanol, or the like and combinations thereof. In addition, if desired, the vaccine may contain minor amounts of auxiliary substances such as wetting or emulsifying agents, pH buffering agents, or adjuvants, which enhance the effectiveness of the vaccine. The vaccines are conventionally administered parenterally, by injection, for example, either subcutaneously or intramuscularly.

Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10%-95% of active ingredient, preferably 25-70%.

Compositions may also be administered through transdermal routes utilizing jet injectors, microneedles, electroporation, sonoporation, microencapsulation, polymers or liposomes, transmucosal routes and intranasal routes using nebulizers, aerosols and nasal sprays. Microencapsulation using natural or synthetic polymers such as starch, alginate and chitosan, D-poly L-lactate (PLA), D-poly DL-lactic-coglycolic microspheres, polycaprolactones, polyorthoesters, polyanhydrides and polyphosphazenes polyphosphatazanes are useful for both transdermal and transmucosal administration. Polymeric complexes comprising synthetic poly-ornithine, poly-lysine and poly-arginine or amphipathic peptides are useful for transdermal delivery systems. In addition, due to their amphipathic nature, liposomes are contemplated for transdermal, transmucosal and intranasal vaccine delivery systems. Common lipids used for vaccine delivery include N-(1)2,3-(dioleyl-dihydroxypropyl)-N,N,N,-trimethylammonium-methyl sulfate (DOTAP), dioleyloxy-propyl-trimethylammonium chloride DOTMA, dimystyloxypropyl-3-dimethyl-hydroxyethyl ammonium (DMRIE), dimethyldioctadecyl ammonium bromide (DDAB) and 9N(N',N-dimethylaminoethane) carbamoyl) cholesterol (DC-Chol). The combination of helper lipids and liposomes will enhance up-take of the liposomes through the skin. These helper lipids include dioleoyl phosphatidylethanolamine (DOPE), dilauroylphosphatidylethanolamine (DLPE), dimyristoyl phosphatidylethanolamine (DMPE), dipalmitoylphosphatidylethanolamine (DPPE). In addition, triterpenoid glycosides or saponins derived from the Chilean soap tree bark (*Quillaja saponaria*) and chitosan (deacetylated chitan) have been contemplated as useful adjuvants for intranasal and transmucosal vaccine delivery.

Formulations can be presented in unit-dose or multi-dose containers, for example, sealed ampules and vials and may be stored in a freeze-dried condition requiring only the addition of the sterile liquid carrier immediately prior to use.

Combination Therapy

The compositions and related methods of the present disclosure may be used in combination with the administration of other therapies. These include, but are not limited to, the administration of antibiotics, antimicrobials, or other antibodies.

In other embodiments, the methods and compositions can be combined with antibiotics and/or antimicrobials. Antimicrobials are substances that kill or inhibit the growth of microorganisms such as bacteria, fungi, or protozoans. Some non-limiting examples of antimicrobials and antibiotics useful in combination with methods of the current disclosure include amoxicillin, amoxicillin-clavulanate, cefdinir, azithromycin, and sulfamethoxazole-trimethoprim. The therapeutically effective dose of the antimicrobial and/or antibiotic in combination with the agent can be readily determined by traditional methods. In some embodiments the dose of the antimicrobial agent in combination with the agent is the average effective dose which has been shown to be effective in other bacterial infections In other embodiments, the dose is 0.1, 0.15, 0.2, 0.25, 0.30, 0.35, 0.40, 0.45, 0.50, 0.55, 0.60, 0.65, 0.70, 0.75, 0.8, 0.85, 0.9, 0.95, 1.1, 1.2, 1.3, 1.4, 1.5, 1.6, 1.7, 1.8, 1.9, 2.0, 2.5, 3.0 or 5 times the average effective dose.

In other embodiments, the methods and compositions can be combined with antibodies that treat the bacterial infection.

The additional therapeutic treatment can be added prior to, concurrent with, or subsequent to methods or compositions, and can be contained within the same formation or as a separate formulation.

Formulations and Co-Formulations

The disclosure provided herein contemplates specific formulations and co-formulations of the agents disclosed herein along with a pharmaceutically acceptable excipient, such as those disclosed herein above.

In some embodiments, the S proteins, polynucleotides, vectors, antibodies or antigen binding fragments thereof are present in the formulation at a concentration from about 0.1 mg/mL to about 200 mg/mL, or alternatively from about 1 to about 150 mg/mL, or alternatively about 2 mg/mL to about 100 mg/mL, or alternatively about 3 mg/mL to about 80 mg/mL, or alternatively about 4 mg/mL to about 50 mg/mL, or alternatively about 5 mg/ml to about 20 mg/mL. In some embodiments, the S proteins, polynucleotides, vectors, antibodies or antigen binding fragments thereof are present at a concentration of at least about 1 mg/mL, or alternatively at least about 2 mg/mL, at least about 3 mg/mL, or alternatively at least about 4 mg/mL, or alternatively at least about 5 mg/mL, or alternatively at least about 6 mg/mL, or alternatively at least about 7 mg/mL, or alternatively at least about 8 mg/mL, or alternatively at least about 9 mg/mL, or alternatively at least about 10 mg/mL, or alternatively at least about 15 mg/mL, or alternatively at least about 20 mg/mL, or alternatively at least about 30 mg/mL, or alternatively at least about 40 mg/mL, or alternatively at least about 50 mg/mL, or alternatively at least about 60 mg/mL, or alternatively at least about 70 mg/mL, or alternatively at least about 80 mg/mL, or alternatively at least about 90 mg/mL, or alternatively at least about 100 mg/mL, or alternatively at least about 120 mg/mL, or alternatively at least about 150 mg/mL or alternatively at least about 200 mg/mL. In some embodiments, at least one of the S proteins, polynucleotides, vectors, antibodies or antigen binding fragments thereof is present at a concentration of at least about 1 mg/mL, or alternatively at least about 2 mg/mL, or alternatively at least about 3 mg/mL, or alternatively at least about 4 mg/mL, or alternatively at least about 5 mg/mL, or alternatively at least about 6 mg/mL, or alternatively at least about 7 mg/mL, or alternatively at least about 8 mg/mL, or alternatively at least about 9 mg/mL, or alternatively at least about 10 mg/mL, or alternatively at least about 15 mg/mL, or alternatively at least about 20 mg/mL, or alternatively at least about 30 mg/mL, or alternatively at least about 40 mg/mL, or alternatively at least about 50 mg/mL, or alternatively at least about 60 mg/mL, or alternatively at least about 70 mg/mL, or alternatively at least about 80 mg/mL, or alternatively at least about 90 mg/mL, or alternatively at least about 100 mg/mL, or alternatively at least about 120 mg/mL, or alternatively at least about 150 mg/mL, or alternatively at least about 200 mg/mL.

In some embodiments, wherein multiple different S proteins, polynucleotides, vectors, antibodies or antigen binding fragments thereof are included in a co-formulation, the different S proteins, polynucleotides, vectors, antibodies or antigen binding fragments thereof may be present in substantially equal concentrations. In another aspect of such embodiments, the different S protein, polynucleotide, vector, antibody or antigen binding fragment thereof may be present in a substantially higher concentration than the other S proteins, polynucleotides, vectors, antibodies or antigen binding fragments thereof, e.g., ratios of about 1.5:1, or alternatively about 1.5:1:1, or alternatively about 1.5:1:1:1, or alternatively about 2:1, or alternatively about 2:1:1, or alternatively about 2:1:1:1, or alternatively at least about 2.5:1, or alternatively at least about 2.5:1:1, or alternatively at least about 2.5:1:1:1.

Methods of stably formulating formulations and co-formulations can be made according to techniques disclosed in the art-see, e.g., U.S. Pat. Publication No. US 2011/0059079.

Kits

Additionally provided is a kit comprising, or consisting essentially of, or yet further consisting of a vaccine composition as disclosed herein and optionally instructions for use.

In one aspect, provided is a kit for use in a method as disclosed herein. The kit comprises, or consists essentially of, or yet further consists of a composition and optionally instructions for use. In some embodiments, the composition comprises, or consists essentially of, or yet further consists of one or more of: the S protein or equivalent of (i), the isolated polynucleotide of (ii), the vector of (iii) or the antibody or antigen binding fragment thereof.

In some embodiments, the kit further comprises an adjuvant. In further embodiments, the adjuvant comprises, or consists essentially of, or yet further consists of an aluminum hydroxide adjuvant. In some embodiments, the ratio of the *Streptococcus* S protein to the adjuvant is about 10:1 to about 1:30, or any range or ratio therebetween, optionally about 1:3.

In some embodiments, the kit further comprises a therapy for treating a *Streptococcus* infection. In further embodiments, the therapy comprises, or consists essentially of, or yet further consists of a combination therapy as disclosed herein, such as an antibiotic.

In some embodiments, the kit further comprises an immunogenic antigen of a pathogen other than *Streptococcus* or GAS, such as those as disclosed herein.

In some embodiments, the composition is a vaccine composition as disclosed herein.

In some embodiments, the composition further comprises a carrier. In further embodiments, the carrier comprises, or consists essentially of, or yet further consists of one or more of: a preservative, a stabilizer, or an adjuvant.

In some embodiments, the composition further comprises a therapy for treating a *Streptococcus* infection. In further embodiments, the therapy comprises, or consists essentially of, or yet further consists of a combination therapy as disclosed herein, such as an antibiotic.

In some embodiments, the composition further comprises an immunogenic antigen of a pathogen other than *Streptococcus* or GAS, such as those as disclosed herein.

Kits containing the agents and instructions necessary to perform the in vitro and in vivo methods as described herein also are claimed. Accordingly, the disclosure provides kits for performing these methods which may include an agent disclosed herein as well as instructions for carrying out the methods disclosed herein such as administration of an effective amount of an agent as defined herein. These can be used alone or in combination with other suitable antimicrobial agents.

For example, a kit can comprise, or alternatively consist essentially of, or yet further consist of any one or more agent identified above, e.g., an S protein or an equivalent thereof; an isolated or recombinant polynucleotide encoding the S protein or an equivalent thereof; a vector as disclosed herein; or an antibody or fragment thereof; and instructions for use. The kit can further comprise one or more of an adjuvant, an antigenic peptide or an antimicrobial. Examples of carriers include a liquid carrier, a pharmaceutically acceptable carrier, a solid phase carrier, a pharmaceutically acceptable carrier, a pharmaceutically acceptable polymer, a liposome, a micelle, an implant, a stent, a paste, a gel, a dental implant, or a medical implant.

The following examples are included to demonstrate some embodiments of the disclosure. However, those of skill in the art should, in light of the present disclosure, appreciate that many changes can be made in the specific embodiments which are disclosed and still obtain a like or similar result without departing from the spirit and scope of the invention.

Examples

*Streptococcus pyogenes* [Group A *Streptococcus* (GAS)] is a major public health concern, with estimates of over 700 million cases of GAS infections per year[1]. GAS commonly manifests as pharyngitis, commonly called "strep throat". However, GAS is also a major cause of highly contagious skin infections worldwide, ranging from superficial infections, such as impetigo, to deeper, more life-threatening illnesses such as cellulitis and necrotizing fasciitis[2]. Untreated GAS skin infection has also been linked to a chronic autoimmune illness known as glomerulonephritis, a prominent cause of kidney failure[3]. Superficial GAS skin infections frequently spread to the upper respiratory tract, causing GAS pharyngitis, which is associated with other debilitating autoimmune illnesses, such as acute rheumatic fever (ARF), rheumatic heart disease (RHD), and neuropsychiatric diseases[4-6]. Notably, severe forms of GAS infection are highly concentrated in areas where poverty is endemic[5,7,8]. The vast majority of these cases occur in children and are correlated with reduced quality of life and increased risk of early death[1,4].

Despite the widespread nature of GAS infections and their association with severe adverse outcomes, no vaccine for this pathogen currently exists, partly due to the risk of autoimmunity following exposure to GAS antigens[9]. Recent studies revealed post-streptococcal autoimmune illnesses are associated with cross-reactivity between antibodies against the major GAS virulence factors, M protein and the GAS surface carbohydrate, and important structural proteins in the heart and joints[10]. Importantly, such findings disqualify the native forms of these critical virulence factors from being developed as vaccine candidates. Given the inherent difficulties associated with developing vaccines against the two major GAS virulence factors, the evaluation of novel bacterial virulence determinants represents an attractive avenue towards the development of a safe, universal vaccine for this important human pathogen.

Applicant's lab recently leveraged an innovative nanosponge-based affinity enrichment technique, Biomimetics Virulomics, to discover and characterized a previously unannotated GAS virulence factor[11]. This novel virulence factor was named S protein due to the wide distribution of homologs across the Streptococcal genus. Functional analysis of an S protein isogenic mutant strain (Δess) revealed that removal of S protein severely weakened bacteria against host innate immune defenses, suggesting that S protein is a previously overlooked central virulence determinant. In support of this notion, the Δess strain showed a robust remodeling of the bacterial virulome relative to the wild type strain, suggesting that S protein plays an important role in bacterial physiology[12].

Given these results demonstrating S protein's key role in virulence, applicant sought to determine whether S protein could serve as a viable protective vaccine against GAS infection[13]. Applicant first used unbiased sequence alignment and determined that S protein's sequence is highly conserved among *S. pyogenes* strains. Enzymatic surface shaving of GAS strains confirmed native S protein is surface exposed among various strains, and antibodies raised against recombinant S protein bound to the bacterial surfaces of multiple serotypes. Corroborating this preliminary evidence, applicant next observed that recombinant S protein exhibited a robust ability to protect animals from localized GAS skin infection in an S protein-dependent fashion in vivo. Using a quantitative proteomics-based approach, applicant observed that lesions collected from S protein-naïve animals infected with GAS mounted rapid innate immune engagement, while immunized animals exhibited a strong antibody-based response. These results represent a first step in the development of an S protein vaccine against GAS, a major cause of pediatric morbidity and mortality worldwide.

Sequence of Recombinant S Protein is Highly Conserved in GAS

Figure 1B:
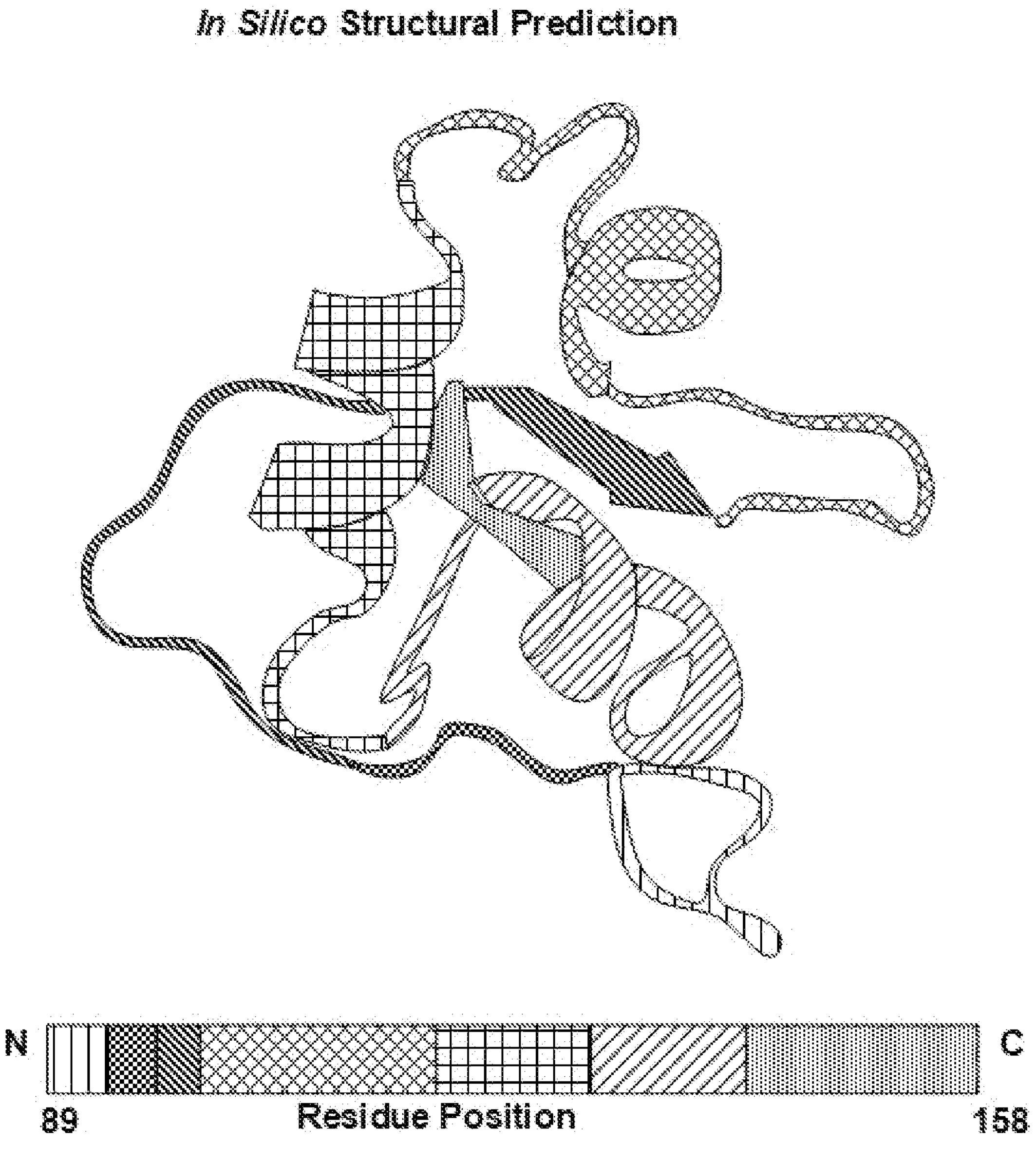
Figure 5A:
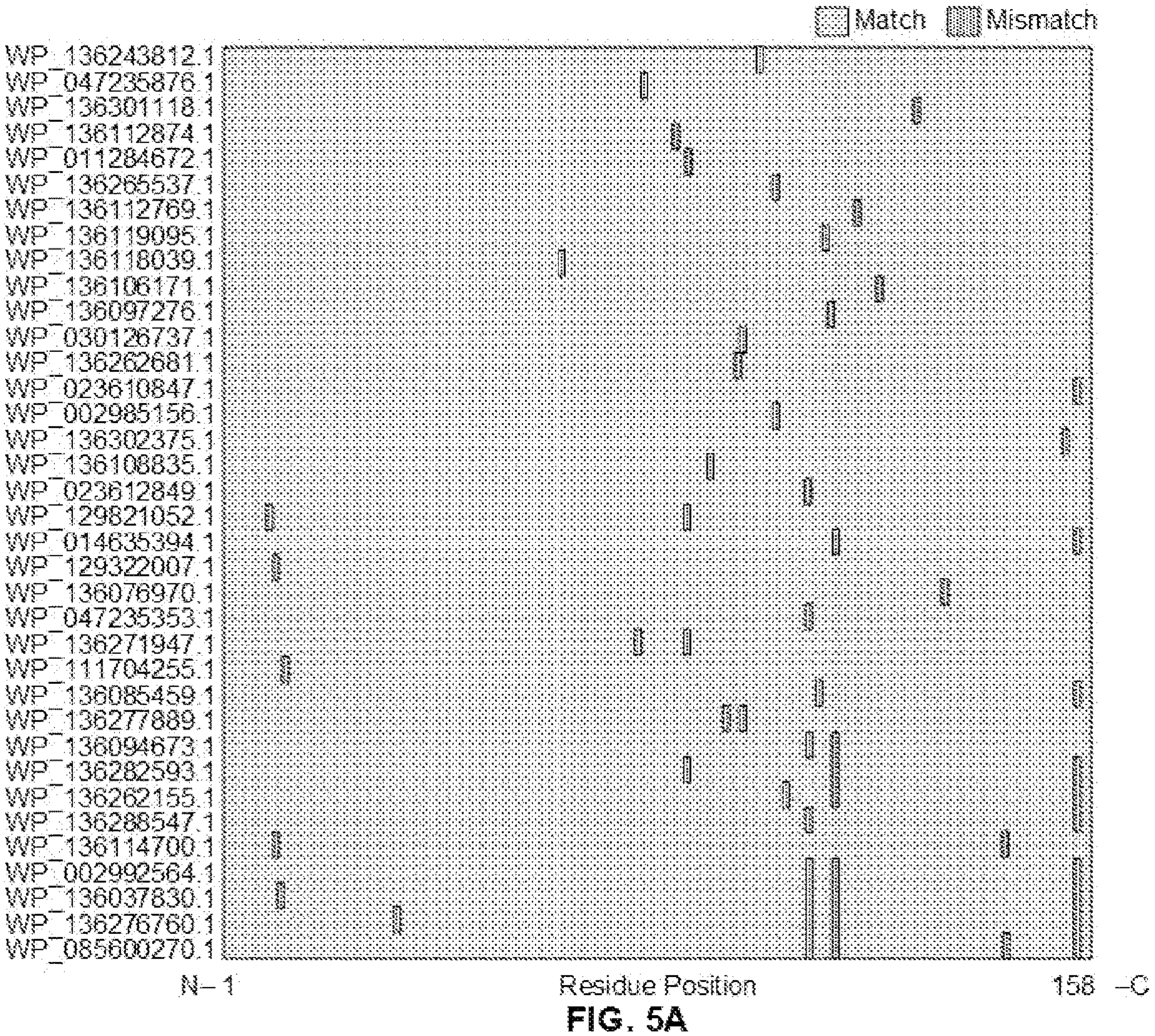
FIGS. 5A-5B: Expanded analysis of recombinant S protein mass spectrometry results.

Recombinant S protein was purified from an *E. coli* strain engineered to express the S protein sequence from the M1 GAS strain 544812. To assess the degree of sequence identity for S protein homologs in the Streptococcal genus in an unbiased fashion, the M1 template used to generate recombinant S protein was subjected to PSI-BLAST analysis, where 44 sequences were ascribed to *S. pyogenes* (GAS). All identified proteins with sequence similarity to the GAS S protein template were then used to generate a circular dendrogram, which showed a high degree of clustering among S protein sequences from GAS strains (FIG. 1A). Among the identified GAS S protein sequences, the strains showed over 90% identity to one another (FIG. 5A). A crystal structure for S protein currently does not exist, but structural prediction using Phyre2 yielded a predictive model for the C-terminal 69 residues (43.7% of total residues) with 99.4% confidence[14] (FIG. 1B).

Figure 1C:
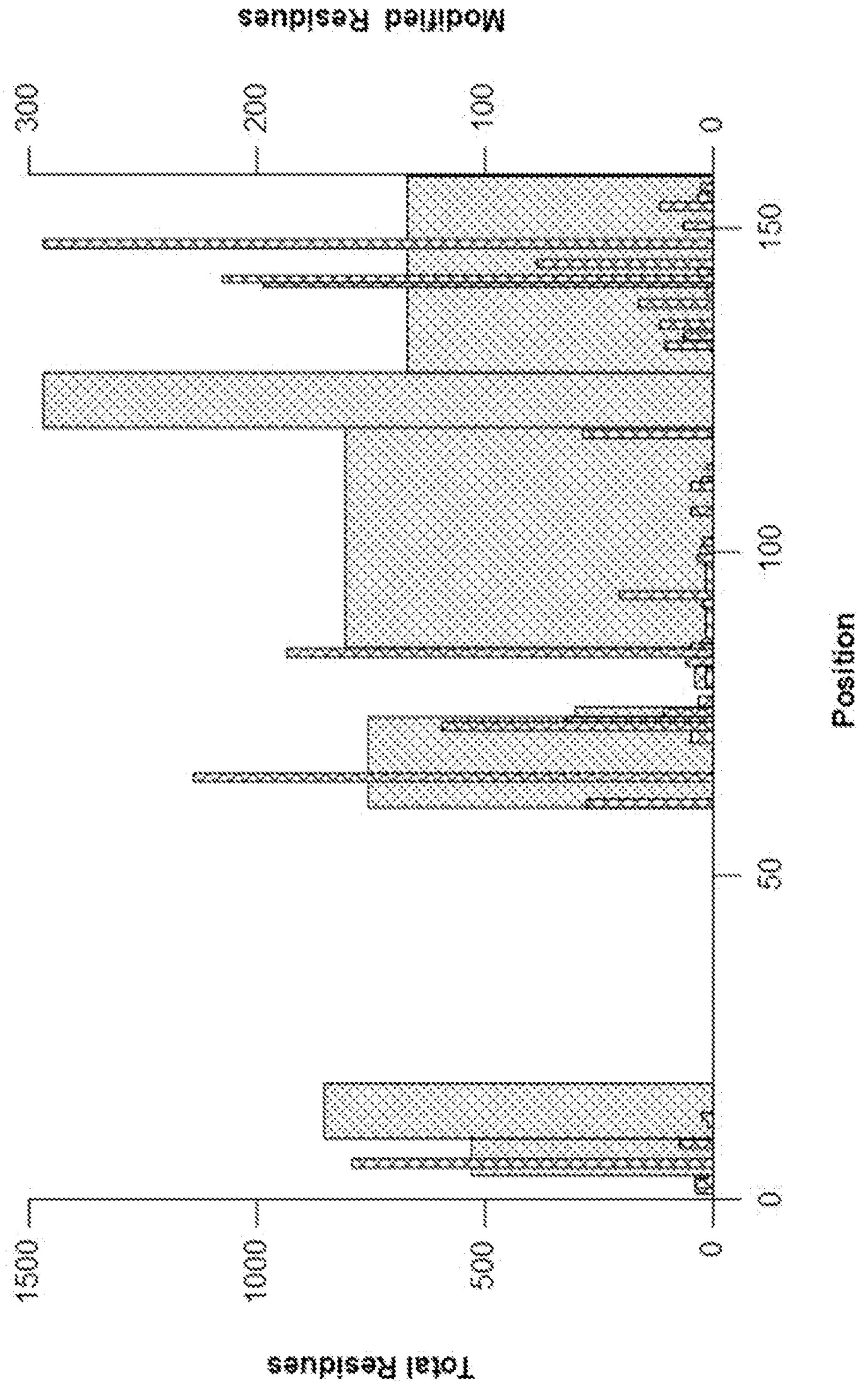
Figure 1D:
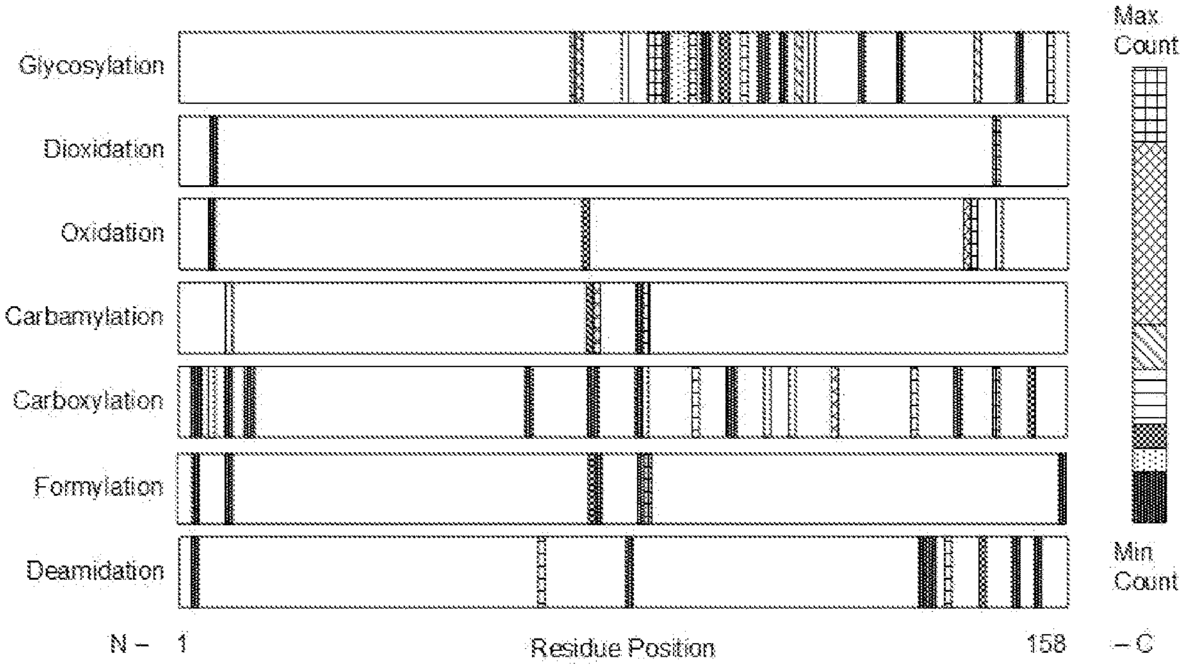
Figure 5B:
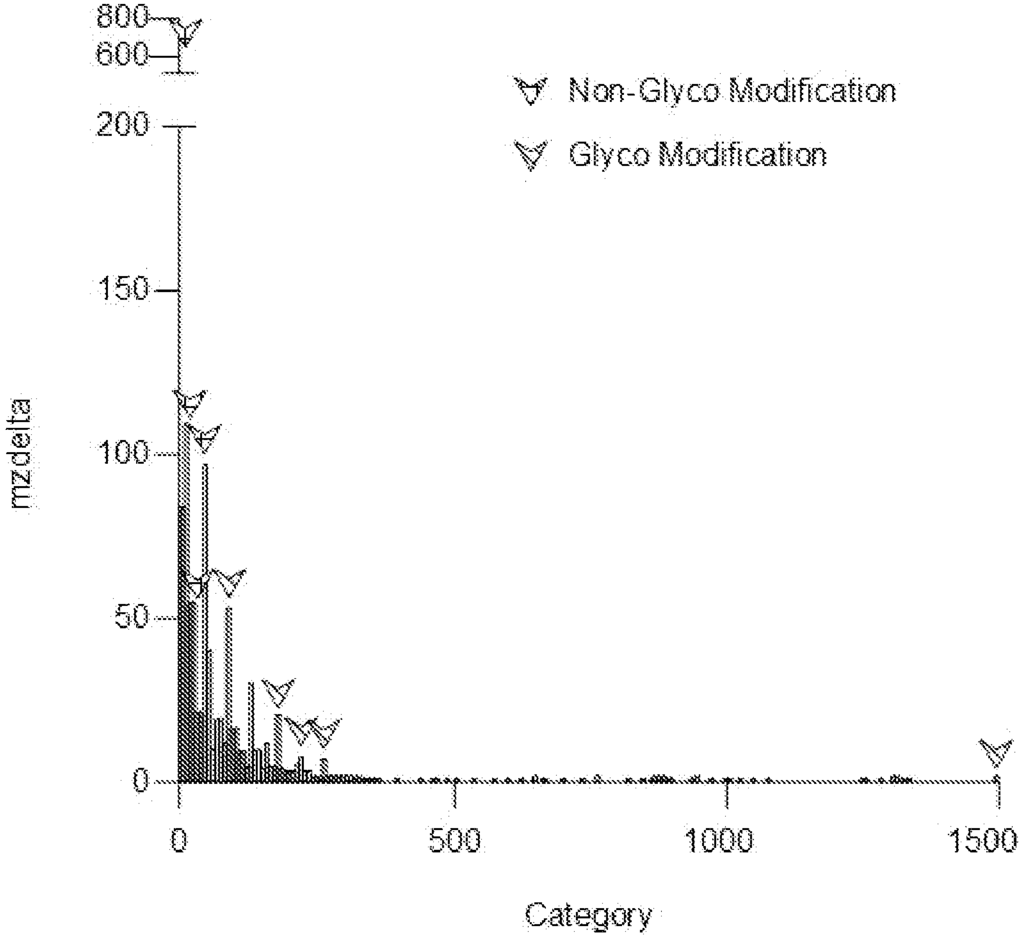

Post-translational modifications (PTMs) affect tertiary structure of proteins, and the three-dimensional structure of proteins informs immune recognition of foreign antigens. To evaluate the degree to which recombinant S protein was modified, mass spectrometry-based analysis of recombinant S protein was performed. A PTM-tolerant search of the MS2 spectra collected determined that several residues were predicted to be modified throughout S protein (FIG. 1C). Prominent modifications included deamidation, oxidation, dioxidation, formylation, carboxylation, carbamylation, and various glycosylations (FIG. 5B). To aid in visualizing the distribution of various detected modifications, they were localized to specific residues and mapped to the S protein sequence (FIG. 1D). While many of these modifications could be artifacts of sample preparation, glycosylations were identified most in the C-terminal regions of the protein, suggesting they may also be of biological significance. (FIG. 1D).

Anti-S Protein Antibodies Bind the Surface of GAS

Previous efforts predicted that S protein is cell surface exposed; however, there is little information on the native orientation of S protein within the cell wall or its ability to foster opsonization with antigen-specific antibodies[12,13]. To examine these questions, applicant employed enzymatic digestion of bacterial surface epitopes (the "surfome") and sequenced them using mass spectrometry to determine whether S protein-derived peptides could be detected[13]. Four GAS strains representing clinically-prevalent serotypes (M1, M3, M4, and M12) were analyzed[15-18]. Notably, surface shaving of all analyzed strains led to the detection of S protein peptides, suggesting that S protein is widely present on the GAS surface (FIGS. 2A-2D).

Figure 2A:
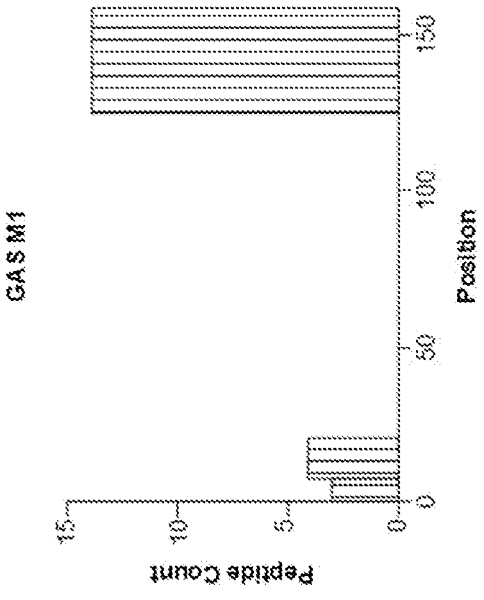
FIGS. 2A-2E: GAS S protein is surface exposed and is susceptible to anti-S Protein antibodies.
Figure 2B:
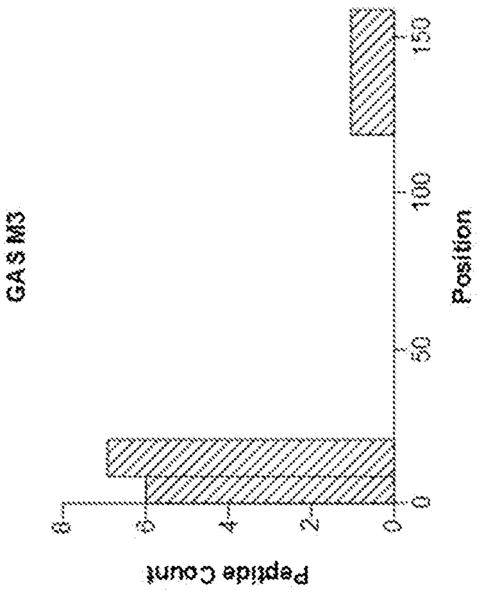
Figure 2C:
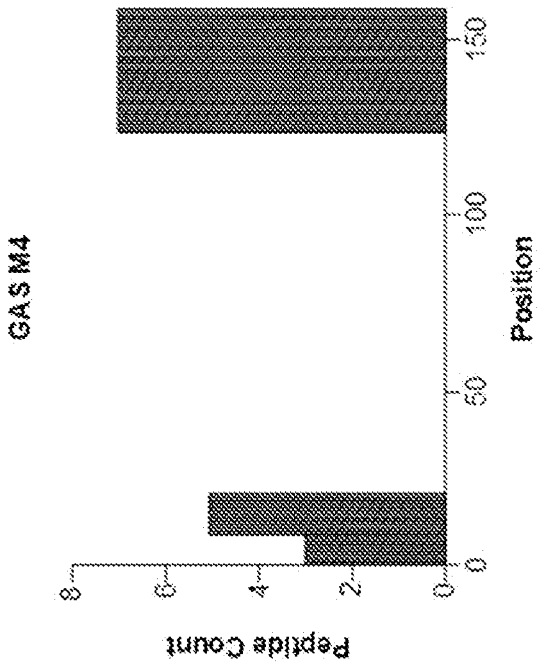
Figure 2D:
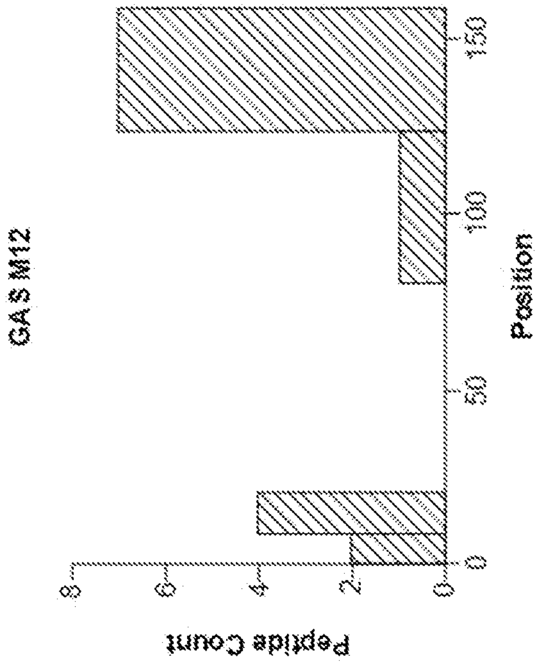
Figure 2E:
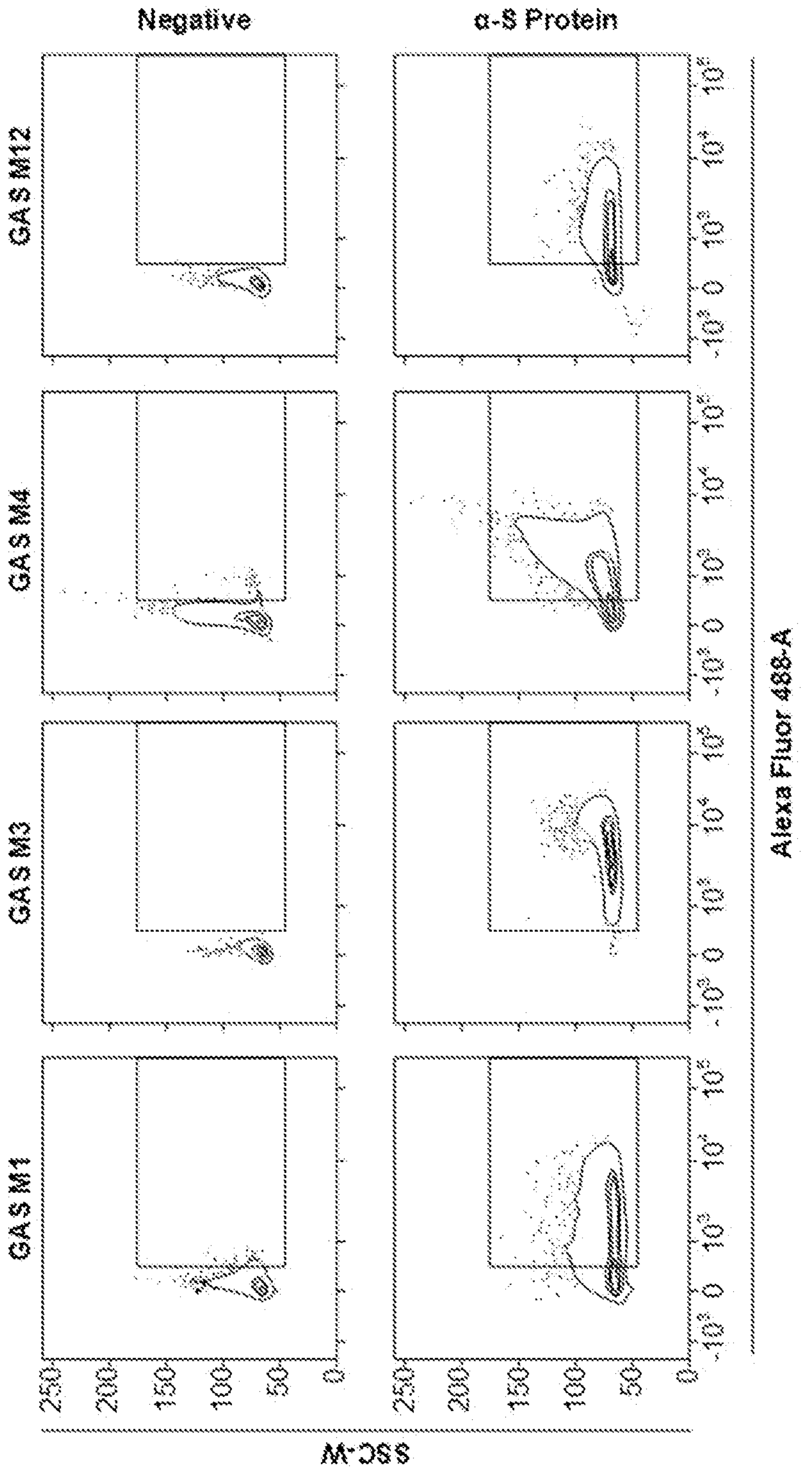

Given the detection of S protein on the surface of GAS strains, applicant sought to determine whether antisera generated against recombinant S protein could bind the surface of GAS strains through flow cytometry. Bacteria incubated in anti-S protein antisera showed an increase in fluorescence intensity compared to negative controls in M1, M3, M4, and M12 strains assessed (FIG. 2E, FIG. 6A).

Figure 6D:
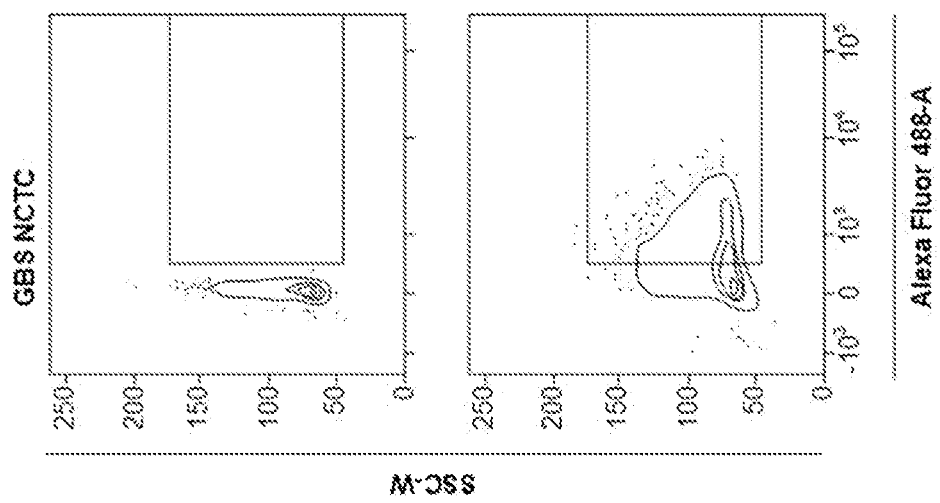
Figure 6C:
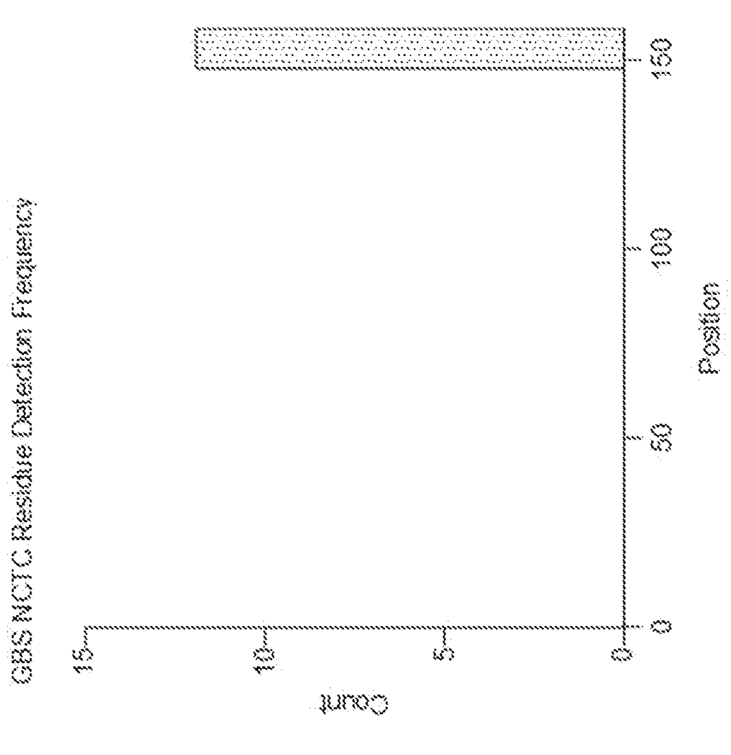

Because S protein homologs exist across the Streptococcal genus, applicant next wondered whether S protein's cell-surface orientation would be retained in another species, Group B *Streptococcus* (GBS). Sequence identity between S protein homologs in GAS and GBS ranged from 20-71% in sequences identified through BLAST-P analysis (FIG. 6B). To confirm that this homolog was also present on the GBS surface, applicant repeated surfome shaving using the CNCTC 10/84 strain[19]. Interestingly, while applicant did recover peptides derived from the GBS S protein homolog, they were heavily biased towards the C terminal region of the protein, suggesting that this protein may differ from its GAS counterpart in its orientation within the bacterial cell wall (FIG. 6C). Next, flow cytometry using antibodies raised against GAS S protein was performed to determine whether anti-GAS S protein antisera showed cross-reactivity with GBS. Interestingly, anti-S protein antibodies showed poor binding to the bacterial cell surface compared to GAS strains (FIG. 6A, FIG. 6D). However, it is unclear whether this difference in binding is a result of the divergent sequence of the protein, its more limited exposure on the bacterial cell surface, or a combination of both factors.

S Protein Immunization Protects Mice Against Localized GAS Infection

Figure 3A:
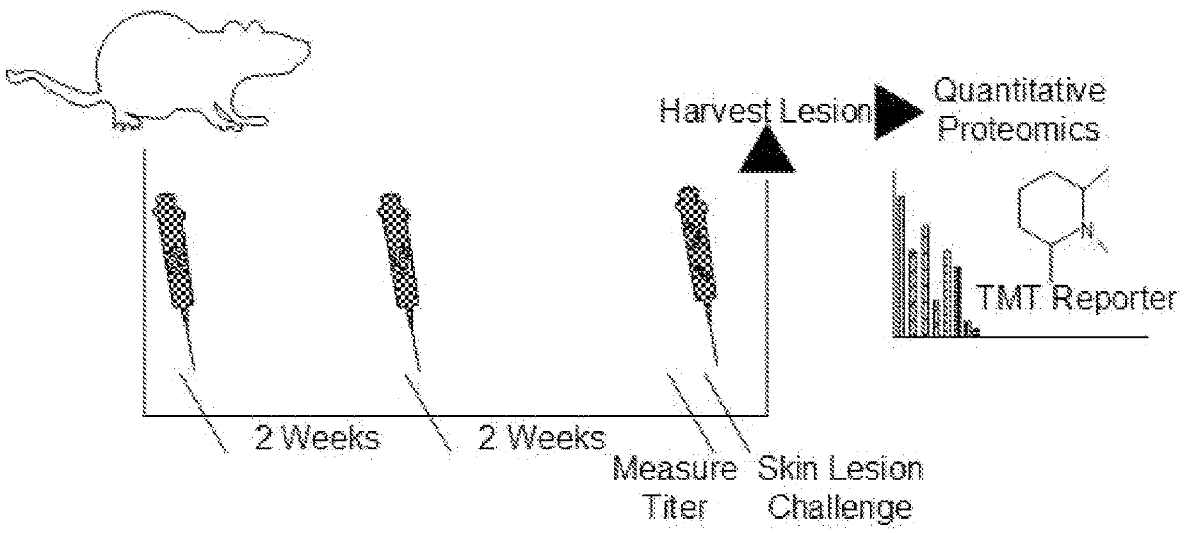
FIGS. 3A-3E: Recombinant GAS S protein protects against localized GAS infection in a skin model.
Figure 3B:
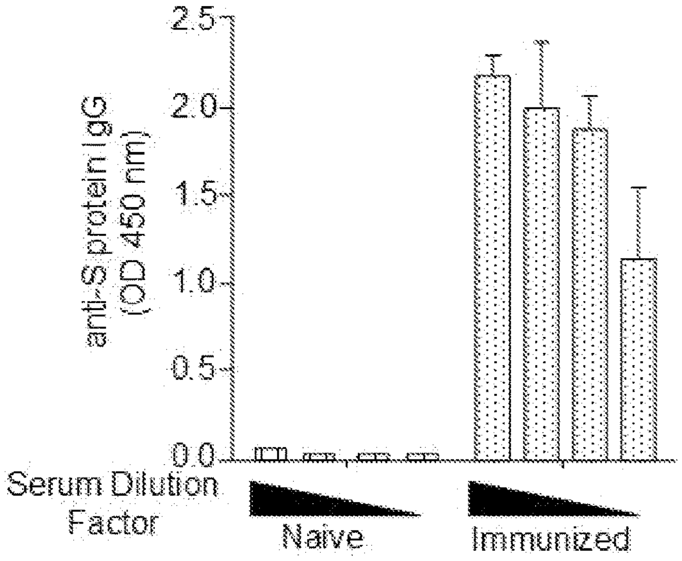
Figure 7A:
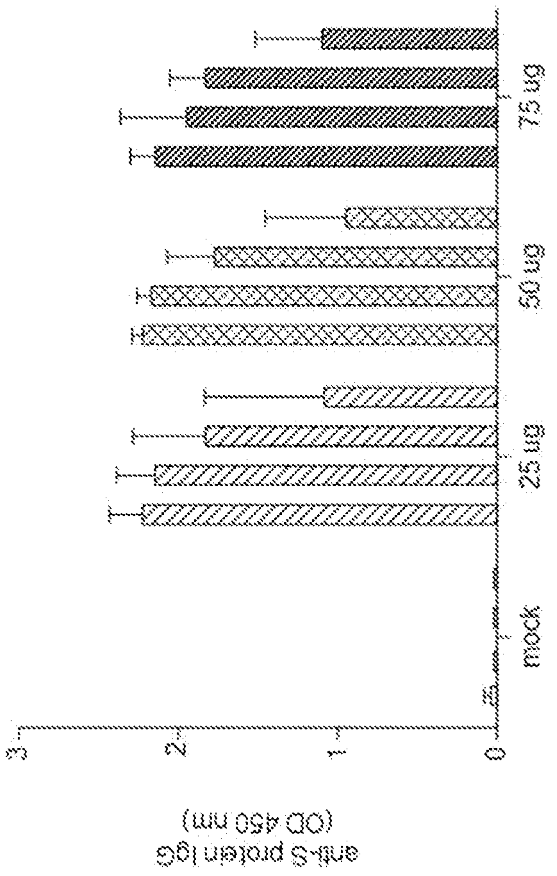
FIGS. 7A-7C: Recombinant S protein immunizes animals against GAS infection.

Having evidence of anti-S protein antibody binding to GAS in vitro, applicant next sought to test whether immunization with recombinant S protein would lead to protection for GAS infection in vivo. Mice were immunized with recombinant S protein or an aluminum hydroxide adjuvant (alum) alone using a two-dose scheme, with injections spaced two weeks apart (FIG. 3A). Immunization was initially tested with varying amounts of recombinant S protein (25 μg, 50 μg, and 75 μg) (n=5 per group). The two-injection scheme resulted in vigorous anti-S protein antibody production at all concentrations (FIG. 7A, FIG. 3B).

Figure 3D:
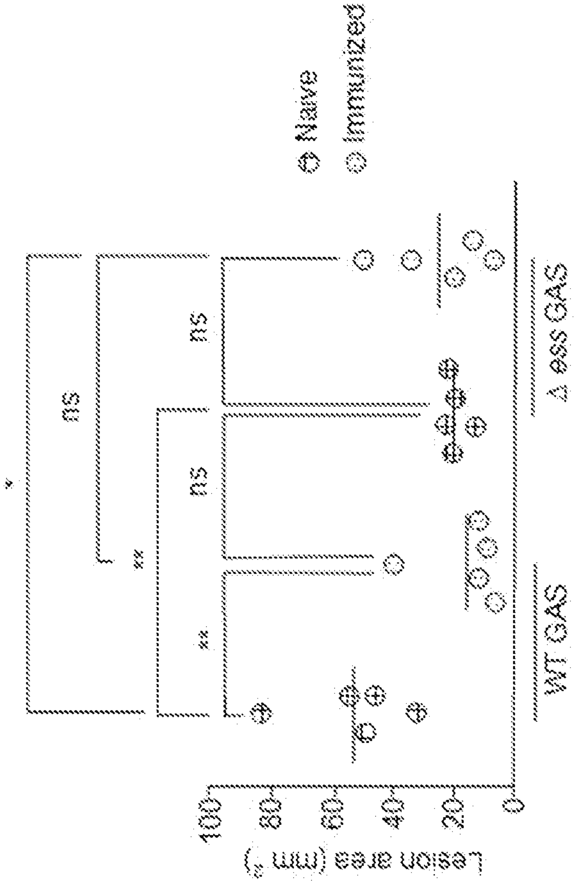
Figure 3C:
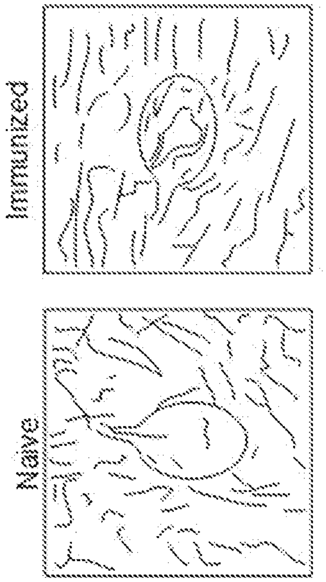
Figure 3E:
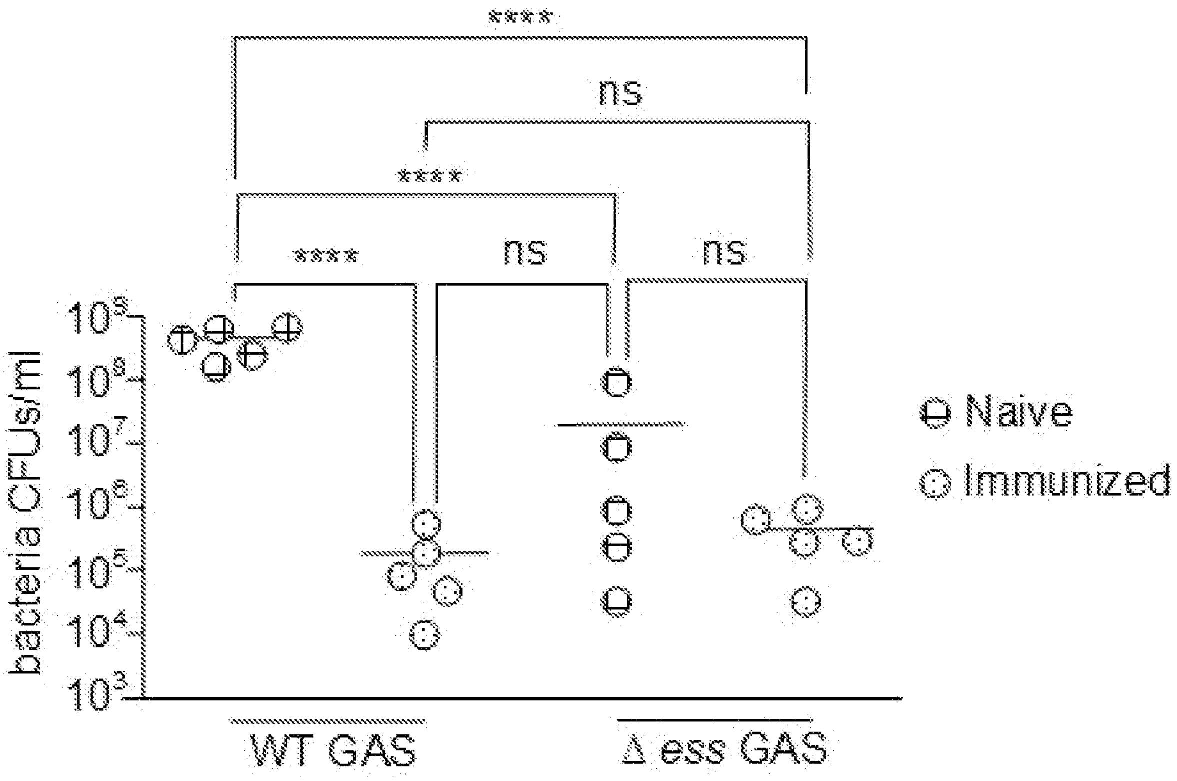

S protein-immunized (75 μg each) and naïve mice were infected intradermally with either WT GAS or the Δess isogenic mutant strain (n=5 per group). Lesions were allowed to form for three days, at which time lesion area was measured and lesions were isolated, pulverized, and serially diluted for bacterial CFU enumeration. In WT-infected naïve animals, lesions adopted an inflamed, gaping appearance, whereas immunized mice showed signs of rapid healing, with scabbing and reduced lesion diameter (FIG. 3C). Lesions from immunized mice were also significantly smaller than in the naïve animals in the WT GAS infected group (FIG. 3C-FIG. 3D). Notably, there was no significant difference in lesion area in animals infected with the less strain, regardless of whether animals were immunized against S protein or not (FIG. 3D). On CFU enumeration of homogenized lesion samples, there was a greater than three-log significant decrease in recoverable CFUs in immunized animals infected with the WT strain compared to the naïve animals (FIG. 3E). Again, animals infected with the less strain showed no significant difference in recovered CFUs in either the naïve or immunized groups, indicating the specificity with which anti-S protein immunity conferred protection against GAS infection (FIG. 3F). Also notable were the significantly reduced lesion size and recovered CFUs in the Δess infected group compared to the WT GAS infected group. Recent work from applicant's lab indicated that S protein deletion substantially impaired virulence in a systemic infection model[12]. Reinforcing its virulent nature, the results presented here indicated S protein immunization plays a critical role in localized GAS skin infection, a major cause of pediatric morbidity worldwide. Taken together, these results provide strong evidence of S protein's potential as a vaccine candidate against GAS infection and S protein's role in promoting virulence during localized skin infections.

Probing the Host Response to GAS Infection after S Protein Immunization

Figure 7B:
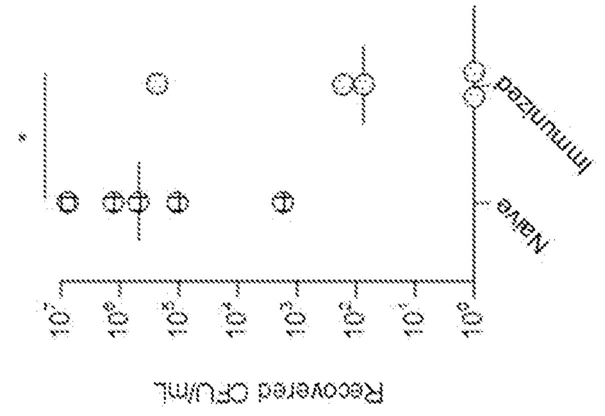
Figure 7C:
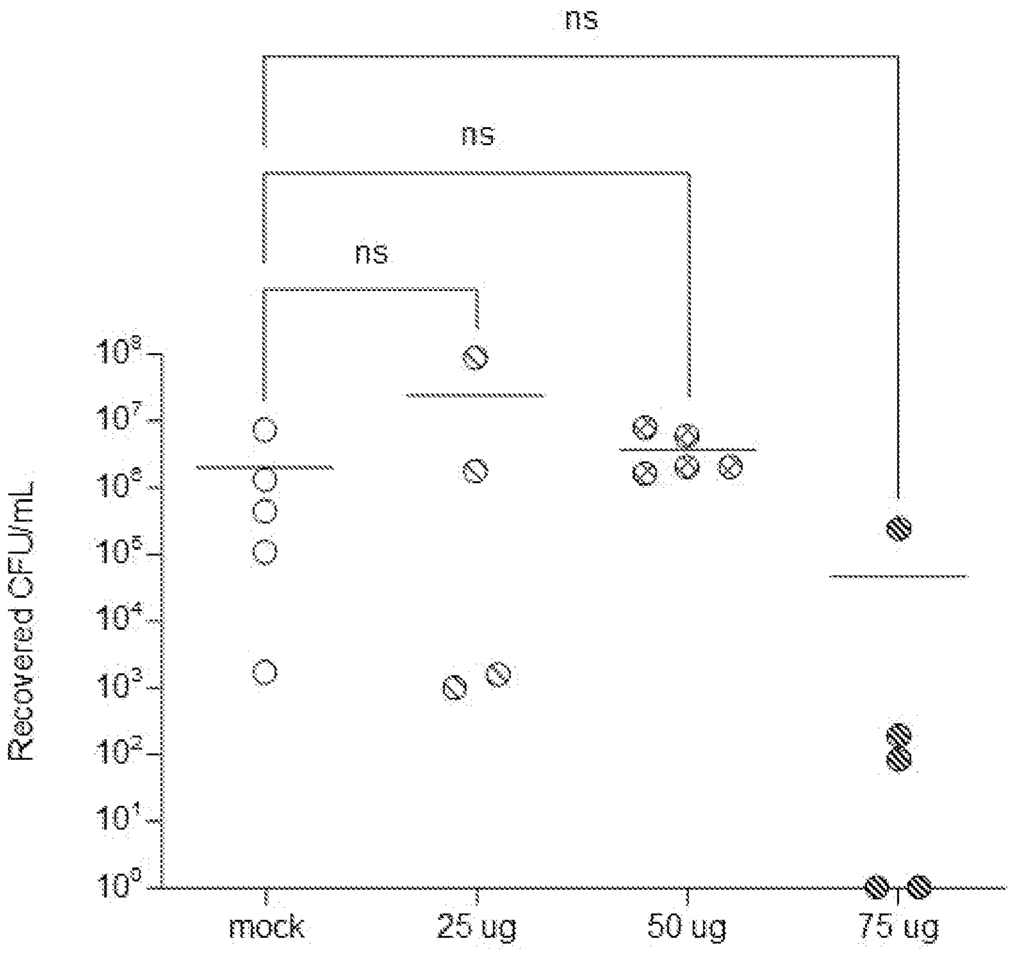

In order to understand the host pathways underlying the differential immune responses associated with GAS infection in immunized and naïve states, applicant performed tandem mass tag (TMT)-based unbiased quantitative proteome analysis of skin lesion lysates derived from the 75 μg group of the initial dosing experiment (n=5 per group) (FIG. 7B—FIG. 7C). Through proteomics, applicant identified and quantified 3,658 proteins after quality control filtering steps.

Figure 4B:
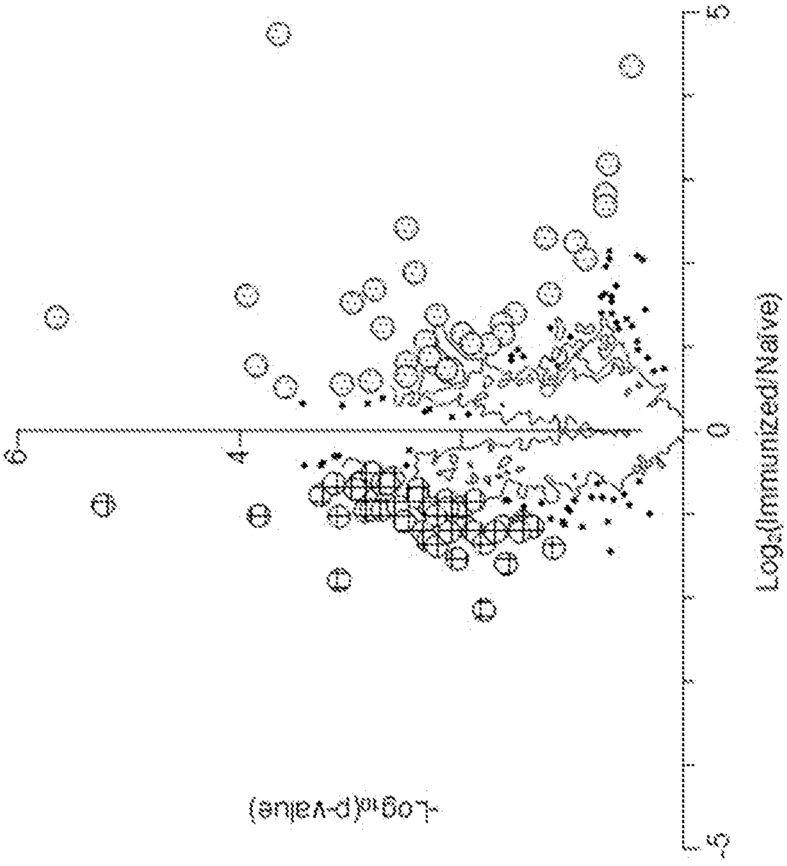
FIGS. 4A-4M: Differential host responses to GAS infection in the context of prior S protein immunization.
Figure 4A:
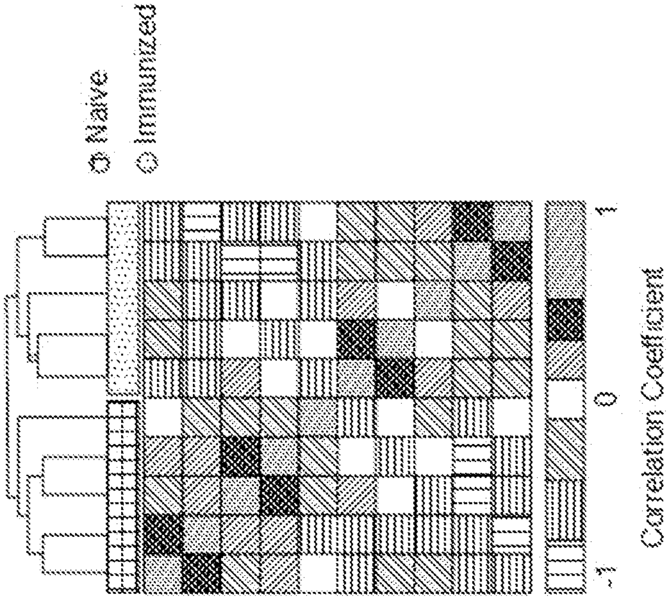
Figure 4C:
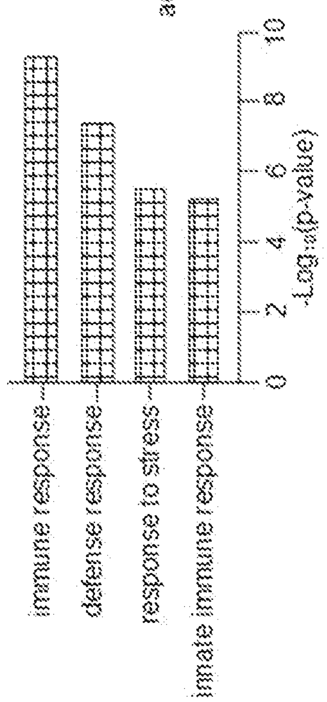
Figure 4D:
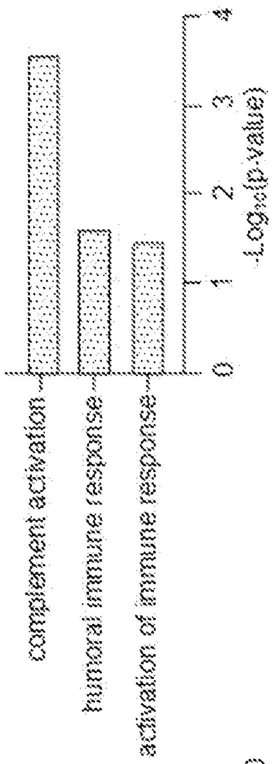

In order to understand broad overall trends in the proteome data, it was initially subjected to hierarchical clustering. Samples clustered based on immunization status, indicating divergent host responses to GAS infection predicated on prior S protein immunization (FIG. 4A). Binary comparison of the proteome data was performed to identify proteins with abundance changes significantly associated with immunization (FIG. 4B). It score was used to identify significantly altered proteins, as it incorporates both p-value based significance and fold change[20]. 38 proteins were defined as being significantly increased, whereas 67 proteins were defined as being significantly decreased in the immunized compared to the naïve cohort. To test for biologically relevant trends in immunization-respondent features, gene ontology analysis was performed. The top biological process terms associated with S protein vaccination included "complement activation" and "humoral immune response," indicating a rapid engagement of both protein-based innate and adaptive immune components (FIG. 4C). In contrast, the top enriched terms associated with innate immunity and a generalized response to stress (FIG. 4D).

Figure 4E:
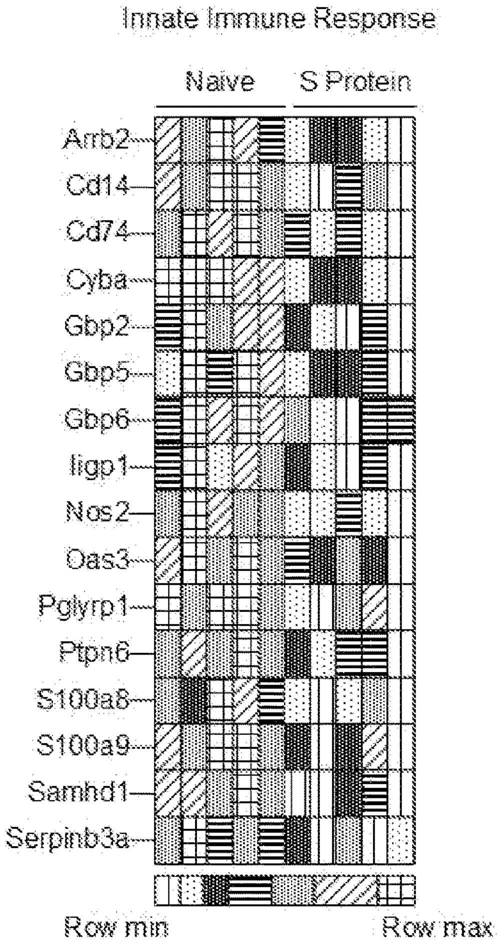
Figure 4F:
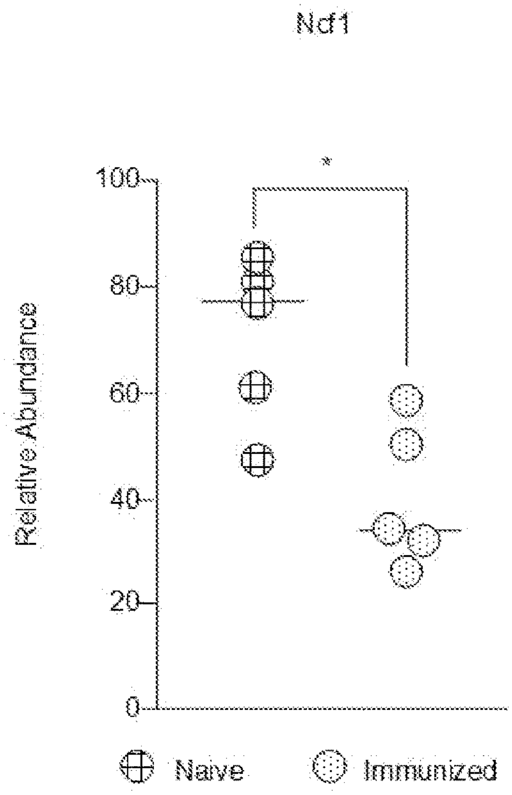
Figures 4G, 4H:
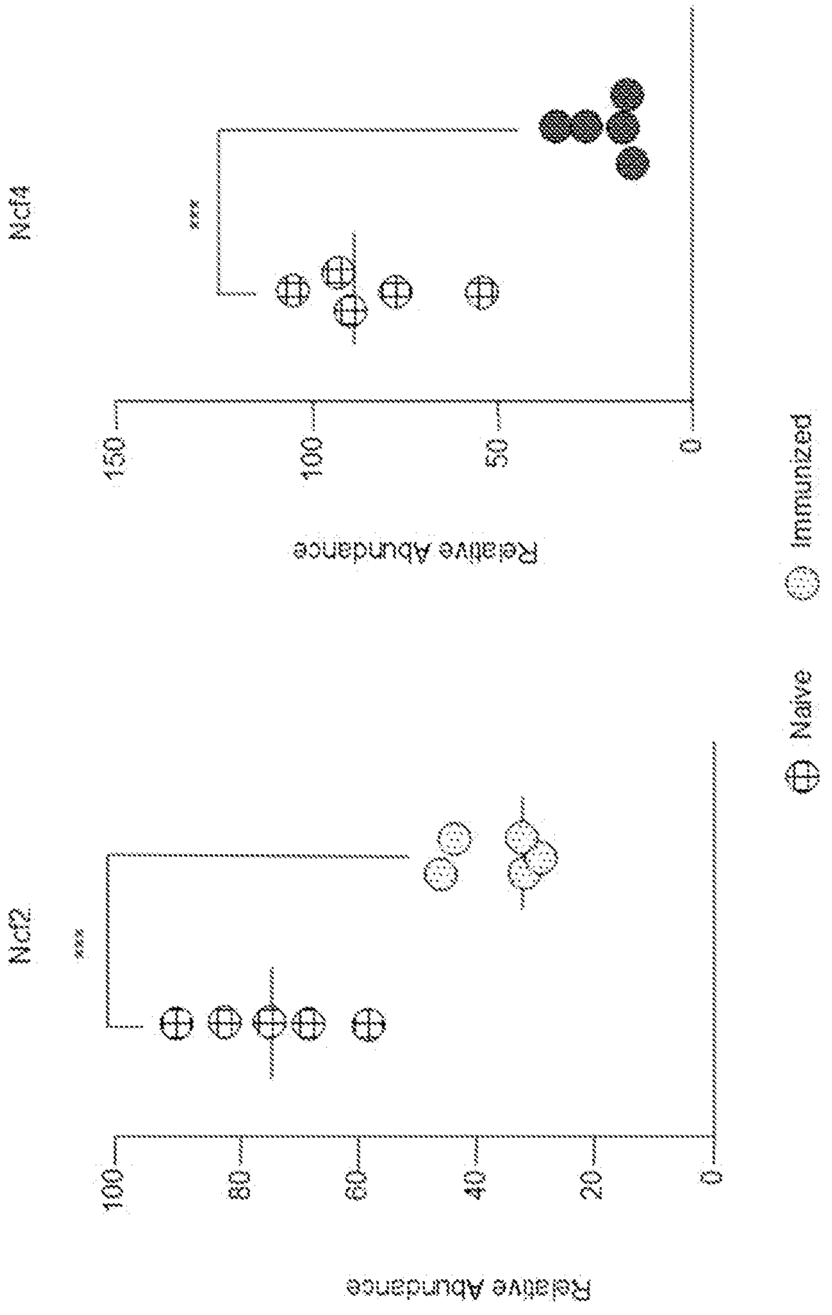
Figure 4I:
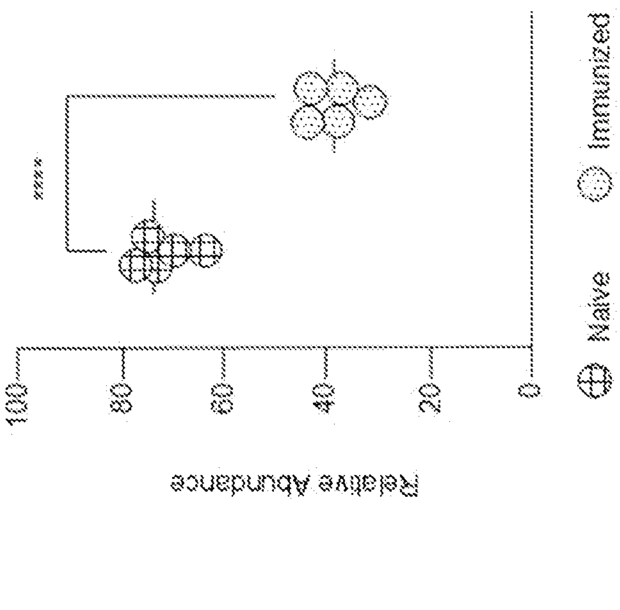
Figure 4J:
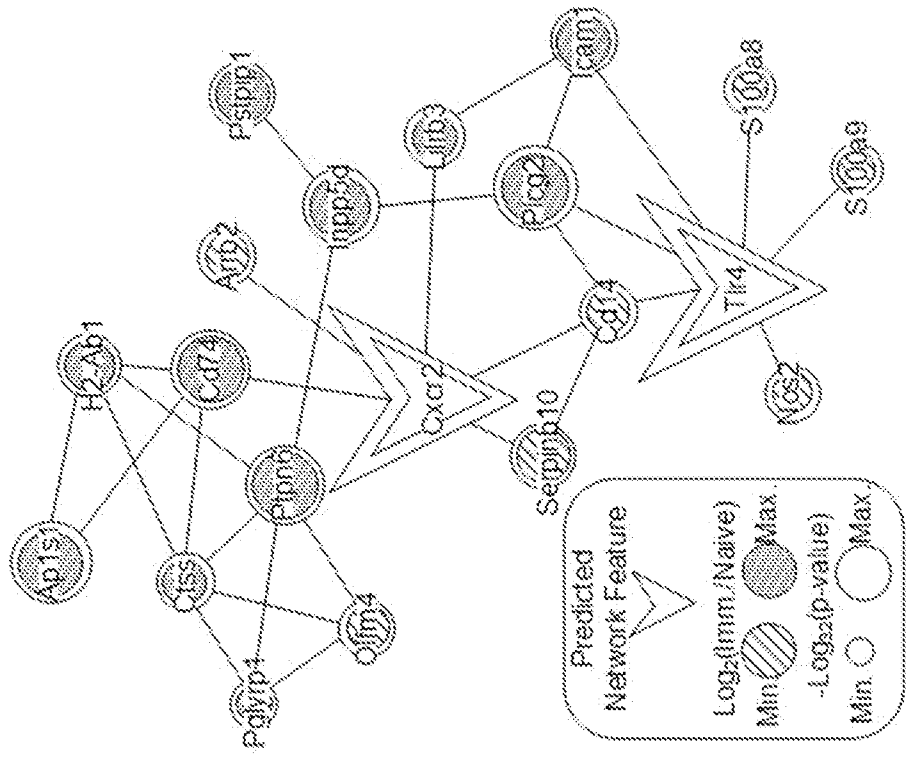

Further evaluation of proteins significantly increased in naïve animals compared to immunized animals revealed that several defined markers of innate immunity were significantly higher in naïve animals compared to immunized animals (FIG. 4E). Examples include CD14, a marker and pattern recognition receptor (PRR) of macrophages, and Nos2, a protein involved in antimicrobial activity of macrophages[21-23]. Also noted was an upregulation in several neutrophil cytosolic factors (Ncf1, Ncf2, Ncf4), and the related protein, Cyba. Ncf proteins partner with Cyba to generate large amounts of superoxide, a critical antimicrobial defense element[24-26] (FIG. 4F-FIG. 41).

Figure 8:
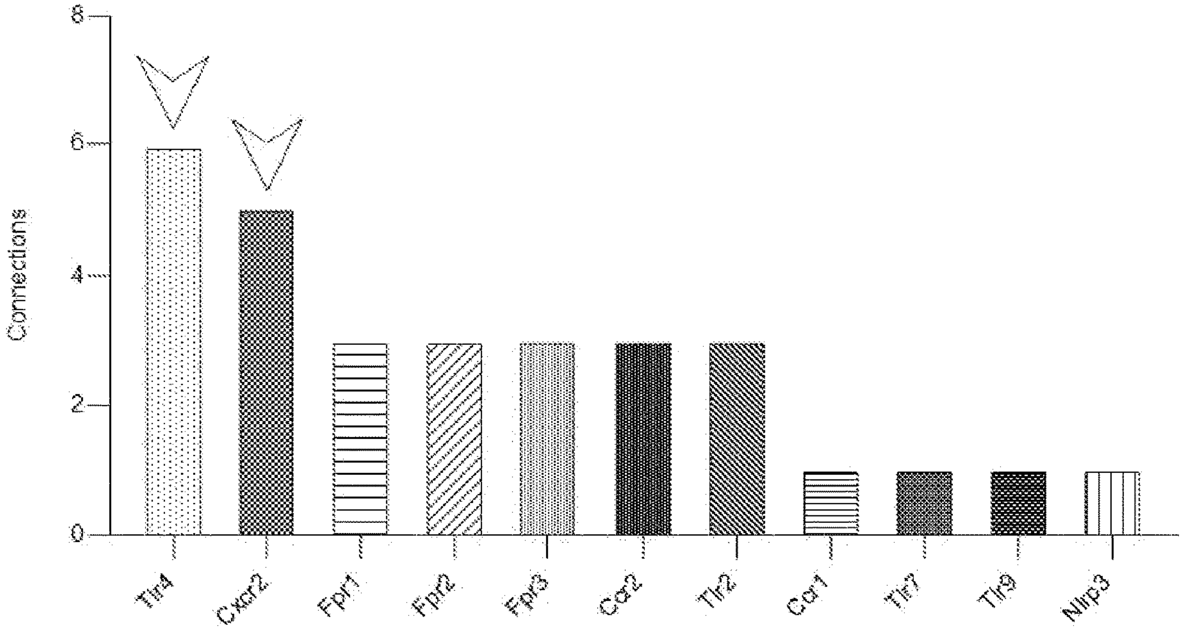

Neutrophil engagement is instigated by a litany of cell surface receptors. Because several antimicrobial proteins linked to neutrophils were increased in naïve infected animals compared to immunized animals, without wishing to be bound by the theory, applicant hypothesized that the response to GAS infection in naïve animals was regulated by a subset of these receptors. However, proteome analysis of applicant samples did not detect these receptors, likely due to the innate difficulties associated with analyzing membrane-integrated proteins through mass spectrometry[27,28]. To overcome this challenge, applicant employed String-db, a protein-protein interaction predictor to visualize which infection-associated proteins in naïve animals could be regulated by neutrophil receptors in an unbiased fashion[29]. Though not detected in the proteome data, TLR4 and Cxcr2 assumed central positions within a larger protein-interaction network comprised by neutrophil signaling proteins, with TLR4 directly connected to 6 proteins and Cxcr2 connected to 5, suggesting that these receptors mediated the response to GAS infection in naïve animals (FIG. 4J; FIG. 8)[30-33].

Figure 4K:
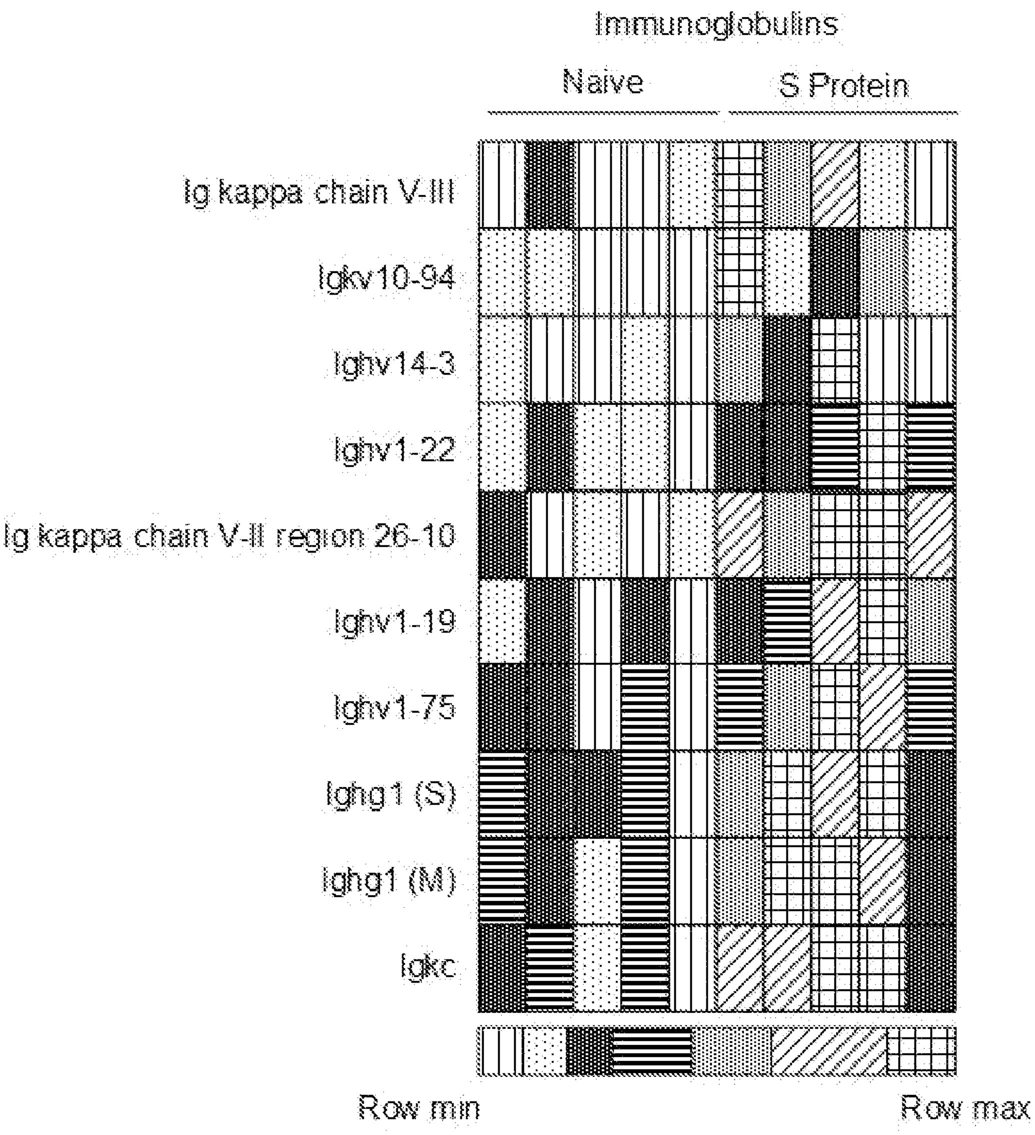
Figure 4M:
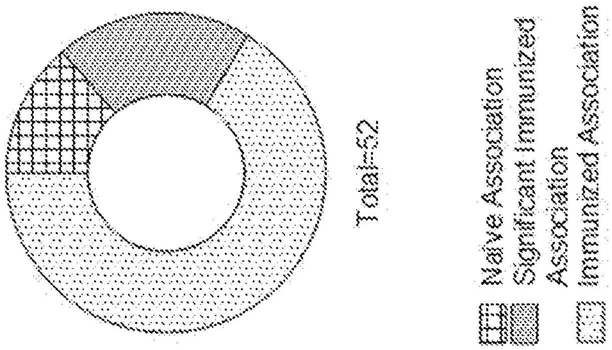
Figure 4L:
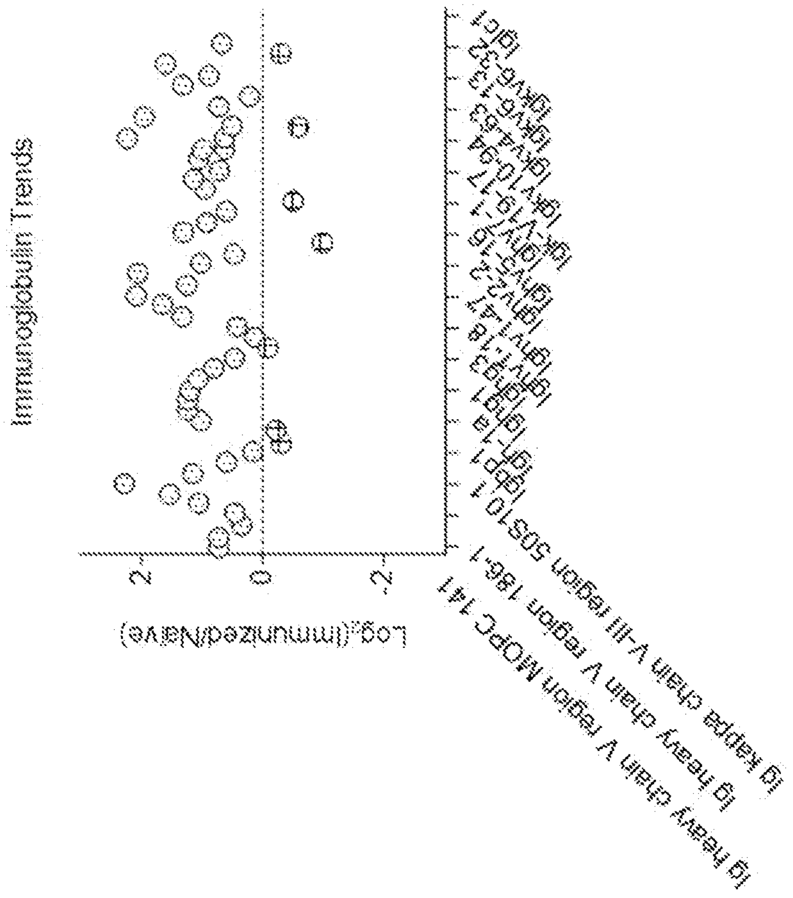

Applicant next analyzed the set of proteins increased during GAS infection in immunized animals. It was noted that of the 38 upregulated proteins in this group, 10 were immunoglobulins-derived (FIG. 4K). Applicant speculated whether immunoglobulins were increased beyond the bounds of the applied statistical significance threshold. Of the 52 immunoglobulin-derived proteins detected in the proteome dataset, 45 were increased during infection in S protein immunized animals (FIG. 4L-FIG. 4M). These findings align with the intent of immunization with S protein, eliciting rapid, antibody-based immunity during GAS infection. Taken together, the findings of applicant proteome study indicate that although GAS infection in naïve animals stimulates a robust innate immune response, pre-immunization with recombinant S protein results in antibody-based killing and immune memory to rapidly kill bacteria.

Antibodies raised against recombinant S protein bound the surfaces of diverse GAS strains. This finding was unsurprising, as GAS S protein is highly conserved in sequence among GAS strains. Additionally, the putative surface exposed portions of GAS S protein detected via mass spectrometry after enzymatic surface shaving largely mapped to similar regions. This finding suggests that immunization with recombinant GAS S protein could be broadly protective against GAS infection and could confer a degree of protection against other Streptococcal pathogens, including GBS. Though homologs of S protein exist widely in the Streptococcal genus, sequence divergence exists and the orientation of S protein between species is likely variable. Further studies are performed to determine the protective value of immunity elicited against S protein in the broad context of Streptococcal infection.

Though preliminary proof-of-principle evidence presented here strongly supports S protein as a vaccine antigen, expanded studies are under investigation to evaluate the full range of S protein's implications in mitigating the GAS-host relationship. Recent studies have demonstrated the efficacy of combinatorial vaccines comprised of multiple highly conserved, surface exposed antigens[37,38]. Though recombinant S protein conferred protection against GAS infection, it could be even more valuable as a part of a combinatorial vaccine, possibly adding to the universality of previous combinatorial vaccine endeavors. Additionally, the model used in this study was focused to skin lesions, which are a highly prevalent manifestation of GAS infection. However, GAS-induced pharyngitis remains the most common form of GAS infection. Like impetigo and other skin infections, GAS pharyngitis carries with it a risk of developing autoimmune sequelae, so any further testing of S protein as a vaccine candidate should account for this important condition. Recent studies have focused on non-human primates (NHP) as a model for GAS pharyngitis, as mice are poor models for "strep throat" due to their lack of tonsils[38]. Future studies on the universal potential of S protein as a vaccine candidate are under investigation using these NHP models, as they more realistically recapitulate GAS infection of the pharynx.

In summary, the results provided here represent a strong rationale for the further evaluation of S protein as a vaccine antigen.

Materials and Methods

Bacterial Strains

GAS M1, M3, M4, and M12 strains and GBS CNCTC 10/84 strain were a kind gift from the laboratory of Dr. Victor Nizet. GAS strains were grown in Todd-Hewitt Broth supplemented with 0.2% yeast extract (THY), and GBS strains were grown in Todd-Hewitt Broth (THB). All strains were initiated from frozen glycerol stocks stored at −80° C.

S Protein Sequence Analysis

The S protein sequence from the GAS M1T1 strain 5448 was subjected to PSI-BLAST analysis, where all matches with over 60% sequence identity and 70% query coverage were retained. The top sequence identity matches were subjected to sequence alignment and cladogram generation using Clustal-Omega[39]. A neighbor-joining tree without distance corrections was generated. A circular dendrogram of the resultant analysis was generated in R using the "dendextend" and "ape" packages[40,41].

Recombinant S Protein Proteome Analysis

Recombinant S protein generated in a previous study was subjected to gel electrophoresis in three separate lanes on an SDS-PAGE gel and stained with Instant Blue[12]. Briefly, three aliquots of 20 μg recombinant S protein was resuspended in 5 μl 4× Laemmli loading buffer and 1 μl reducing agent (500 mM DTT). Samples were boiled for approximately 10 minutes. Samples were loaded with standard ladder (Precision Plus Protein All Blue Prestained Protein Standard, Biorad) into the wells of a 20% SDS-PAGE gel. The chamber was filled with 1×TBS running buffer and samples were run for approximately 45 minutes. After, the gel was extracted from the casing and the stained protein bands were cut out. Three bands corresponding to the ~24 kDa form of S protein were processed separately, and the bands corresponding to the ~18 kDa band were combined into a single replicate. Cut gel bands were further cut into small cubes and placed into clean tubes. Cubes were dehydrated with 50% acetonitrile (ACN) and 50 mM TEAB for approximately 15 minutes on a shaker at 37° C. for two cycles. This was followed by dehydration with 100% ACN. Samples were subjected to vortexing and incubation at room temperature for 5 minutes. Samples were then reduced with 5 μl of 500 mM DTT in 200 μl of water and placed on a heating block for 30 minutes. Samples were then washed with water once and dehydrated as above. Samples were subjected to alkylation with 15 μl of 500 mM iodoacetamide (IAA) in 200 μl of water. Samples were once again rinsed and dehydrated as above. Samples were then digested in-gel using 2.5 μg trypsin (Promega V5113) in 200 μl 50 mM TEAB overnight. Digestion was quenched using 200 μl 50% ACN and 5% formic acid, quenched peptides were transferred to new tube, and gel pieces were subjected to extraction (200 μl 50% ACN and 5% formic acid) on a shaker at 37° C. for 15 minutes, thrice, each time transferring the supernatant to a collection tube for a total of four tubes. A final extraction with 100 μl of 100% ACN was done and collection tubes were dried under vacuum prior to desalting on C18 columns and mass spectrometry analysis.

GAS Surfome Analysis

Group A *Streptococcus* (GAS) strains (GAS M1, M3, M4, and M12) and GBS strain NCTC were grown overnight from frozen glycerol stocks in Todd-Hewitt broth supplemented with 0.2% yeast extract (THY) and Todd-Hewitt broth (THB)-respectively, at 37° C. Bacterial cultures were re-grown the following day to mid-log phase. GBS cultures were grown at a 1:20 dilution in THB for 3 hrs and GAS strains were grown at a 1:20 dilution in THY for 4 hrs. Bacterial cultures were centrifuged at 12,000×g for 5 minutes at 4° C. and washed three times with sterile phosphate-buffered saline (PBS). After the last wash, dried pellets were processed for protein digestion via resuspension in IM urea with 50 mM HEPES and 10 μg of trypsin rotating at 37° C. for 40 min. Digested culture samples were centrifuged at 12,000×g for 5 mins and supernatant was removed and further purified by filtering using Millex-GP 0.22 um polyethersulfone syringe filters. Filtered supernatant samples were then acidified by adding 10 μl of 10% trifluoroacetic acid. Peptides were then desalted using C18 columns using manufacturer's instructions (Waters). Desalted peptides were dried under vacuum and analyzed using an Orbitrap Fusion Mass Spectrometer.

Flow Cytometry

Bacterial cultures were grown overnight in Todd-Hewitt Broth supplemented with 0.2% yeast extract (for GAS strains) and Todd-Hewitt Broth (for GBS). Two aliquots of 2 ml per strain were subjected to centrifugation at 8000×g to pellet cells and bacteria were washed three times with phosphate-buffered saline (PBS). Bacteria were incubated in PBS with 1% heat-inactivated normal human serum for 30 minutes at 4° C. Cells were pelleted through centrifugation at 8,000×g and washed with PBS. Cells were resuspended in PBS alone or PBS with 1:100 heat-inactivated anti-S protein antisera for 1 hour at 4° C. After 1 hour, bacteria were subjected to centrifugation at 8,000×g, washed with PBS, and resuspended in PBS with 1:200 dilution anti-rabbit secondary antibody conjugated to Alexafluor-488. Samples were incubated at 4° C. for 45 minutes rotating before being centrifuged at 8,000×g and resuspended in 1.5% paraformaldehyde. Samples were analyzed using a FACS Arias Cell Sorter. Data were analyzed in FloJo. Parent gates were applied uniformly across all analyzed strains and conditions to segregate the population to be analyzed. A positive gate was applied to the segregated cells to determine the percentage of labeled cells.

S Protein Immunization

For S protein immunization, 5-week old female CD1 (Charles River Laboratories) mice were used. Mice were immunized intramuscularly (i.m.) with 25 μg, 50 μg, or 70 μg of S protein absorbed 1:3 to aluminum hydroxide adjuvant (alum, Alhydrogel® adjuvant 2%, InvivoGen) in a total volume of 100 μl (80 μl/hind leg quadriceps). Control mice received equal amount of alum. Mice received two injections 2 weeks apart.

Mouse Dermonecrosis Model

/S protein immunized mice were shaved and Nair was applied to remove residual hair. Mice were intradermally (ID) injection with 20 μg of GAS M1 ($2\times10^6$ cfu) or GAS M1 Δess. The abscess size was measured at 72 h and the areas of the lesions were calculated using ImageJ. The abscess site was excised and homogenized in PBS. 25 μl of homogenate was serially diluted and plated for enumeration of CFU.

ELISA

S protein-specific IgG antibody was measured by ELISA. Animals were bled 2 weeks after every vaccination. Purified S protein were used to sensitize the ELISA plates at a concentration of 10 μg/ml in PBS, pH 7.4. The plates were washed with PBS-T (0.05% Tween 20) and blocked with 2% bovine serum albumin (BSA) in PBS for 1 h. After blocking, serial dilutions of mouse sera were added and incubated for 2 h, followed by incubation with horseradish peroxidase (HRP)-conjugated anti-mouse IgG (Biolegend) for 1 h. The plates were washed and developed with TMB substrate (BD OptEIA™).

Quantitative Proteome Analysis of Skin Lesions

Peptide Extraction

Lesions were subjected to pulverization and supernatants were collected. Supernatants were combined with 500 μl of a lysis buffer comprised of 6 M urea, 7% sodium dodecylsulfate (SDS), and 50 mM triethylammonium bicarbonate (TEAB) adjusted to pH=8.1 with phosphoric acid (PA). Samples were subjected to probe sonication via three cycles of 10 seconds on and 10 seconds of rest at 20% amplitude. Samples were subjected to reducing conditions to break disulfide bonds via the addition of 5 μl of dithiothreitol (DTT) and incubation at 47° C. for 30 minutes. Samples were cooled at −20° C. for 5 minutes and reduced disulfide bonds were alkylated via the addition of 15 μl iodoacetamide (IAA) and incubation in a darkened environment for 20 minutes. The reaction was quenched through addition of 5 μl of DTT and incubation on the benchtop for 15 minutes. 27 μl of PA was added to each tube, followed by 1.5 mL of a binding buffer comprised of 90% methanol and 50 mM of TEAB with pH adjusted to 7.1 with PA. Samples were mixed through vortexing and added to the upper chamber of S-trap columns in 200 μl increments. Flow through was discarded for this and subsequent wash steps. S trap filters were washed 5 times with 165 μl of binding buffer. 125 μl of digestion buffer comprised of 50 mM TEAB with sequencing-grade trypsin (Promega) at a concentration of 40 μg/ml was added to the upper chamber of each S trap and allowed to partially saturate the filter. Protein digestion proceeded for 3 hours at 47° C. Digested peptide was eluted via addition and centrifugation of 125 μl of 50 mM TEAB, 125 μl of 5% formic acid (FA), and 125 μl of 50% acetonitrile (ACN) with 5% FA. Flow through was subjected to drying under vacuum. Peptides were then resuspended in 0.1% trifluoroacetic acid and desalted on C18 columns using the manufacturer's instructions (Waters).

Peptide Quantification, TMT Labeling, and Fractionation

Peptides were quantified using a Quantitative Colorimetric Peptide Assay (Pierce), following manufacturer's instructions. 50 μg of each sample was separated for tandem mass tag (TMT) labeling. TMTs were resuspended in dry acetonitrile to a final concentration of 10 μg/μl. Aliquoted peptide was resuspended in 50 μl of a solution of 30% dry acetonitrile with 200 mM HEPES. 8 μl of each TMT label was added to its assigned sample and labeling proceeded for one hour at room temperature on the benchtop. The reaction was quenched via addition of 9 μl of 5% hydroxylamine and incubation on the benchtop for 15 minutes. 50 μl of 1% TFA was added to each sample and samples were mixed together. The multiplexed sample was dried under vacuum and resuspended in 1 ml of 0.1% TFA before being desalted as above. The desalted sample was dried under vacuum. Samples were fractionated on an Ultimate 3000 HPLC using a gradient ranging from 5% to 35% acetonitrile with 10 mM ammonium bicarbonate, wherein 96 fractions were collected over 60 minutes. Fractions were concatenated using an alternating recombination strategy, and alternating column fractions were subjected to quantitative mass spectrometry-based analysis[42].

Mass Spectrometry Data Collection

Twelve fractions representing the multiplexed experiment were resuspended in 5% ACN with 5% FA and analyzed on an Orbitrap Fusion Mass Spectrometer with in-line Easy-nLC 1000. 3 μl of each fraction was loaded onto a 30 cm long column pulled and packed in-house with contents from the tip as follows: 0.5 cm of 5.im C4, 0.5 cm of 3.im C18, and 29 cm 1.8.im C18. The inner diameter of the column was 100.im, while the outer was 350.im. The column was attached to the nLC via an electrospray-enabled T junction connecting the sample, waste, and column capillaries. MS1 data was collected in data-dependent mode with scans collected between 500-1200 m/z, a resolution of 60,000, and maximum inject time of 100 ms. Peptides were sequenced in the linear ion trap with rapid scan rate. Reporter ion fragmentation and detection occurred in the Orbitrap.

Data Analysis

For recombinant S protein mass spectrometry analysis, raw files were analyzed using GNPS to identify possible modifications using unbiased methods[43,44]. Raw spectral files were converted to mzML format using MSConvert[45]. Spectral networking revealed prominent modifications corresponding to deamidation, carboxylation, carbamylation, formylation, oxidation, deoxidation, and several forms of glycosylation. These modifications were used to inform the Byonic search node in Proteome Discoverer, where the GAS M1 5448 reference proteome was used to matched detected spectra to protein sequences.

For skin lesion quantitative proteomics, raw files were analyzed using Proteome Discoverer. MS2 spectra were matched to theoretical spectra generated against a *Mus musculus* reference proteome downloaded from Uniprot.com in a Sequest-HT node with a false discovery threshold of 0.01. Dynamic modifications were limited to oxidation of methionines, while static modifications included chemically-induced experimental modifications: TMT labels of lysine residues and peptide N-termini and carbamidomethylation of cysteine residues. Precursor ion mass tolerance was set to 50 ppm, while fragmentation ion tolerance was 0.6 Da. Resultant peptide spectral matches (PSMs) were first filtered to retain high confidence matches and non-rejected matches. PSMs with isolation interference values greater than 25 and average quantitative values lower than 10 were also removed. Resultant peptide spectral matches (PSMs) were summed to the protein level. Protein quantitative information was normalized through a two-step process. First, proteins were normalized against the average value for each protein which was itself normalized to the median of all averages. Next, the resulting values were normalized to a value resulting from the normalization of the channel median divided by the median of all values. The resulting values were subjected to hierarchical clustering and similarity matrix generation using Morpheus (software.broadinstitute.org/morpheus). All heatmaps were also generated using Morpheus. Network generation was performed using String-db with interaction threshold set to 0.7, and all networks were processed for image generation using Cytoscape.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

It should be understood that although the present invention has been specifically disclosed by certain aspects, embodiments, and optional features, modification, improvement and variation of such aspects, embodiments, and optional features can be resorted to by those skilled in the art, and that such modifications, improvements and variations are considered to be within the scope of this disclosure.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

REFERENCE(S)

1. Carapetis, J. R., Steer, A. C., Mulholland, E. K. & Weber, M. The global burden of group A streptococcal diseases. *Lancet Infect. Dis.* 5, 685-694 (2005).
2. Stevens, D. L. & Bryant, A. E. in *Streptococcus pyogenes: Basic Biology to Clinical Manifestations* (eds. Ferretti, J. J., Stevens, D. L. & Fischetti, V. A.) (University of Oklahoma Health Sciences Center, 2016).
3. Tyrrell, G. J. Does group A strep have any skin in the ARF game? *The Lancet Regional Health—Western Pacific* 8, 100114 (2021).
4. Carapetis, J. R. et al. Acute rheumatic fever and rheumatic heart disease. *Nat. Rev. Dis. Primers* 2, 15084 (2016).

5. Martin, W. J. et al. Post-infectious group A streptococcal autoimmune syndromes and the heart. *Autoimmun. Rev.* 14, 710-725 (2015).
6. Cunningham, M. W. Rheumatic fever, autoimmunity, and molecular mimicry: the streptococcal connection. *Int Rev Immunol* 33, 314-329 (2014).
7. Snider, L. A. & Swedo, S. E. Post-streptococcal autoimmune disorders of the central nervous system. *Curr. Opin. Neurol.* 16, 359-365 (2003).
8. Rodriguez-Iturbe, B. & Musser, J. M. The current state of poststreptococcal glomerulonephritis. *J. Am. Soc. Nephrol.* 19, 1855-1864 (2008).
9. Bisno, A. L., Rubin, F. A., Cleary, P. P., Dale, J. B. & National Institute of Allergy and Infectious Diseases. Prospects for a group A streptococcal vaccine: rationale, feasibility, and obstacles—report of a National Institute of Allergy and Infectious Diseases workshop. *Clin. Infect. Dis.* 41, 1150-1156 (2005).
10. Cunningham, M. W. Molecular Mimicry, Autoimmunity, and Infection: The Cross-Reactive Antigens of Group A Streptococci and their Sequelae. *Microbiol. Spectr.* 7, (2019).
11. Lapek, J. D. et al. Biomimetic Virulomics for Capture and Identification of Cell-Type Specific Effector Proteins. *ACS Nano* 11, 11831-11838 (2017).
12. Wierzbicki, I. H. et al. Group A streptococcal S protein utilizes red blood cells as immune camouflage and is a critical determinant for immune evasion. *Cell Rep.* 29, 2979-2989.e15 (2019).
13. Rodriguez-Ortega, M. J. et al. Characterization and identification of vaccine candidate proteins through analysis of the group A *Streptococcus* surface proteome. *Nat. Biotechnol.* 24, 191-197 (2006).
14. Kelley, L. A., Mezulis, S., Yates, C. M., Wass, M. N. & Sternberg, M. J. E. The Phyre2 web portal for protein modeling, prediction and analysis. *Nat. Protoc.* 10, 845-858 (2015).
15. Helal, Z. M., Rizk, D. E., Adel El-Sokkary, M. M. & Hassan, R. Prevalence and Characterization of *Streptococcus pyogenes* Clinical Isolates from Different Hospitals and Clinics in Mansoura. *Int J Microbiol* 2020, 1-11 (2020).
16. Konrad, P., Hufnagel, M., Berner, R. & Toepfner, N. Long-term, single-center surveillance of non-invasive group A streptococcal (GAS) infections, emm types and emm clusters. *Eur. J. Clin. Microbiol. Infect. Dis.* 39, 273-280 (2020).
17. Kaplan, E. L., Johnson, D. R., Rehder, C. D., Dehnbostel, J. & Romana, C. Changes in the distribution of serotypes of group a streptococci (gas) isolated from uncomplicated pharyngitis (up) between 1988-90 and 1994-95: an influence on the epidemiology of severe gas infections?+618. *Pediatr. Res.* 39, 106-106 (1996).
18. Ho, P. L. et al. Epidemiologic analysis of invasive and noninvasive group a streptococcal isolates in Hong Kong. *J. Clin. Microbiol.* 41, 937-942 (2003).
19. Hooven, T. A. et al. Complete Genome Sequence of *Streptococcus agalactiae* CNCTC 10/84, a Hypervirulent Sequence Type 26 Strain. *Genome Announc.* 2, (2014).
20. Xiao, Y. et al. A novel significance score for gene selection and ranking. *Bioinformatics* 30, 801-807 (2014).
21. Bogdan, C., Rollinghoff, M. & Diefenbach, A. The role of nitric oxide in innate immunity. *Immunol. Rev.* 173, 17-26 (2000).
22. Jiang, Z. et al. CD14 is required for MyD88-independent LPS signaling. *Nat. Immunol.* 6, 565-570 (2005).
23. Henneke, P. et al. Novel engagement of CD14 and multiple toll-like receptors by group B streptococci. *J. Immunol.* 167, 7069-7076 (2001).
24. Ueno, N., Takeya, R., Miyano, K., Kikuchi, H. & Sumimoto, H. The NADPH oxidase Nox3 constitutively produces superoxide in a p22phox-dependent manner: its regulation by oxidase organizers and activators. *J. Biol. Chem.* 280, 23328-23339 (2005).
25. Vatansever, F. et al. Antimicrobial strategies centered around reactive oxygen species—bactericidal antibiotics, photodynamic therapy, and beyond. *FEMS Microbiol. Rev.* 37, 955-989 (2013).
26. Yoshida, L. et al. Expression of a p67(phox) homolog in Caco-2 cells giving O(2)(−)-reconstituting ability to cytochrome b(558) together with recombinant p47(phox). *Biochem. Biophys. Res. Commun.* 296, 1322-1328 (2002).
27. Chung, K. Y., Day, P. W., Vélez-Ruiz, G., Sunahara, R. K. & Kobilka, B. K. Identification of GPCR-interacting cytosolic proteins using HDL particles and mass spectrometry-based proteomic approach. *PLOS One* 8, e54942 (2013).
28. Zvonok, N. et al. Mass spectrometry-based GPCR proteomics: comprehensive characterization of the human cannabinoid 1 receptor. *J. Proteome Res.* 9, 1746-1753 (2010).
29. Futosi, K., Fodor, S. & Mócsai, A. Neutrophil cell surface receptors and their intracellular signal transduction pathways. *Int. Immunopharmacol.* 17, 638-650 (2013).
30. Eisele, N. A., Lee-Lewis, H., Besch-Williford, C., Brown, C. R. & Anderson, D. M. Chemokine receptor CXCR2 mediates bacterial clearance rather than neutrophil recruitment in a murine model of pneumonic plague. *Am. J. Pathol.* 178, 1190-1200 (2011).
31. Hawn, T. R. et al. Genetic variation of the human urinary tract innate immune response and asymptomatic bacteriuria in women. *PLOS One* 4, e8300 (2009).
32. Tsai, W. C. et al. CXC chemokine receptor CXCR2 is essential for protective innate host response in murine *Pseudomonas aeruginosa* pneumonia. *Infect. Immun.* 68, 4289-4296 (2000).
33. Herbold, W. et al. Importance of CXC chemokine receptor 2 in alveolar neutrophil and exudate macrophage recruitment in response to pneumococcal lung infection. *Infect. Immun.* 78, 2620-2630 (2010).
34. Guilherme, L., Postol, E., Ferreira, F. M., DeMarchi, L. M. F. & Kalil, J. StreptInCor: a model of anti-*Streptococcus pyogenes* vaccine reviewed. *Auto Immun. Highlights* 4, 81-85 (2013).
35. Mills, J. L. S. et al. M-protein based vaccine induces immunogenicity and protection from *Streptococcus pyogenes* when delivered on a high-density microarray patch (HD-MAP). *npj Vaccines* 5, 74 (2020).
36. Guilherme, L., Ferreira, F. M., Köhler, K. F., Postol, E. & Kalil, J. A vaccine against *Streptococcus pyogenes*: the potential to prevent rheumatic fever and rheumatic heart disease. *Am J Cardiovasc Drugs* 13, 1-4 (2013).
37. Reglinski, M., Lynskey, N. N., Choi, Y. J., Edwards, R. J. & Sriskandan, S. Development of a multicomponent vaccine for *Streptococcus pyogenes* based on the antigenic targets of IVIG. *J. Infect.* 72, 450-459 (2016).
38. Rivera-Hernandez, T. et al. An experimental group A *streptococcus* vaccine that reduces pharyngitis and tonsillitis in a nonhuman primate model. *M Bio* 10, (2019).
39. Madeira, F. et al. The EMBL-EBI search and sequence analysis tools APIs in 2019. *Nucleic Acids Res.* 47, W636-W641 (2019).

40. Galili, T. dendextend: an R package for visualizing, adjusting and comparing trees of hierarchical clustering. *Bioinformatics* 31, 3718-3720 (2015).

41. Paradis, E., Claude, J. & Strimmer, K. APE: Analyses of Phylogenetics and Evolution in R language. *Bioinformatics* 20, 289-290 (2004).

42. Wang, Y. et al. Reversed-phase chromatography with multiple fraction concatenation strategy for proteome profiling of human MCF10A cells. *Proteomics* 11, 2019-2026 (2011).

43. Wang, M. et al. Sharing and community curation of mass spectrometry data with Global Natural Products Social Molecular Networking. *Nat. Biotechnol.* 34, 828-837 (2016).

44. Wozniak, J. M. et al. Mortality Risk Profiling of *Staphylococcus aureus* Bacteremia by Multi-omic Serum Analysis Reveals Early Predictive and Pathogenic Signatures. *Cell* 182, 1311-1327.e14 (2020).

45. Chambers, M. C. et al. A cross-platform toolkit for mass spectrometry and proteomics. *Nat. Biotechnol.* 30, 918-920 (2012).

What is claimed is:

1. A method of treating or protecting against a Group A *Streptococcus* (GAS) infection in a subject in need thereof, comprising administering to the subject an effective amount of an isolated *Streptococcus*(S) protein comprising SEQ ID NO: 1 or an equivalent thereof having at least 95% sequence identity to SEQ ID NO: 1, thereby treating or protecting against the GAS infection in the subject.

2. The method of claim 1, wherein the S protein comprises SEQ ID NO: 1.

3. The method of claim 1, wherein the S protein consists of SEQ ID NO: 1.

4. The method of claim 1, wherein the Group A *Streptococcus* is *Streptococcus pyogenes* (*S. pyogenes*).

5. The method of claim 1, wherein the equivalent of SEQ ID NO: 1 comprises an amino acid sequence of any one of SEQ ID NOs: 2-37.

6. The method of claim 1, wherein the equivalent comprises at least one post-transcriptional modification selected from deamidation, oxidation, dioxidation, formylation, carboxylation, carbamylation, or glycosylation.

7. The method of claim 1, wherein further comprising administering an adjuvant to the subject that comprises an aluminum hydroxide adjuvant.

8. The method of claim 1, wherein the ratio of the *Streptococcus* S protein to the adjuvant is about 10:1 to about 1:30.

9. The method of claim 1, further comprising administering a therapy for treating a *Streptococcus* infection to the subject comprising an antibiotic or an immunogenic antigen of a pathogen other than *Streptococcus* or GAS to the subject.

10. The method of claim 1, wherein the subject has been infected by or has a high risk of being infected by *Streptococcus* Group A.

11. The method of claim 3, wherein the subject has been infected by or has a high risk of being infected by *Streptococcus* group A.

* * * * *

SEQUENCE LISTING

```
<160> NUMBER OF SEQ ID NOS: 38

<210> SEQ ID NO 1
<211> LENGTH: 158
<212> TYPE: PRT
<213> ORGANISM: Streptococcus pyogenes

<400> SEQUENCE: 1

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 2
<211> LENGTH: 158
<212> TYPE: PRT
<213> ORGANISM: Streptococcus pyogenes

<400> SEQUENCE: 2

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95
```

```
Ser Thr Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 3
<211> LENGTH: 158
<212> TYPE: PRT
<213> ORGANISM: Streptococcus pyogenes

<400> SEQUENCE: 3

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Lys Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 4
<211> LENGTH: 158
<212> TYPE: PRT
<213> ORGANISM: Streptococcus pyogenes

<400> SEQUENCE: 4

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Gly Thr Gly Glu Thr Leu
            100                 105                 110
```

```
Thr Val Leu Ala Gly Glu Gly Ala Ala Ser Ile Ala Ala Arg Ser Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 5
<211> LENGTH: 158
<212> TYPE: PRT
<213> ORGANISM: Streptococcus pyogenes

<400> SEQUENCE: 5

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Gln Lys Thr Ser Ser Ser Ser Thr Thr Thr Asp Thr Thr Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 6
<211> LENGTH: 158
<212> TYPE: PRT
<213> ORGANISM: Streptococcus pyogenes

<400> SEQUENCE: 6

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Ala Ser Ser Ser Ser Thr Thr Thr Asp Thr Thr Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125
```

-continued

```
Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 7
<211> LENGTH: 158
<212> TYPE: PRT
<213> ORGANISM: Streptococcus pyogenes

<400> SEQUENCE: 7

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Ala Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 8
<211> LENGTH: 158
<212> TYPE: PRT
<213> ORGANISM: Streptococcus pyogenes

<400> SEQUENCE: 8

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Gly Thr Gly Glu Thr Leu
            100                 105                 110

Thr Val Leu Val Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140
```

Gly Tyr Trp Tyr Ala Asn Pro Gly Asp Gln Val Thr Ile Lys
145 150 155

<210> SEQ ID NO 9
<211> LENGTH: 158
<212> TYPE: PRT
<213> ORGANISM: Streptococcus pyogenes

<400> SEQUENCE: 9

Met Ala Lys Glu Pro Trp Glu Glu Lys Ile Val Asp Asp Thr Ile Gly
1 5 10 15

Thr Arg Thr Arg Lys Ser Arg Asn Ala Phe Ile Ser Thr Pro Trp Leu
20 25 30

Thr Ala Leu Leu Ser Val Phe Phe Val Ile Ile Val Ala Ile Leu Phe
35 40 45

Ile Phe Phe Tyr Thr Ser Asn Ser Gly Ser Asn Arg Gln Ala Glu Thr
50 55 60

Asn Gly Phe Tyr Gly Ala Ser Thr His Lys Lys Thr Arg Lys Ala Ser
65 70 75 80

Asn Ala Lys Lys Thr Ser Ser Ser Ser Thr Thr Thr Asp Thr Thr Pro
85 90 95

Ser Ser Glu Glu Thr Leu Ala Ser Ser Glu Gly Thr Gly Lys Thr Leu
100 105 110

Thr Val Leu Ala Gly Glu Gly Ala Ala Ser Ile Ala Ala Arg Ala Gly
115 120 125

Ile Ser Val Glu Gln Leu Gln Ala Leu Asn Pro Glu His Met Thr Gln
130 135 140

Gly Tyr Trp Tyr Ala Asn Pro Gly Asp Gln Val Thr Ile Lys
145 150 155

<210> SEQ ID NO 10
<211> LENGTH: 158
<212> TYPE: PRT
<213> ORGANISM: Streptococcus pyogenes

<400> SEQUENCE: 10

Met Ala Lys Glu Pro Trp Glu Glu Lys Ile Val Asp Asp Thr Ile Gly
1 5 10 15

Thr Arg Thr Arg Lys Ser Arg Asn Ala Phe Ile Ser Thr Pro Trp Leu
20 25 30

Thr Ala Leu Leu Ser Val Phe Phe Val Ile Ile Val Ala Ile Leu Phe
35 40 45

Ile Phe Phe Tyr Thr Ser Asn Ser Gly Ser Asn Arg Gln Thr Glu Thr
50 55 60

Asn Gly Phe Tyr Gly Ala Ser Thr His Lys Lys Thr Arg Lys Ala Ser
65 70 75 80

Asn Ala Lys Lys Thr Ser Ser Ser Ser Thr Thr Thr Asp Thr Thr Pro
85 90 95

Ser Ser Glu Glu Thr Leu Ala Ser Ser Glu Gly Thr Gly Glu Thr Leu
100 105 110

Thr Val Leu Ala Gly Glu Gly Ala Ala Ser Ile Ala Ala Arg Ala Gly
115 120 125

Ile Ser Val Glu Gln Leu Gln Ala Leu Asn Pro Glu His Met Thr Gln
130 135 140

Gly Tyr Trp Tyr Ala Asn Pro Gly Asp Gln Val Thr Ile Lys
145 150 155

<210> SEQ ID NO 11
<211> LENGTH: 158
<212> TYPE: PRT
<213> ORGANISM: Streptococcus pyogenes

<400> SEQUENCE: 11

```
Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Gly Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155
```

<210> SEQ ID NO 12
<211> LENGTH: 158
<212> TYPE: PRT
<213> ORGANISM: Streptococcus pyogenes

<400> SEQUENCE: 12

```
Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Gly Thr Gly Glu Asn Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155
```

<210> SEQ ID NO 13

-continued

```
<211> LENGTH: 158
<212> TYPE: PRT
<213> ORGANISM: Streptococcus pyogenes

<400> SEQUENCE: 13

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Lys Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 14
<211> LENGTH: 158
<212> TYPE: PRT
<213> ORGANISM: Streptococcus pyogenes

<400> SEQUENCE: 14

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Ile Thr Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 15
<211> LENGTH: 158
<212> TYPE: PRT
<213> ORGANISM: Streptococcus pyogenes
```

<400> SEQUENCE: 15

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Ile Ile Lys
145                 150                 155

<210> SEQ ID NO 16
<211> LENGTH: 158
<212> TYPE: PRT
<213> ORGANISM: Streptococcus pyogenes

<400> SEQUENCE: 16

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Ile Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155

<210> SEQ ID NO 17
<211> LENGTH: 158
<212> TYPE: PRT
<213> ORGANISM: Streptococcus pyogenes

<400> SEQUENCE: 17

-continued

```
Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp His Val Thr Ile Lys
145                 150                 155


<210> SEQ ID NO 18
<211> LENGTH: 158
<212> TYPE: PRT
<213> ORGANISM: Streptococcus pyogenes

<400> SEQUENCE: 18

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Leu Thr Thr Thr Asp Thr Thr Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 19
<211> LENGTH: 158
<212> TYPE: PRT
<213> ORGANISM: Streptococcus pyogenes

<400> SEQUENCE: 19

Met Ala Lys Glu Pro Trp Glu Glu Lys Ile Val Asp Asp Thr Ile Gly
1               5                   10                  15
```

-continued

```
Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Glu Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 20
<211> LENGTH: 158
<212> TYPE: PRT
<213> ORGANISM: Streptococcus pyogenes

<400> SEQUENCE: 20

Met Ala Lys Glu Pro Trp Glu Glu Arg Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Ala Ser Ser Ser Ser Thr Thr Thr Asp Thr Thr Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 21
<211> LENGTH: 158
<212> TYPE: PRT
<213> ORGANISM: Streptococcus pyogenes

<400> SEQUENCE: 21

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30
```

```
Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Gly Thr Gly Glu Thr Ile
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Ile Ile Lys
145                 150                 155
```

<210> SEQ ID NO 22
<211> LENGTH: 158
<212> TYPE: PRT
<213> ORGANISM: Streptococcus pyogenes

<400> SEQUENCE: 22

```
Met Ala Lys Glu Pro Trp Glu Glu Lys Asn Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155
```

<210> SEQ ID NO 23
<211> LENGTH: 158
<212> TYPE: PRT
<213> ORGANISM: Streptococcus pyogenes

<400> SEQUENCE: 23

```
Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45
```

-continued

```
Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Gly Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 24
<211> LENGTH: 158
<212> TYPE: PRT
<213> ORGANISM: Streptococcus pyogenes

<400> SEQUENCE: 24

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Val Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 25
<211> LENGTH: 158
<212> TYPE: PRT
<213> ORGANISM: Streptococcus pyogenes

<400> SEQUENCE: 25

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60
```

-continued

```
Asn Gly Phe Tyr Gly Ala Ser Thr His Lys Lys Ala Arg Lys Ala Ser
65                  70                  75                  80

Asn Ala Lys Lys Ala Ser Ser Ser Ser Thr Thr Thr Asp Thr Thr Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 26
<211> LENGTH: 158
<212> TYPE: PRT
<213> ORGANISM: Streptococcus pyogenes

<400> SEQUENCE: 26

Met Ala Lys Glu Pro Trp Glu Glu Lys Ile Val Gly Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 27
<211> LENGTH: 158
<212> TYPE: PRT
<213> ORGANISM: Streptococcus pyogenes

<400> SEQUENCE: 27

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80
```

```
Asn Ala Lys Lys Thr Ser Ser Ser Ser Thr Thr Thr Asp Thr Thr Pro
                85                  90                  95

Ser Ser Glu Glu Thr Leu Ala Ser Ser Glu Gly Thr Ala Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Ile Ile Lys
145                 150                 155


<210> SEQ ID NO 28
<211> LENGTH: 158
<212> TYPE: PRT
<213> ORGANISM: Streptococcus pyogenes

<400> SEQUENCE: 28

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Ile Asp Thr Lys Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 29
<211> LENGTH: 158
<212> TYPE: PRT
<213> ORGANISM: Streptococcus pyogenes

<400> SEQUENCE: 29

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95
```

-continued

```
Ser Ser Glu Glu Thr Leu Ala Ser Ser Glu Val Thr Gly Glu Thr Ile
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Thr Ile Lys
145                 150                 155


<210> SEQ ID NO 30
<211> LENGTH: 158
<212> TYPE: PRT
<213> ORGANISM: Streptococcus pyogenes

<400> SEQUENCE: 30

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Ile Ser Ser Ser Ser Thr Thr Thr Asp Thr Thr Pro
                85                  90                  95

Ser Ser Glu Glu Thr Leu Ala Ser Ser Glu Gly Thr Gly Glu Thr Ile
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Ile Ile Lys
145                 150                 155


<210> SEQ ID NO 31
<211> LENGTH: 158
<212> TYPE: PRT
<213> ORGANISM: Streptococcus pyogenes

<400> SEQUENCE: 31

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Thr Ser Ser Glu Gly Thr Gly Glu Thr Ile
            100                 105                 110
```

-continued

```
Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Ile Ile Lys
145                 150                 155


<210> SEQ ID NO 32
<211> LENGTH: 158
<212> TYPE: PRT
<213> ORGANISM: Streptococcus pyogenes

<400> SEQUENCE: 32

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Val Thr Gly Glu Thr Leu
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Ile Ile Lys
145                 150                 155


<210> SEQ ID NO 33
<211> LENGTH: 158
<212> TYPE: PRT
<213> ORGANISM: Streptococcus pyogenes

<400> SEQUENCE: 33

Met Ala Lys Glu Pro Trp Glu Glu Lys Asn Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Gly Thr Gly Glu Thr Leu
            100                 105                 110

Thr Val Leu Ala Gly Glu Gly Ala Ala Ser Ile Ala Ala Arg Ala Gly
        115                 120                 125
```

-continued

```
Ile Ser Val Glu Gln Leu Gln Ala Leu Asn Pro Glu His Met Ile Gln
    130                 135                 140

Gly Tyr Trp Tyr Ala Asn Pro Gly Asp Gln Val Thr Ile Lys
145                 150                 155


<210> SEQ ID NO 34
<211> LENGTH: 158
<212> TYPE: PRT
<213> ORGANISM: Streptococcus pyogenes

<400> SEQUENCE: 34

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Val Thr Gly Glu Thr Ile
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Ile Ile Lys
145                 150                 155


<210> SEQ ID NO 35
<211> LENGTH: 158
<212> TYPE: PRT
<213> ORGANISM: Streptococcus pyogenes

<400> SEQUENCE: 35

Met Ala Lys Glu Pro Trp Glu Glu Lys Ile Ile Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Val Thr Gly Glu Thr Ile
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140
```

-continued

```
Gly Tyr Trp Tyr Ala Asn Pro Gly Asp Gln Val Ile Ile Lys
145                 150                 155


<210> SEQ ID NO 36
<211> LENGTH: 158
<212> TYPE: PRT
<213> ORGANISM: Streptococcus pyogenes

<400> SEQUENCE: 36

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Met
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Val Thr Gly Glu Thr Ile
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Thr Gln
    130                 135                 140

Gly Tyr Trp Tyr Ala Asn Pro Gly Asp Gln Val Ile Ile Lys
145                 150                 155


<210> SEQ ID NO 37
<211> LENGTH: 158
<212> TYPE: PRT
<213> ORGANISM: Streptococcus pyogenes

<400> SEQUENCE: 37

Met Ala Lys Glu Pro Trp Glu Glu Lys Ile Val Asp Asp Thr Ile Gly
1               5                   10                  15

Thr Arg Thr Arg Lys Ser Arg Asn Ala Phe Ile Ser Thr Pro Trp Leu
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Ala Glu Thr
    50                  55                  60

Asn Gly Phe Tyr Gly Ala Ser Thr His Lys Lys Thr Arg Lys Ala Ser
65                  70                  75                  80

Asn Ala Lys Lys Thr Ser Ser Ser Ser Thr Thr Thr Asp Thr Thr Pro
                85                  90                  95

Ser Ser Glu Glu Thr Leu Ala Ser Ser Glu Val Thr Gly Glu Thr Ile
            100                 105                 110

Thr Val Leu Ala Gly Glu Gly Ala Ala Ser Ile Ala Ala Arg Ala Gly
        115                 120                 125

Ile Ser Val Glu Gln Leu Gln Ala Leu Asn Pro Glu His Met Ile Gln
    130                 135                 140

Gly Tyr Trp Tyr Ala Asn Pro Gly Asp Gln Val Ile Ile Lys
145                 150                 155
```

<210> SEQ ID NO 38
<211> LENGTH: 158
<212> TYPE: PRT
<213> ORGANISM: Streptococcus pyogenes
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (62)..(62)
<223> OTHER INFORMATION: Any amino acid
<220> FEATURE:
<221> NAME/KEY: MOD_RES
<222> LOCATION: (76)..(77)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (85)..(85)
<223> OTHER INFORMATION: Any amino acid
<220> FEATURE:
<221> NAME/KEY: MOD_RES
<222> LOCATION: (89)..(89)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (94)..(95)
<223> OTHER INFORMATION: Any amino acid
<220> FEATURE:
<221> NAME/KEY: MOD_RES
<222> LOCATION: (98)..(98)
<223> OTHER INFORMATION: Any amino acid
<220> FEATURE:
<221> NAME/KEY: MOD_RES
<222> LOCATION: (101)..(101)
<223> OTHER INFORMATION: Any amino acid
<220> FEATURE:
<221> NAME/KEY: MOD_RES
<222> LOCATION: (103)..(103)
<223> OTHER INFORMATION: Any amino acid
<220> FEATURE:
<221> NAME/KEY: MOD_RES
<222> LOCATION: (107)..(107)
<223> OTHER INFORMATION: Any amino acid
<220> FEATURE:
<221> NAME/KEY: MOD_RES
<222> LOCATION: (109)..(112)
<223> OTHER INFORMATION: Any amino acid
<220> FEATURE:
<221> NAME/KEY: MOD_RES
<222> LOCATION: (116)..(116)
<223> OTHER INFORMATION: Any amino acid
<220> FEATURE:
<221> NAME/KEY: MOD_RES
<222> LOCATION: (120)..(120)
<223> OTHER INFORMATION: Any amino acid
<220> FEATURE:
<221> NAME/KEY: MOD_RES
<222> LOCATION: (127)..(127)
<223> OTHER INFORMATION: Any amino acid
<220> FEATURE:
<221> NAME/KEY: MOD_RES
<222> LOCATION: (132)..(132)
<223> OTHER INFORMATION: Any amino acid
<220> FEATURE:
<221> NAME/KEY: MOD_RES -continued

```
<222> LOCATION: (143)..(143)
<223> OTHER INFORMATION: Any amino acid
<220> FEATURE:
<221> NAME/KEY: MOD_RES
<222> LOCATION: (154)..(154)
<223> OTHER INFORMATION: Any amino acid
<220> FEATURE:
<221> NAME/KEY: MOD_RES
<222> LOCATION: (156)..(156)
<223> OTHER INFORMATION: Any amino acid

<400> SEQUENCE: 38

Met Ala Lys Glu Pro Trp Glu Glu Xaa Xaa Xaa Xaa Asp Thr Ile Gly
1               5                   10                  15

Thr Arg Thr Arg Lys Ser Arg Asn Ala Phe Ile Ser Thr Pro Trp Xaa
            20                  25                  30

Thr Ala Leu Leu Ser Val Phe Phe Val Ile Ile Val Ala Ile Leu Phe
        35                  40                  45

Ile Phe Phe Tyr Thr Ser Asn Ser Gly Ser Asn Arg Gln Xaa Glu Thr
    50                  55                  60

Asn Gly Phe Tyr Gly Ala Ser Thr His Lys Lys Xaa Xaa Lys Ala Ser
65                  70                  75                  80

Asn Ala Xaa Lys Xaa Ser Ser Ser Xaa Thr Thr Xaa Asp Xaa Xaa Pro
                85                  90                  95

Ser Xaa Glu Glu Xaa Leu Xaa Ser Ser Glu Xaa Thr Xaa Xaa Xaa Xaa
            100                 105                 110

Thr Val Leu Xaa Gly Glu Gly Xaa Ala Ser Ile Ala Ala Arg Xaa Gly
        115                 120                 125

Ile Ser Val Xaa Gln Leu Gln Ala Leu Asn Pro Glu His Met Xaa Gln
    130                 135                 140

Gly Tyr Trp Tyr Ala Asn Pro Gly Asp Xaa Val Xaa Ile Lys
145                 150                 155
```